(12) United States Patent
Thevelein et al.

(10) Patent No.: US 10,000,759 B2
(45) Date of Patent: Jun. 19, 2018

(54) YEAST ALLELES INVOLVED IN MAXIMAL ALCOHOL ACCUMULATION CAPACITY AND TOLERANCE TO HIGH ALCOHOL LEVELS

(71) Applicants: VIB VZW, Ghent (BE); Katholieke Universiteit Leuven, K.U.Leuven R&D, Leuven (BE)

(72) Inventors: Johan Thevelein, Blanden (BE); Annelies Goovaerts, Putte (BE); Françoise Dumortier, Blanden (BE); Maria Remedios Foulquie-Moreno, Brussels (BE); Steve Swinnen, Zichem (BE); Thiago Martins Pais, Sinop (BR)

(73) Assignees: VIB VZW, Ghent (BE); KATHOLIEKE UNIVERSITEIT LEUVEN, K.U. LEUVEN R&D, Leuven (BE)

( * ) Notice: Subject to any disclaimer, the term of this patent is extended or adjusted under 35 U.S.C. 154(b) by 0 days. days.

(21) Appl. No.: 14/784,893

(22) PCT Filed: Apr. 15, 2014

(86) PCT No.: PCT/EP2014/057629
§ 371 (c)(1),
(2) Date: Oct. 15, 2015

(87) PCT Pub. No.: WO2014/170330
PCT Pub. Date: Oct. 23, 2014

(65) Prior Publication Data
US 2016/0068848 A1    Mar. 10, 2016

(30) Foreign Application Priority Data

Apr. 15, 2013 (EP) .................................... 13163727

(51) Int. Cl.
*C12N 15/81* (2006.01)
*C12P 7/06* (2006.01)
*C07K 14/395* (2006.01)

(52) U.S. Cl.
CPC ............ *C12N 15/81* (2013.01); *C07K 14/395* (2013.01); *C12P 7/06* (2013.01); *Y02E 50/17* (2013.01)

(58) Field of Classification Search
CPC ......... C12N 15/81; C07K 14/395; C12P 7/06; Y02E 50/17
See application file for complete search history.

(56) References Cited

U.S. PATENT DOCUMENTS

2010/0311137 A1    12/2010   Brown et al.
2012/0329112 A1    12/2012   Brown et al.
2014/0228224 A1    8/2014    Thevelein et al.
2015/0225747 A1    8/2015    Thevelein et al.
2015/0307833 A1    10/2015   Thevelein et al.
2016/0304888 A1    10/2016   Thevelein et al.

FOREIGN PATENT DOCUMENTS

| EP | 1338608 A2 | 8/2003 |
|---|---|---|
| WO | 3062430 | 7/2003 |
| WO | 2009029644 A1 | 3/2009 |
| WO | 2010111587 | 9/2010 |
| WO | 2012175552 | 12/2012 |
| WO | 2014048863 A1 | 4/2014 |
| WO | 2014090930 A1 | 6/2014 |
| WO | 2014170330 | 10/2014 |

OTHER PUBLICATIONS

Pais (PLOS Genetics (2013) vol. 9, pp. 1-18).*
Boekhout (Nature(2005) vol. 434, pp. 449-450).*
Pederson et al (Growth of Yeast in Stored Grape juice (1958) pp. 1-6).*
Ogihara et al (yeast 2008) vol. 25, pp. 419-432).*
Pais et al (ICY abstract Aug. 26, 2012).*
Swinnen (Genome Research (2012) vol. 22, pp. 975-984, published on line Mar. 12, 2012).*
GenPept accession No. CAY82518 (https://www.ncbi.nlm.nih.gov/protein/259149276?sat=43&satkey=8774095, Sep. 29, 2009).*
Genbank accession numbers(http://www.yeastgenome.org/strain/S288C/overview, downloaded Jul. 5, 2017).*
PCT International Search Report and Written Opinion, PCT/EP2014/057629.
Swinnen et al., Identification of novel causative genes determining the complex trait of high ethanol tolerance in yeast using pooled-segregant whole-genome sequence analysis, Genome Research, May 1, 2015, pp. 975-984, vol. 22, No. 5, Cold Spring Harbor Laboratory Press.
Hong et al., Identification of gene targets eliciting improved alcohol tolerance in Saccharomyces cerevisiae through inverse metabolic engineering, Journal of Biotechnology, Aug. 20, 2010, pp. 52-59, vol. 149, No. 1-2, Elsevier Science Publishers.
Gottschalk et al., A comprehensive biochemical and genetic analysis of the yeast U1 snRNP reveals five novel proteins, RNA (New York).vol. 4. No. 4. Apr. 1998 (Apr. 1998). pp. 374-393.
Posas et al., Activation of the yeast SSK2 MAP kinase kinase kinase by the SSK1 two-component response regulator, The EMBO Journal, Mar. 2, 1998, pp. 1385-1394, vol. 17, No. 5.
Bracken et al, Reassembly and protection of small nuclear ribonucleoprotein particles by heat shock proteins in yeast cells, RNA (New York).vol. 5. No. 12. Dec. 1999, pp. 1586-1596.

(Continued)

*Primary Examiner* — Steven Pohnert
(74) *Attorney, Agent, or Firm* — TraskBritt, P.C.

(57) ABSTRACT

The disclosure relates to a specific yeast allele of KIN3 that is involved in maximal alcohol accumulation and/or in tolerance to high alcohol levels. Preferably, the alcohol is ethanol. In a preferred embodiment, this specific allele is combined with specific alleles of ADE1 and/or VPS70. More specifically, the disclosure relates to the use of these alleles for the construction and/or selection of high alcohol tolerant yeasts, by stacking of positive alleles, or the selection and construction of low alcohol producing yeasts by stacking of negative alleles.

11 Claims, 14 Drawing Sheets
(6 of 14 Drawing Sheet(s) Filed in Color)

(56) References Cited

OTHER PUBLICATIONS

Nissen et al., Anaerobic and Aerobic Batch Cultivation of Saccharomyces Cerevisiae Mutants Impaired in Glycerol Synthesis, Yeast, Mar. 30, 2000, pp. 463-474, vol. 16, No. 5, John Wiley & Sons ltd, GB.

Deutschbauer et al., Quantitative trait loci mapped to single-nucleotide resolution in yeast, Nature Genetics, 2005, vol. 37, No. 12.

Bro et al., In silico aided metabolic engineering of *Saccharomyces cerevisiae* for improved bioethanol production, Metabolic Engineering, Mar. 1, 2006, pp. 102-111, vol. 8 No. 2.

Wei, W., et al., "Genome sequencing and comparative analysis of *Saccharomyces cerevisiae* strain YJM789," Proceedings of the National Academy of Sciences, vol. 104, No. 31, pp. 12825-12830, Jul. 2007.

Horie et al., Phosphorylated Ssk1 Prevents Unphosphorylated Sskl from Activating the Ssk2 Mitogen-Activated Protein Kinase Kinase Kinase in the Yeast High-Osmolarity Glycerol Osmoregulatory Pathway, Molecular and Cellular Biology, Sep. 1, 2008, pp. 5172-5183, vol. 28, No. 17.

Sinha et al., Sequential elimination of major effect contributors identifies additional quantitative trait loci conditioning high-temperature growth in yeast, Genetics, vol. 180. 2008, pp. 1661-1670.

PCT International Search Report, PCT/EP2013/069660, dated Nov. 22, 2013.

Yang (Biotechnology and Bioengineering vol. 108 No. 8 Aug. 2011 (pre-published online Mar. 17, 2011)).

Duitama et al., Towards accurate detection and genotyping of expressed variants from whole transcriptome sequencing data, BMC Genomics, Apr. 12, 2012, p. S6, vol. 13, No. Suppl 2., 10 pages, Biomed Central Ltd, London, UK.

Yang et al., QTL Analysis of High Thermotolerance with Superior and Downgraded Parental Yeast Strains Reveals New Minor QTLs and Converges on Novel Causative Alleles Involved in RNA Processing, PLOS Genetics, vol. 9. No. 8. Aug. 2013 (Aug. 2013).

International Search Report and Written Opinion for International Application No. PCT/EP2012/061823, dated Sep. 4, 2012, 12 pages.

PCT International Search Report, PCT/EP2013/076344, dated Mar. 6, 2014.

Sequence Reference File S288C dated Feb. 3, 2011, for *Saccharomyces cerevisiae*, strain S288C.

\* cited by examiner

A

B

C

SEQUENCE LISTING

<160> NUMBER OF SEQ ID NOS: 12

<210> SEQ ID NO 1
<211> LENGTH: 1674
<212> TYPE: DNA
<213> ORGANISM: Saccharomyces cerevisiae

<400> SEQUENCE: 1

```
atttacatat actacaagtc gccagtgtaa ctcctcactg aatatgattc atacataccc      60
gtatgtatta atgtataaat gttctcagag caaattttat cgatatcttg tttgccagtg     120
gtatgcaggt ttggcaaatt ttttaccata atatccgttt atagattctg gaaccttacc     180
aactttctta ccgctaatta cttccctggc tcgctcctcc actgcctggg taaattgttc     240
cttcaactga ctcagttctc tttcatattc aatagcttgc ttctcgagga ttttttcaat     300
gtttgtcagc tcattttcat agtccagtaa cttcctttca aatctctcta attgcaacga     360
ctttcttgca gttcgtatct gaatatcttg cagtaattca aaagtggaag gcctggttct     420
taagttcaca tctatcattg aatgtattat ggcattaagc cctctagagt aatactcagg     480
gacggtgtca catttcccgt ttttaatctt agtttgtagc tcgagataat tttttgcctg     540
aaatgggggg tgtaacgaac acatctcaaa aataacacaa cctagtgacc agatgtcgga     600
tagtggggag tatggttggt ccatcaacac ttcaggcgac atgtagtatg gtgtaccgac     660
gtatgttgtg gcaaattgaa tactagtttc cagagatttg gctaacccaa aatcacctaa     720
ctttaccaca acttgactat agtccatagg gctccccctt ttccctgaat tcactctatg     780
gtctctgtaa taattactat tcacttcctc gtgaccgtct acttgttcat taatattgta     840
atcgctatca tcatagctta agaatatatt tcctggtttc agatcacgat ggataacgat     900
gttttttgcct tttaccggtg gtttcatccg gtcatatatt gtggtcaaag ttggcaattc     960
aacaccataa tgacatttat agagcgcagt caataattgg gccaggatac cccacacaat    1020
tttttctggt atatatttat gctcctgttt gtagtgctta atcatctggg ataaatcacc    1080
cctggaacaa tattccatat aaaggtataa cacttctttt tgttcatcga agtcccagtt    1140
ataaaattct acaatatttt catgcttcaa ctgcgataga atgctacatt cagcgatcag    1200
ctgttgtctc tctttgctat tcatatggcc atatttgata tcctttctaa ccaaaagttt    1260
cttggtaggt atatggatga cttttcgtac agacccaaat gaacctctcc caatttcttc    1320
gagaacttgg tattctgacc ttggtgggtg tccctgctgc tgctgaggac tacggtattc    1380
ttggaaaaac tgtcgtctat gcatactcac acagagaatt gattcaatta tcaaatagca    1440
ctctcattga aattagtatt gtgaatcttg ctcttttcat gttatatgat ttgatattct    1500
tttgaaaagt cgcttttatt tacgtttaac ctaattagga aacgtaatga aaaaattcag    1560
aaaccttaaa aaaaaaactt ggctgtaacc tatcggaaga ctgtgccact gcaatcatgt    1620
cagatatcgt atttcagatt tattgattta tagctagaaa cattaacaaa atgc          1674
```

<210> SEQ ID NO 2
<211> LENGTH: 1353
<212> TYPE: DNA
<213> ORGANISM: Saccharomyces cerevisiae

<400> SEQUENCE: 2

```
agcttctttg tttacagcac ttgatccatg tagccatact cgaaatttca actcatctga      60 aactttcct gaaggttgaa aaagaatgcc ataagggtca cccgaagctt attcacgagt      120
cagtctgact cttgcgagag atgaggatgt aataatacta atctcgaaga tgccatctaa     180
tacatataga catatatata tatatatata cattctatat attcttaccc agattctttg     240
aggtaagacg gttgggtttt atcttttgca gttggtacta ttaagaacaa tcgaatcata     300
agcattgctt acaaagaata cacatacgaa atattaacga taatgtcaat tacgaagact     360
gaactggacg gtatattgcc attggtggcc agaggtaaag ttagagacat atatgaggta    420
gacgctggta cgttgctgtt tgttgctacg atcgtatct ctgcatatga cgttattatg    480
gaaaacagca ttcctgaaaa ggggatccta ttgaccaaac tgtcagagtt ctggttcaag    540
ttcctgtcca acgatgttcg taatcatttg gtcgacatcg ccccaggtaa gactattttc    600
gattatctac ctgcaaaatt gagcgaacca agtacaaaa cgcaactaga gaccgctct     660 ctattggttc acaaacataa actaattcca ttggaagtaa ttgtcagagg ctacatcacc    720
ggatctgctt ggaaagagta cgtaaaaaca ggtactgtgc atggtttgaa acaacctcaa    780
ggacttaaag aatctcaaga gttcccagaa ccaatcttca ccccatcgac caaggctgaa    840
caaggtgaac atgacgaaaa catctctcct gcccaggccg ctgagctggt gggtgaagat    900
ttgtcacgta gagtggcaga actggctgta aaactgtact ccaagtgcaa agattatgct    960
aaggagaagg gcatcatcat cgcagacact aaattcgaat tcggtattga cgaaaagacc   1020
aatgaaatta ttctagtgga cgaggtgcta acgccagact cctctagatt ctggaacggt   1080
gcctcttata aagtaggaga atcccaagat tcttacgata agcaattttt aagagactgg   1140
cttactgcta ataagttgaa cggtgttaac ggcgtcaaaa tgccccaaga cattgtcgac   1200
aggacaaggg ccaaatatat agaggcttat gaaacattga cagggtctaa atggtctcac   1260
taacgtgatt tacatatact acaagtcgcc agtgtaactc ctcactgaat atgattcata   1320
catacccgta tgtattaatg tataaatgtt ctc                                 1353
```

<210> SEQ ID NO 3
<211> LENGTH: 3436
<212> TYPE: DNA
<213> ORGANISM: Saccharomyces cerevisiae

<400> SEQUENCE: 3

```
tcgtacactg atttcttaag atggcaggac aaggatgccc tagatttgtc agcactaaat      60
gaagaacaag cacaaagggc catggacccg aataccgata taaatgagac aattcaacta    120
attgtagcgg caagtctatc ctccaaatgt ttatatttgg gtgttcaaat attaggtgat    180
gcgccaattt ggcctataat attatcgttc gctcatggtt tgcaatcaag agctatctat    240
agtgttacga aaaaagaaa cactagaata taagtccaat ttacaaatat ataatggcgg    300
ccgtctctat actatagtat ttacagaatt aaagcttaga actatcataa ctttcataat    360
ataccaccag gcttcaaaaa ggcattgttc cattcggagt ttgcttgagt ttgatggccc    420
gggtaaaaag gtttgacaag gcaaggggcc gtacttatta aaacaatttc aacatgcaca    480
attaagaatg taagagatat atgagaatga tacagagaga gagagagaga gagaaagagg    540
aaggtcaatt aaaggagaga actgttgtta atatggcaga ccctgatgac aatgaggccg    600
aagccactgg attacaacaa tatagtggtg agaccactcg cgatgacaat gaagaaagca    660
tgaatgattc tttcactttta acatccagga atagaggcag aagtaataca atatctagta   720
```

```
ttgttagtgg ttatgaaata atgaaagaac atatggacaa ggaaaagttt atgtacttga    780
ttctagcgag tctccttttg tacatgggat ttgttgccgc atttgctccc aggacgtctt    840
tatcaagaga ctttcggcgg tttcactctt ccagattgac gaatgcagag gtttatagga    900
tatacttgaa ctccttgcaa caggaaaata gagcgaaaga acatgtatac aagtatgctg    960
ggtacatgag caacggagca agtgattcgt caacgtttaa atataccttg gacgagtttc   1020
tagatatggg gtacaaaccc aaagttgaaa aatattaccc atggataggt gaaccagtag   1080
acactaacgt agctctttta gaaaatggta aagtggtcta cgaagcaagc atgatcgagg   1140
atagagttaa aggtgatcct gcttctcacg ctaggaaaag gcaaaagggt ttccatcaat   1200
attcaaaaaa tggaagtgta actgctcgat acgtgttttg caattatggt agcatcagtg   1260
actacaagct acttttgaag aaaaacattg atattgaaga taaatccac atcgtacgat    1320 cgggtaaaat actacctgga ttaaaggtaa agaatgcaga actttatggc gcttccagtg   1380
tcattatata tacagaccca tttgacgatg gtaaagttac tgaggaaaat gggtttttac   1440
actatcctta tggaccagca agaaacccaa gttatattaa gagagattct gtaaactatt   1500
tcagtgacac tccaggagat ccgacaactc cagggtatcc ctccaaggat tccgacactg   1560
aacatatgtc accggtaggg agagtgccga ggataccatc ggtgccgatg agtgctagag   1620
atgtccaacc aatttttagaa agattgaatg gcaggggttt tcaaattggg cccggtagta   1680
atataaaaga ttttggatca ttcactggac cttcaagctc tatcgataaa gtccatttgc   1740
ataatgagct aacttacaat atcaaggaaa tgagtagtgt agaggttagt atccctggta   1800
tattcactga gggggagatt attatcgag ctcataggga ttcgctcgcc tcgagtagcg    1860
ccggtgatgc aaatagtggc agtgctattc ttttagaaat tgcacgagga atgagtaaac   1920
tacttaagca tggttggaag ccactgcgtc ctatcaaact aataagttgg gatggtgaac   1980
gatccggcct tctgggatct acagattatg cagaagctca tgctgcgatt ctcaggagaa   2040
gggccttggt atacctaaat ctagataatg caatctctgg gacaaatttt cactgtaaag   2100
ccaacccact tttacaagac gtcatatacg aagctgctaa gctcacggaa tttaatgggc   2160
acgaagactg gtcattgttc gaccattgga aatacacttc taatgccact atttctctac   2220
ttgatgggtt gtctagttac acttcatttc agtaccatct tggagtgccc gctgcacatt   2280
ttcagtttaa tgccaatgat acttcaggcg cagtctatca tagtaactcc gtattcgata   2340
gcccaacttg gttggaaaaa tttaccaatt ctgactacaa gttacacaac accatggcca   2400
tgtttgtagg tttgacaacg ctgatgctga gtgaaaacga actggcaaga ttcaatacac   2460
atgtttacct gaagaaaata tataactggt atatcgcatg gcactctaat ctatcttcag   2520
catttcccca ggacgatgaa gtgaacagct tagcaaaaag ggttctggac ttattaaaag   2580
ttgccacaca ggaagatagc atccaatttg accaacaaaa tgatattctc tataaagagt   2640
gtagggaagc tttacctgtt tgggcttttt acaaaaaaat caagagctat attaaactgc   2700
aacgatccaa tagcaaatca aagcaaattg atcaattatt tattacacac agaggactga   2760
aagacaggga atggatgaag tactctcttt tagcacctag taagtttgag ggatctgtcg   2820
gggaagtttt gccggccttt cacgaaggat tggctgatat tgatagaaac gaggtcattc   2880
agtggttaac cattttgcta agccaattca gcaacgttcg ctatttactt caataagcat   2940
ttaagtacct cacctcagta tatacattta ttttatttgc atacgtagag tgactttgaa   3000
taataaccat gagaggcttt tttgtatata ctctataaac atggcttcaa tttcttatac   3060
atgtcacacc gtacgttgtg cgaggtgatt aggaaaagta aagggggact agaagaatca   3120
```

-continued

```
tgaaatgatt tgtagataca gttatttgag gaaagcaaaa attaccaatt caggaaggtg    3180
tagggacgtc gataggagat cacatcgtta attagtgtta ggaagaatga gtttagagga    3240
tacattagcc aacatgtcat tatatgacgc caagaaatat tttcgtaaag ctcaaaatgt    3300
tgttttcaat tatactgaga tggaggggaa agttcgtgaa gcgacaaaca acgagccttg    3360
gggtgcctca tccactttaa tggaccagat ttctcaagga acttacaatt tcagggaaag    3420
agaagaaatt ttgtcc                                                   3436
```

<210> SEQ ID NO 4
<211> LENGTH: 830
<212> TYPE: PRT
<213> ORGANISM: Saccharomyces cerevisiae

<400> SEQUENCE: 4

```
Met Ala Ile Lys Ser Leu Glu Ser Phe Leu Phe Glu Arg Gly Leu Val
1               5                   10                  15

Gly Ser Tyr Ala Ile Glu Ala Leu Asn Asn Cys Thr Leu Gly Ile Asp
            20                  25                  30

Val Asn His Tyr Val Ser Arg Leu Leu Thr Asn Lys Arg Glu Gln Tyr
        35                  40                  45

Leu Asp Ala Ile Gly Gly Phe Pro Thr Ser Leu Lys Met Tyr Leu Glu
    50                  55                  60

Ser Asp Leu Lys Ile Phe Lys Asp Phe Asn Ile Thr Pro Ile Phe Val
65                  70                  75                  80

Phe Asn Gly Gly Leu Thr Tyr Asn Gln Leu Glu Ala Ser Gly His Phe
                85                  90                  95

Thr Ala Ala Ser Ala Ser Ala Ser Ile Ser Ser Thr Thr Ser Ser
            100                 105                 110

Ser Gly Thr Asn Ala Thr Thr Arg Ser Asn Thr Glu Ser Val Leu Leu
        115                 120                 125

Gln Arg Ser Arg Gly Trp Thr Gln Trp Asn Asn Leu Ile Ser Ser Asn
    130                 135                 140

Gln Asn Ser Tyr Ile Asp Gln Pro Ile Gln Pro Gln Glu Pro Phe Arg
145                 150                 155                 160

His Asn Thr Thr Ile Asp Ser Lys Ala Tyr Gln Asn Asp Leu Ile Ala
                165                 170                 175

Tyr Phe Ile Glu His Gly Tyr Met Tyr Gln Val Ala Pro Tyr Ser Ser
            180                 185                 190

Trp Phe Gln Leu Ala Tyr Leu Leu Asn Ser Ala Tyr Ile Asp Ala Ile
        195                 200                 205

Tyr Gly Pro Thr Asp Cys Leu Met Leu Asp Cys Val Asp Arg Phe Ile
    210                 215                 220

Leu Gly Met Glu Phe Pro Asn Lys Glu Phe Arg Phe Ile Asp Arg Ser
225                 230                 235                 240

Arg Val Met Lys Asp Leu Gly Cys Thr His Glu Glu Phe Ile Asp Ile
                245                 250                 255

Ala Met Ala Val Gly Asn Asp Leu Gln Pro Thr Thr Leu Pro Pro Leu
            260                 265                 270

Gln Ile Tyr Pro Val Pro Gln Leu Phe Asp Ile Ala Leu Glu Met Val
        275                 280                 285

Leu Asn Thr Gly Thr Asn Phe Tyr Ala Tyr Gln Leu Ser Thr Thr Leu
    290                 295                 300

Gln Asn Asp Ser Lys Glu Asn Ile Gln Asn Tyr Gln Arg Gly Ile Ser
```

```
            305                 310                 315                 320
    Ala Leu Arg Tyr Met Pro Val Leu Lys Asp Thr Gly Lys Val Glu Leu
                    325                 330                 335

Phe Val Gln Glu Ile Val Val Ser Glu Asp Ser Glu Lys Asn Asn
                    340                 345                 350

Lys Asp Gly Lys Lys Ser Asn Leu Ser Ser Pro Ser Ser Ala Ser Ser
                    355                 360                 365

Ser Ala Ser Pro Ala Thr Thr Val Thr Lys Asn Ala Ser Glu Lys Leu
            370                 375                 380

Thr Tyr Glu Lys Ser Ser Thr Lys Glu Val Arg Lys Pro Arg Asp Ile
    385                 390                 395                 400

Pro Asn Asp Val His Asp Phe Ile Gly Gln Met Leu Pro His Glu Tyr
                    405                 410                 415

Tyr Phe Tyr Arg Ser Ile Gly Leu Val Thr Gly Lys Leu Phe Asp Ala
                    420                 425                 430

Ile Val Thr Gly Val Tyr Pro Glu Glu Pro Leu Gly Gly Gly Ser
            435                 440                 445

Ser Thr Ser Tyr Arg Lys Leu Val Ser Lys Ser Val Glu Ile Phe Lys
            450                 455                 460

Asn Lys Glu Ile Asn Leu Leu Thr Gln Pro Ile Asn Arg Tyr Tyr Gln
    465                 470                 475                 480

Ile Lys Gln Ile Lys Gln Val Lys Trp Tyr Ala Ala Asn Glu Pro Thr
                    485                 490                 495

Thr Leu Thr Asn Arg Met Ser Pro Ser Met Phe Glu Thr Ile Asn His
                    500                 505                 510

Leu Ile Val Lys Thr Glu Thr Ser Asp Glu Lys Glu Phe Ser Ile Ser
                    515                 520                 525

Glu Phe Ile Thr Thr Ile Asn Gly Ser Ser Asn Met Ala Lys Asp Phe
                    530                 535                 540

Ile Ser Glu Lys Val Ile Phe Pro Asn Ser Val Pro Ile Glu Ser Lys
    545                 550                 555                 560

Leu Asn Ser Pro Phe Asn Leu Leu Ser Thr Asn Phe Leu Arg Leu Leu
                    565                 570                 575

Val Leu Leu Glu Phe Phe Thr Phe Asp Phe Lys Glu Lys Leu Leu Glu
                    580                 585                 590

Pro Thr Arg Trp Gly Glu Val Phe Leu Lys Leu Asn Glu Leu Asn Ile
                    595                 600                 605

Asp Ser Lys Tyr His Glu Ser Val Ile Ile Phe Leu Val Phe Leu Lys
            610                 615                 620

Cys Asp Val Leu Lys Leu Asp Glu Glu Val Gln Pro Pro Ala Pro Ser
    625                 630                 635                 640

Ala Leu Ser Gln Ala Thr Leu Arg Ser Tyr Pro Glu Glu Ser Leu Tyr
                    645                 650                 655

Val Leu Leu Ile Thr Arg Val Leu Thr Leu Phe Gln Val Asp Gln Lys
                    660                 665                 670

Pro Ser Asn Tyr His Gly Pro Ile Asp Lys Lys Thr Leu Ile Phe Arg
                    675                 680                 685

Asp His Leu Ser Phe Ile Lys Glu Asn Leu Asn Glu Leu Phe Glu Ala
                    690                 695                 700

Val Leu Ile Ser Ser Leu Thr Ser Gly Glu Phe Asn Arg Leu Ser Leu
    705                 710                 715                 720

Asp Asn Phe Gly Trp Ala Arg Lys Ile Val Arg Tyr Leu Pro Phe Lys
                    725                 730                 735
```

-continued

```
Leu Asp Ser Pro Asn Thr Ile Met Ala Met Met Trp Glu Phe Phe Leu
                740                 745                 750

Gln Lys Tyr Leu His Asn Gly Asn Ala Lys Asn Asp Ala Leu Ser Leu
            755                 760                 765

Val Ala Thr Glu Phe Asn Thr Tyr Lys Ser Thr Pro Asn Leu Asp Glu
        770                 775                 780

Gln Phe Val Glu Ser His Arg Phe Leu Leu Glu Ile Ser Lys Val Met
785                 790                 795                 800

Gln Glu Leu Asn Ala Ala Lys Leu Ile Asp Glu Asn Val Phe Lys Leu
                805                 810                 815

Phe Thr Lys Ala Val Glu Phe Thr Thr Thr Ala Leu Ser Ser
            820                 825                 830
```

<210> SEQ ID NO 5
<211> LENGTH: 2627
<212> TYPE: DNA
<213> ORGANISM: Saccharomyces cerevisiae

<400> SEQUENCE: 5

```
ctctgtctgc tcttctaacg ccagcgactt agacatgtcc ctcttatcta ctccttcaag      60
tctcttccag atggcaggtg agaccaaaag caatcctata attatacccg acagtcaaga    120
cgatagtata cttagtagcg accccttta  agtaggtaac cccctggat  tgcatagcca    180
ttgcatagcc ttagacatca aactttattt aatgacatta tccttctatg tatctttttt    240
ccccgctcga tttcttctag aacattacgg aaaataaagg aaaaaaatga ctggagcatc    300
gaatctgtag actaaaaagg taatgacgcg ttcttcgttc ccacaagtat gtgaaatcgt    360
ttgaacgctt ttatatactg ataggaatag attataatag tattcaacat tcatcaaaca    420
gtttatatcg gtaataaacc aacctcacga tacagtgatt atttctctaa acaacacgag    480
ccgtactgta cctacgataa agtaaaacgc attttctttt tgctaccagt ggacacaaga    540
taacggagaa tgcaacaaaa tacgtcttta tatgactctt tgaacgttac tgccgctgca    600
tccacatctg agattaagaa agcttacagg aacgctgcat taaatatca  tcctgataaa    660
aacaatcata cagaagaatc caagcgaaag ttccaagaga tatgccaggc atacgaaata    720
cttaaagaca atcgcttaag agctttgtat gaccagtacg gtaccacaga tgaagtcctg    780
attcaagagc agcaggcgca ggcgcaacgc caacaagccg ggccgttcag ttcatcctca    840
aatttcgata cggaagcaat gtcattcccg gatctatctc caggtgatct tttcgcgcag    900
ttttttaata gttctgctac cccctcttct aatggctcca aaagcagttt taattttagc    960
ttcaataata gctctacgcc gagtttctcc tttgttaatg gcagtggcgt gaacaatctg   1020
tactcctcgt cagcaaaata caactccaac gatgaggacc atcatttgga tagaggccct   1080
gatatcaaac ataatctaaa gtgcacattg aaggaactct acatgggtaa gactgcaaag   1140
ttgggtttga ataggacaag gatttgcagt gtttgtgatg gcacggtgg  tctaaagaaa   1200
tgcacttgta aaacatgcaa agggcaaggt attcaaaccc aaactaggcg tatgggacct   1260
ctagtacaaa gttggtctca aacttgtgca gattgcgggg gtgccggggt tttgtcaaa    1320
aataaagata tttgccaaca gtgccaaggt cttggcttca ttaaggagag gaagattcta   1380
caagtcaccg ttcaaccggg atcgtgtcat aaccaactta tagtacttac gggcgaaggt   1440
gacgaagtta ttagtactaa gggaggcggt cacgaaaagg taataacctgg tgacgtcgtt   1500
atcaccattt tacgttttaaa agatccgaat ttccaggtta tcaactactc caatttgata   1560
```

```
tgtaagaagt gcaaaatcga cttcatgacc agtttatgtg gaggcgtagt ttatattgaa      1620
gggcacccta gcggtaagtt gatcaaactt gatattatac ctggcgagat actgaagcct      1680
ggttgtttca agactgttga ggacatgggg atgcccaagt ttatcaacgg tgttcgaagc      1740
ggtttcggtc atctatatgt caaattcgat gtgacgtatc cagagagact ggaacctgaa      1800
aatgctaaga aaatacaaaa tattctggct aatgataaat acattaaagc agaacgttcc      1860
accatggaaa ccgcagattc agactgctat tgcgatttgg agaagtcata tgacagtgtg      1920
gaagagcatg tgttaagtag ctttgaggcc cctaatttaa acaatgaagt tattgaagac      1980
gacgaccttg tgatttgat taatgaaaga gattctcgga aaaggaacaa ccgtcgattc      2040
gacgaaagta atattaataa taataatgaa acgaaacgaa ataaatattc ttcaccggta      2100
agcggttttt atgaccatga tattaatgga tattgaaggt tatatagtca tgcagtaatg      2160
ttatacattt tctattttta tttttgtat cagtactcta tctataagga cattccttt      2220 ttaagcaatg cggaaagata cgctattctt tctgtagatg gtttaccgcg gtttgggtgg      2280
taatatcatt gcagccctag tcctttagca gttttttag cgtgtaatac attgttattc      2340 atcttttct tagtgcctgc caagagatcg tgggaggtta cttaacagaa aagcaaaaaa      2400
aaaaaccgat tagaatgtgc atgccgttgt tacagagaag caagggaagt tcaccactga      2460
tcatatttct aagttcatca aaatatcgtt ttggtttcag cagtagggat ctttaaccca      2520
agtgttcatt ttctttcctt tttctttt atttgaatga tctgaacaaa aggagaaaca      2580
tatactgtac tattgcgtga aaacgaacag agcacaaccc tcaagaa                   2627

<210> SEQ ID NO 6
<211> LENGTH: 850
<212> TYPE: DNA
<213> ORGANISM: Saccharomyces cerevisiae

<400> SEQUENCE: 6
tacgaaatat gatctagctt tgatattcat tcattatata attaacaaat acattatata        60
cagggagtga caacacaaaa tatactcgtg cattgaagat gcttgatgga tatatgtatt       120
acgacataaa gcttagccat taagaatatg aacgtggctt taatttgttt atatgtggag       180
agtataatca cttgccaaag atacaagacc aaagggacgg attatgttgt acttttgctt       240
gagaaaatgt gtgaattcca cgtctatcga ttttattaag cttccttgca gttttcgcgt       300
tgtttcttgt atgctggccc ctaactggca gatgcaatgt atgtctcata ccgctataac       360
tcccaatttt tctttttaga gctatattgt cttttacgat tgctctagcg tctccttcaa       420
tcgtcattgt cgacagttca ctagctatac tcatgatttg gggttctgat agttggtgca       480
tcctcatcca agggtagaac cctaacttcg agcatatctt ttcggctgtt gttttaccta       540
tgccgtaaaa tttagaggcc agtgcgattt taatgacctc tttacctttg aaacctttac       600
ccaagatgtg aacgaccatg gttttgatgg aagacccgac ttgatttgct cttgaatcgt       660
ctcttctatt ttgaagtaac aacgtatcct agcctgatat atgaaggagt tttttaacc        720 ttaaagaaca aatatattc atttctataa tgagcgccat gtcgtcaata gggatattgt       780
atcttcagct gtcatgtaac atattaactt ccaggaatct taattgaatg attatgtagg       840
gatgatcttg                                                              850

<210> SEQ ID NO 7
<211> LENGTH: 1675
<212> TYPE: DNA
<213> ORGANISM: Saccharomyces cerevisiae
```

<400> SEQUENCE: 7

```
atttacatat actacaagtc gccagtgtaa ctcctcactg aatatgattc atacataccc      60
gtatgtatta atgtataaat gttctcagag caaattttat cgatatcttg tttgccagtg     120
gtatgcaggt ttggcaaatt ttttaccata atatccgttt atagattctg gaaccttacc     180
aactttctta ccgctaatta cttccctggc tcgctcctcc actgcctggg taaattgttc     240
cttcaactga ctcagttctc tttcgtattc aatagcttgc ttctcgagga ttttttcaat     300
gtttgtcagc tcattttcat agtccagtaa cttcctttca aatctctcta attgcaacga     360
cttcttgca gttcgtatct gaatatcttg cagtaattca aaagtggaag gcctggttct      420
taagttcaca tctatcattg aatgtattat ggcattaagc cctctagagt aatactcagg     480
gacggtgtca catttcccgt ttttaatctt agtttgtagc tcgagataat tttttgcctg     540
aaatgggggg tgcaacgaac acatctcaaa aataacacaa cctagtgacc agatgtcgga     600
tagtggggag tatggttggt ccatcaacac ttcaggcgac atgtaatatg gtgtaccgac     660
gtatgttgtg gcaaattgaa tactagtttc cagagatttg gctaacccaa aatcacctaa     720
ctttaccaca acttgactat agtccatagg gctcccccctt ttccctgaat tcactctatg     780
gtctctgtaa taattactat tcacttcctc gtgaccgtct acttgttcat taatattgta     840
atcgctatca tcatagctta agaatatatt tcctggtttc agatcacgat ggataacgat     900
gttttttgcct tttaccggtg gtttcatccg gtcatatatt gtggtcaaag ttggcaattc     960
aacaccataa tgacatttat agagcgcagt caataattgg gccaggatac cccacacaat    1020
tttttctggt atatatttat gctcctgttt gtagtgctta atcatctggg ataaatcacc    1080
cctggaacaa tattccatat aaaggtataa cacttctttt tgttcatcga agtcccagtt    1140
ataaaattct acaatatttt catgcttcaa ctgcgataga atgctacatt cagcgatcag    1200
ctgttgtctc tctttgctat tcatatggcc atatttgata tcctttctaa ccaaaagttt    1260
cttggtaggt atatggatga cttttcgtac agacccaaat gaacctctcc caatttcttc    1320
gagaacttgg tattctgacc ttggtgggtg tccctgctgc tgctgaggac tacggtattc    1380
ttggaaaaac tgtcgtctat gcatactcac acagagaatt gattcaatta tcaaatagca    1440
ctctcattga aattagtatt gtgaatcttg ctcttttcat gttatatgat ttgatattct    1500
tttgaaaagt cgcttttatt tacgtttaac ctaattagga aacgtaatga aaaaattcag    1560
aaaccttaaa aaaaaaactt ggctgtaacc tatcggaaga ctgtgccact gcaatcatgt    1620
cagatatcgt atttcagatt tattgatcta tagctagaaa catttaacaa aatgc          1675
```

<210> SEQ ID NO 8
<211> LENGTH: 1362
<212> TYPE: DNA
<213> ORGANISM: Saccharomyces cerevisiae

<400> SEQUENCE: 8

```
ccctgtagaa gcttctttgt ttacagcact tgatccatgt agccatactc gaaatttcaa      60
ctcatctgaa acttttcctg aaggttgaaa aagaatgcca taagggtcac ccgaagctta     120
ttcacgagtc agtctgactc ttgcgagaga tgaggatgta ataatactaa tctcgaagat     180
gccatctaat acatatagac atacatatat atatatatac attctatata ttcttaccca     240
gattcttga ggtaagacgg ttgggtttta tcttttgcag ttggtactat taagaacaat      300
cgaatcataa gcattgctta caagaatac acatacgaaa tattaacgat aatgtcaatt      360
```

```
acgaagactg aactggacgg tatattgcca ttggtggcca gaggtaaagt tagagacata      420
tatgaggtag acgctggtac gttgctgttt gttgctacgg atcgtatctc tgcatatgac      480
gttattatgg aaaacagcat tcctgaaaag gggatcctat tgaccaaact gtcagagttc      540
tggttcaagt tcctgtccaa cgatgttcgt aatcatttgg tcgacatcgc ccaggtaag       600 actattttcg attatctacc tgcaaaattg agcgaaccaa agtacaaaac gcaactagaa      660
gaccgctctc tattggttca caaacataaa ctaattccat tggaagtaat tgtcagaggc      720
tacatcaccg gatctgcttg aaagagtac gtaaaaacag gtactgtgca tggtttgaaa       780
caacctcaag gacttaaaga atctcaagag ttcccagaac caatcttcac cccatcgacc      840
aaggctgaac aaggtgaaca tgacgaaaac atctctcctg cccaggccgc tgagctggtg      900
ggtgaagatt tgtcacgtag agtggcagaa ctggctgtaa aactgtactc caagtgcaaa      960
gattatgcta aggagaaggg catcatcatc gcagacacta aattcgaatt cggtattgac     1020
gaaaagacca atgaaattat tctagtggac gaggtgctaa cgccagactc ctctagattc     1080
tggaacggtg cctcttataa ggtaggagaa tcccaagatt cttacgataa gcaattttta     1140
agagactggc ttactgctaa taagttgaac ggtgttaacg gcgtcaaaat gccccaagac     1200
attgtcgaca ggacaagggc caaatatata gaggcttatg aaacattgac agggtctaaa     1260
tggtctcact aacgtgattt acatatacta caagtcgcca gtgtaactcc tcactgaata     1320
tgattcatac ataccgtat gtattaatgt ataaatgttc tc                         1362

<210> SEQ ID NO 9
<211> LENGTH: 3436
<212> TYPE: DNA
<213> ORGANISM: Saccharomyces cerevisiae

<400> SEQUENCE: 9
tcgtacactg atttcttaag atggcaggac aaggatgccc tagatttgtc agcactaaat       60
gaagaacaag cacaaagggc catgacccg aataccgata taaatgagac aattcaacta       120
attgtagcgg caagtctatc ctccaaatgt ttatatttgg gtgttcaaat attgggtgat      180
gcgccaattt ggcctataat attatcgttc gctcatggtt tgcaatcaag agctatctat     240
agtgttacga aaaaagaaa cactagaata taagtccgat ttacaaatat ataatggcgg      300
ccgtctctat actatagtat ttacagaatt aaagcttaga actatcataa ctttcataat      360
ataccaccag gcttcaaaaa ggcattgttc cattcggagt ttgcttgagt ttgatggccc      420
gggtaaaaag gtttgacaag gcaaggggcc gtacttatta aaacaatttc aacatgcaca     480
attaagaatg taagagatat atgagaatga tacagagaga gagaaagaga gagaaagagg     540
aaggtcaatt aaaggagaga actgttgtta atatggcaga ccctgatgac aatgaggccg     600
aagccactgg attacaacaa tatagtggcg agaccactcg cgatgacaat gaagaaagca     660
tgaatgattc tttcactta acatccagga atagaggcag aagtaataca atatctagta     720
ttgttagtgg ttatgaaata atgaaagaac atatggacaa ggaaaagttt atgtacttga     780
ttctagcgag tctccttttg tacatgggat tgttgccgc atttgctccc aggacgtctt      840
tatcaagaga ctttcggcgg tttcactctt ccagattgac gaatgcagag gtttataggga    900 tatacttgaa ctccttgcaa caggaaaata gagcgaaaga acatgtatac aagtatgctg     960
ggtacatgag caacggagca agtgattcgt caacgtttaa atataccttg gacgagtttc    1020
tagatatggg gtacaaaccc aaagttgaaa aatattaccc atggataggt gaaccagtag    1080
acactaacgt agctcccttta gaaaatggta agtggtcta cgaagcaagc atgatcgagg    1140
```

```
atagagttaa aggtgatcct gcttctcacg ctaggaaaag gcaaaagggt ttccatcaat   1200
attcaaaaaa tggaagtgta actgctcgat acgtgttttg caattatggt agcatcagtg   1260
attacaagct acttttgaag aaaaacattg atattgaaga taaatccac atcgtacgat    1320 cgggtaaaat attacctgga ttaaaggtaa agaatgcaga actttatggc gcttccagtg   1380
tcattatata tacagaccca tttgacgatg gtaaagttac tgaggaaaat gggtttttac   1440
actatcctta tggaccagca agaaacccaa gttatattag gagagattct gtaaactatt   1500
tcagtgacac tccaggagat ccgacaactc cagggtatcc ctccaaggat tccgacactg   1560
aacatatgtc accggtaggg agagtgccga ggataccatc ggtgccgatg agtgctagag   1620
atgtccaacc aattttagaa agattgaatg gcaggggttt tcaaattggg cccggtagta   1680
atataaaaga ttttggatca ttcactggac cttcaagctc tatcgataaa gtccatttgc   1740
ataatgagct aacttacaac atcaaggaaa tgagtagtgt agaggttagt atccctggta   1800
tattcactga gggggagatt attatcgag ctcataggga ttcgctcgcc tcgagtagcg    1860
ccggtgatgc aaatagtggc agcgctattc ttttagaaat tgcacgagga atgagtaaat   1920
tacttaagca tggttggaag ccactgcgtc ctatcaaact aataagttgg gatggtgaac   1980
gatccggcct tctgggatct acagattatg cagaagctca tgctgcgatt ctcaggagaa   2040
gggccttggt atacctaaat ctagataatg caatctctgg gacaaatttt cactgtaaag   2100
ccaacccact tttacaagac gtgatatacg aagctgctaa gctcacggaa tttaatgggc   2160
acgaagactg gtcattgttc gaccattgga aatacacttc taatgccact atttctctac   2220
ttgatgggtt gtctagttac acttcatttc agtaccatct tggagtgccc gctgcacatt   2280
ttcagtttaa tgccaatgat acttcaggcg cagtctatca tagtaactcc gtattcgata   2340
gcccaacttg gttggaaaaa tttaccaatt ctgactacaa gttacacaac accatggcca   2400
tgtttgtagg tttgacaacg ctgatgctga gtgaaaacga actggcaaga ttcaatacac   2460
atgtttacct gaagaaaata tataactggt atatcgcatg gcactctaat ctatcttcag   2520
catttcccca ggacgatgaa gtgaacagct tagcaaaaag ggttctggac ttattaaaag   2580
ttgccacaca ggaagatagc atccaatttg accaacaaaa tggtattctc tataaagagt   2640
gtagggaagc tttacctgtt tgggcttttt acaaaaaaat caagagctat attaaactgc   2700
aacgatccaa tagcaaatca aagcaaattg atcaattatt tattacacac agaggactga   2760
aagacaggga atggatgaag tactctcttt tagcacctag taagtttgag ggatctgtcg   2820
gggaagtttt gcccggcctt cacgaaggat tggctgatat tgatagaaac gaggtcattc   2880
agtggttaac cattttgcta agccaattca gcaacgttcg ctatttactt caataagcat   2940
ttaagtacct cacctcagta tatacattta tttatttgc atacgtagag tgactttgaa    3000
taataaccat gagaggcttt tttgtatata ctctataaac atggcttcaa tttcttatac   3060
atgtcacacc gtacgttgtg cgaggtgatt aggaaaagta aaaggggact agaagaatca   3120
tgaaatgatt tgtagataca gttatttgag gaaagcaaaa attaccaatt caggaaggtg   3180
tagggacgtc gataggagat cacatcgtta attagtgtta ggaagaatga gtttagagga   3240
tacattagcc aacatgtcat tatatgacgc caagaaatat tttcgtaaag ctcaaaatgt   3300
tgttttcaat tatactgaga tggagggaa agttcgtgaa gcgacaaaca acgagccttg   3360
gggtgcctca tccactttaa tggaccagat ttctcaagga acttacaatt tcagggaaag   3420
agaagaaatt ttgtcc                                                   3436
```

```
<210> SEQ ID NO 10
<211> LENGTH: 830
<212> TYPE: PRT
<213> ORGANISM: Saccharomyces cerevisiae

<400> SEQUENCE: 10

Met Ala Ile Lys Ser Leu Glu Ser Phe Leu Phe Glu Arg Gly Leu Val
1               5                   10                  15

Gly Ser Tyr Ala Ile Glu Ala Leu Asn Asn Cys Thr Leu Asp Ile Asp
            20                  25                  30

Val Asn His Tyr Val Ser Arg Leu Leu Thr Asn Lys Arg Glu Gln Tyr
        35                  40                  45

Leu Asp Ala Ile Gly Gly Phe Pro Thr Ser Leu Lys Met Tyr Leu Glu
    50                  55                  60

Ser Asp Leu Lys Ile Phe Lys Asp Phe Asn Ile Thr Pro Ile Phe Val
65                  70                  75                  80

Phe Asn Gly Gly Leu Thr Tyr Asn Gln Leu Glu Ala Ser Gly His Phe
                85                  90                  95

Thr Ala Ala Ser Ala Ser Ala Ser Ile Ser Ser Thr Thr Ser Ser
            100                 105                 110

Ser Gly Thr Asn Ala Thr Thr Arg Ser Asn Thr Glu Ser Val Leu Leu
        115                 120                 125

Gln Arg Ser Arg Gly Trp Thr Gln Trp Asn Asn Leu Ile Ser Ser Asn
    130                 135                 140

Gln Asn Ser Tyr Ile Asp Gln Pro Ile Gln Pro Gln Glu Pro Phe Arg
145                 150                 155                 160

His Asn Thr Thr Ile Asp Ser Lys Ala Tyr Gln Asn Asp Leu Ile Ala
                165                 170                 175

Tyr Phe Ile Glu His Gly Tyr Met Tyr Gln Val Ala Pro Tyr Ser Ser
            180                 185                 190

Trp Phe Gln Leu Ala Tyr Leu Leu Asn Ser Ala Tyr Ile Asp Ala Ile
        195                 200                 205

Tyr Gly Pro Thr Asp Cys Leu Met Leu Asp Cys Val Asp Arg Phe Ile
    210                 215                 220

Leu Gly Met Glu Phe Pro Asn Lys Glu Phe Arg Phe Ile Asp Arg Ser
225                 230                 235                 240

Arg Val Met Lys Asp Leu Gly Cys Thr His Glu Glu Phe Ile Asp Ile
                245                 250                 255

Ala Met Ala Val Gly Asn Asp Leu Gln Pro Thr Thr Leu Pro Pro Leu
            260                 265                 270

Gln Ile Tyr Pro Val Pro Gln Leu Phe Asp Ile Ala Leu Glu Met Val
        275                 280                 285

Leu Asn Thr Gly Thr Asn Phe Tyr Ala Tyr Gln Leu Ser Thr Thr Leu
    290                 295                 300

Gln Asn Asp Ser Lys Glu Asn Ile Gln Asn Tyr Gln Arg Gly Ile Ser
305                 310                 315                 320

Ala Leu Arg Tyr Met Pro Val Leu Lys Asp Thr Gly Lys Val Glu Leu
                325                 330                 335

Phe Val Gln Glu Ile Val Val Ser Glu Glu Asp Ser Glu Lys Asn Asn
            340                 345                 350

Lys Asp Gly Lys Lys Ser Asn Leu Ser Ser Pro Ser Ser Ala Ser Ser
        355                 360                 365

Ser Ala Ser Pro Ala Thr Thr Val Thr Lys Asn Ala Ser Glu Lys Leu
    370                 375                 380
```

```
Thr Tyr Glu Lys Ser Ser Thr Lys Glu Val Arg Lys Pro Arg Asp Ile
385                 390                 395                 400

Pro Asn Asp Val His Asp Phe Ile Gly Gln Met Leu Pro His Glu Tyr
            405                 410                 415

Tyr Phe Tyr Arg Ser Ile Gly Leu Val Thr Gly Lys Leu Phe Asp Ala
            420                 425                 430

Ile Val Thr Gly Val Tyr Pro Glu Glu Pro Pro Leu Gly Gly Gly Ser
            435                 440                 445

Ser Thr Ser Tyr Lys Lys Leu Val Ser Lys Ser Val Glu Ile Phe Lys
    450                 455                 460

Asn Lys Glu Ile Asn Leu Leu Thr Gln Pro Ile Asn Arg Tyr Tyr Gln
465                 470                 475                 480

Ile Lys Gln Ile Lys Gln Val Lys Trp Tyr Ala Ala Asn Glu Pro Thr
                485                 490                 495

Thr Leu Thr Asn Arg Met Ser Pro Ser Met Phe Glu Thr Ile Asn His
                500                 505                 510

Leu Ile Val Lys Thr Glu Thr Ser Asp Glu Lys Glu Phe Ser Ile Ser
            515                 520                 525

Glu Phe Ile Thr Thr Ile Asn Gly Ser Ser Asn Met Ala Lys Asp Phe
            530                 535                 540

Ile Ser Glu Lys Val Ile Phe Pro Asn Ser Val Pro Ile Glu Ser Lys
545                 550                 555                 560

Leu Asn Ser Pro Phe Asn Leu Ser Thr Asn Phe Leu Arg Leu Leu
                565                 570                 575

Val Leu Leu Glu Phe Phe Thr Phe Asp Phe Lys Glu Lys Leu Leu Glu
            580                 585                 590

Pro Thr Arg Trp Gly Glu Val Phe Leu Lys Leu Asn Glu Leu Asn Ile
            595                 600                 605

Asp Ser Lys Tyr His Glu Ser Val Ile Ile Phe Leu Val Phe Leu Lys
    610                 615                 620

Cys Asp Val Leu Lys Leu Asp Glu Glu Val Gln Pro Pro Ala Pro Ser
625                 630                 635                 640

Ala Leu Ser Gln Ala Thr Leu Arg Ser Tyr Pro Glu Glu Ser Leu Tyr
                645                 650                 655

Val Leu Leu Ile Thr Arg Val Leu Thr Leu Phe Gln Val Asp Gln Lys
                660                 665                 670

Pro Ser Asn Tyr His Gly Pro Ile Asp Lys Lys Thr Leu Ile Phe Arg
            675                 680                 685

Asp His Leu Ser Phe Ile Lys Glu Asn Leu Asn Glu Leu Phe Glu Ala
            690                 695                 700

Val Leu Ile Ser Ser Leu Thr Ser Gly Glu Phe Asn Arg Leu Ser Leu
705                 710                 715                 720

Asp Asn Phe Gly Trp Ala Arg Lys Ile Val Arg Tyr Leu Pro Phe Lys
                725                 730                 735

Leu Asp Ser Pro Asn Thr Ile Met Ala Met Met Trp Glu Phe Phe Leu
            740                 745                 750

Gln Lys Tyr Leu His Asn Gly Asn Ala Lys Asn Asp Ala Leu Ser Leu
            755                 760                 765

Val Ala Thr Glu Phe Asn Thr Tyr Lys Ser Thr Pro Asn Leu Asp Glu
    770                 775                 780

Gln Phe Val Glu Ser His Arg Phe Leu Leu Glu Ile Ser Lys Val Met
785                 790                 795                 800
```

Gln Glu Leu Asn Ala Ala Lys Leu Ile Asp Glu Asn Val Phe Lys Leu
805 810 815

Phe Thr Lys Ala Val Glu Phe Thr Thr Thr Ala Leu Ser Ser
820 825 830

<210> SEQ ID NO 11
<211> LENGTH: 2629
<212> TYPE: DNA
<213> ORGANISM: Saccharomyces cerevisiae

<400> SEQUENCE: 11

| | | | | | |
|---|---|---|---|---|---|
| ctctgtctgc | tcttctaacg | ccagcgactt | agacatgtcc | cttttatcta | ctccttcaag | 60 |
| tctcttccag | atggcaggtg | agaccaaaag | caatcctata | attatacccg | acagtcaaga | 120 |
| cgatagtata | cttagtagcg | accccttta | agtaggtaac | cccccctgga | ttgcatagcc | 180 |
| attgcatagc | cttagacatc | aaactttatt | taatcacatt | atccttctat | gtatcttttt | 240 |
| cccccgctcg | atttcttcta | gaacattacg | gaaaataaag | gaaaaaaatg | actggagcat | 300 |
| cgaatctgta | gactaaaaag | gtaatgacgc | gttcttcgtt | cccacaagta | tgtgaaatcg | 360 |
| tttgaacgct | tttatatact | gataggaata | gattataata | gtattcaaca | ttcatcaaac | 420 |
| agtttatatc | ggtaataaac | caacctcacg | atacagtgat | tatttctcta | aacaacacga | 480 |
| gccgtactgt | acctacgata | aagtaaaaca | cattttctt | ttgctaccag | tggacacaag | 540 |
| ataacggaga | atgcaacaaa | acacgtcttt | atatgactct | ttgaacgtta | ctgccgctgc | 600 |
| atccacatct | gagattaaga | aagcttacag | gaacgctgca | ttaaaatatc | atcctgataa | 660 |
| aaacaatcat | acagaagaat | ccaagcgaaa | gtttcaagag | atatgccagg | catacgaaat | 720 |
| acttaaagac | aatcgtttaa | gagctttgta | tgaccagtac | ggtaccacag | atgaagtcct | 780 |
| gattcaagag | cagcaggcgc | aggcgcaacg | ccaacaagcc | gggccgttca | gttcatcctc | 840 |
| aaatttcgat | acggaagcaa | tgtcattccc | ggatctatct | ccaggtgatc | ttttcgcgca | 900 |
| gttttttaat | agttctgcta | ccccctcttc | taatggctcc | aaaagcagtt | ttaattttag | 960 |
| cttcaataat | agctctacgc | cgagcttctc | ctttgttaat | ggcagtggcg | tgaacaatct | 1020 |
| gtactcctcg | tcagcaaaat | acaactccaa | cgatgaggac | catcatttgg | atagaggccc | 1080 |
| tgatatcaaa | cataatctaa | agtgcacatt | gaaggaactc | tacatgggta | agactgcaaa | 1140 |
| gttgggtttg | aataggacaa | ggatttgcag | tgtttgtgat | gggcacggtg | gtctaaagaa | 1200 |
| atgcacttgt | aaaacatgca | aagggcaagg | tattcaaacc | caaactaggc | gtatgggacc | 1260 |
| tctagtacaa | agttggtctc | aaacttgtgc | agattgcggg | ggtgccgggg | ttttgtcaa | 1320 |
| aaataaagat | atttgccaac | agtgccaagg | tcttggcttc | attaaggaga | ggaagattct | 1380 |
| acaagtcacc | gttcaaccgg | gatcgtgtca | taaccaactt | atagtactta | cgggcgaagg | 1440 |
| tgacgaagtt | attagtacta | agggaggcgg | tcacgaaaag | gtaatacctg | gtgacgtcgt | 1500 |
| tatcaccatt | ttacgtttaa | aagatccgaa | tttccaggtt | atcaactact | ccaatttgat | 1560 |
| atgtaagaag | tgcaaaatcg | acttcatgac | cagtttatgt | ggaggcgtag | tttatattga | 1620 |
| agggcaccct | agcggtaagt | tgatcaaact | tgatattata | cctggcgaga | tactgaagcc | 1680 |
| tggttgtttc | aagactgttg | aggacatggg | gatgcccaag | tttatcaacg | tgttcggag | 1740 |
| cggtttcggt | catctatatg | tcaaattcga | tgtgacgtat | ccagagagac | tggaacctga | 1800 |
| aaatgctaag | aaaatacaaa | atattctggc | taatgataaa | tacattaaag | cagaacgttc | 1860 |
| caccatggaa | accgcagatt | cagactgcta | ttgcgatttg | gagaagtcat | atgacagtgt | 1920 |
| ggaagagcat | gtgttaagta | gctttgaggc | ccctaattta | aacaatgaag | ttattgaaga | 1980 |

```
cgacgaccTT ggtgatttga ttaatgaaag agattctcgg aaaaggaaca accgtcgatt    2040
cgacgaaagt aatattaata ataataatga aacgaaacga aataaatatt cttcaccggt    2100
aagcggtttt tatgaccatg atattaatgg atattgaagg ttatatagtc atgcagtaat    2160
gttatacatt ttctattttt attttttgta tcagtactct atctataagg acattccttt    2220
ttttaagcaa tgcggaaaga tacgctattc ttcctgtgga tggtttaccg cggtttgggt    2280
ggtaatatca ttgcagccct agtcctttag cagttttttt agcgtgtaat acattgttat    2340
tcatcttttt cttagtgcct gccaagagat cgtgggaggt tacttaacag aaaagcaaaa    2400
aaaaaaaccg attagaatgt gcatgccgtt gttacagaga agcaagggaa gttcaccact    2460
gatcatattt ctaagttcat caaaatatcg ttttggtttc agcagtaggg atctttaacc    2520
caagtgttca ttttcttttcc ttttttgcttt ttatttgaat gatctgaaca aaaggagaaa    2580
catatactgt actattgcgt gaaaacgaac agagcacaac cctcaagaa                 2629

<210> SEQ ID NO 12
<211> LENGTH: 857
<212> TYPE: DNA
<213> ORGANISM: Saccharomyces cerevisiae

<400> SEQUENCE: 12
tacgaaatat gatctagctt tgatattcat tcattatata attaacaaat acattatata      60
cagggagtga caacacaaaa tatactcgtg cattcaagat gcttgatgga tatatgtatt     120
acgacataaa gcttagccat taagaatatg aacgtggctt taatttgttt atatgtggag     180
agtataatca cttgccaaag atacaagacc aaagggacgg attatgttgt acttttgctt     240
gagaaaatgt gtgaattcca cgtctatcga ttttattaag cttccttgca gttttcgcgt     300
tgtttcttgt atgctggccc ctaactggca gatgcaatgt atgtctcata ccgctataac     360 tcccaattt tcttttttaga gctatattgt cttttacgat tgctctagcg tctccttcaa     420
tcgtcattgt cgacagttca ctagctatac tcatgatttg gggttctgat agttggtgca     480
tcctcatcca agggtagaac cctaacttcg agcatatctt ttcggctgtt gttttaccta     540
tgccgtaaaa tttagaggcc agtgcgattt taatgacctc tttacctttg aaaccttttcc    600 ccaagatgtg aacgaccatg gttttgatgg aagacccgac ttgatttgct cttcaatcgt     660
ctcttctatt ttgaagtaac aacgtatcct agcctgatat atgaaggagt ttttaacct     720 taaagaacag atatatttca tttctataat gagcgccatg tcgtcaatag ggatattgta    780
tcttcagctg tcatgtaaca tattaactcc caggaatctt aattgagaac ttgaatgatt    840
atgtagggat gatcttg                                                    857
```

YEAST ALLELES INVOLVED IN MAXIMAL ALCOHOL ACCUMULATION CAPACITY AND TOLERANCE TO HIGH ALCOHOL LEVELS

CROSS-REFERENCE TO RELATED APPLICATIONS

This application is a national phase entry under 35 U.S.C. § 371 of International Patent Application PCT/EP2014/057629, filed Apr. 15, 2014, designating the United States of America and published in English as International Patent Publication WO 2014/170330 A2 on Oct. 23, 2014, which claims the benefit under Article 8 of the Patent Cooperation Treaty and under 35 U.S.C. § 119(e) to European Patent Application Serial No. 13163727.4, filed Apr. 15, 2013.

TECHNICAL FIELD

The disclosure relates to biotechnology generally, and more specifically to a specific yeast allele of KIN3 that is involved in maximal alcohol accumulation and/or in tolerance to high alcohol levels. Preferably, the alcohol is ethanol. In a preferred embodiment, this specific allele is combined with specific alleles of ADE1 and/or VPS70. More specifically, the disclosure relates to the use of these alleles for the construction and/or selection of high alcohol tolerant yeasts, by stacking of positive alleles, or the selection and construction of low alcohol producing yeasts by stacking of negative alleles.

BACKGROUND

The capacity to produce high levels of alcohol is a very rare characteristic in nature. It is most prominent in the yeast *Saccharomyces cerevisiae*, which is able to accumulate in the absence of cell proliferation, ethanol concentrations in the medium of more than 17%, a level that kills virtually all competing microorganisms. As a result, this property allows this yeast to outcompete all other microorganisms in environments rich enough in sugar to sustain the production of such high ethanol levels (Casey and Ingledew, 1986; D'Amore and Stewart, 1987). Very few other microorganisms, e.g., the yeast *Dekkera bruxellensis*, have independently evolved a similar but less pronounced ethanol tolerance compared to *S. cerevisiae* (Rozpedowska et al., 2011). The capacity to accumulate high ethanol levels lie at the basis of the production of nearly all alcoholic beverages as well as bioethanol in industrial fermentations by the yeast *S. cerevisiae*. Originally, all alcoholic beverages were produced with spontaneous fermentations in which *S. cerevisiae* gradually increases in abundance, in parallel with the increase in the ethanol level, to finally dominate the fermentation at the end.

The genetic basis of yeast alcohol tolerance, particularly ethanol tolerance has attracted much attention but until recently nearly all research was performed with laboratory yeast strains, which display much lower alcohol tolerance than the natural and industrial yeast strains. This research has pointed to properties like membrane lipid composition, chaperone protein expression and trehalose content, as major requirements for ethanol tolerance of laboratory strains (D'Amore and Stewart, 1987; Ding et al., 2009) but the role played by these factors in other genetic backgrounds and in establishing tolerance to very high ethanol levels has remained unknown. We have recently performed polygenic analysis of the high ethanol tolerance of a Brazilian bioethanol production strain VR1. This revealed the involvement of several genes previously never connected to ethanol tolerance and did not identify genes affecting properties classically considered to be required for ethanol tolerance in lab strains (Swinnen et al., 2012a).

A second shortcoming of most previous studies is the assessment of alcohol tolerance solely by measuring growth on nutrient plates in the presence of increasing alcohol levels. (D'Amore and Stewart, 1987; Ding et al., 2009). This is a convenient assay, which allows hundreds of strains or segregants to be phenotyped simultaneously with little work and manpower. However, the real physiological and ecological relevance of alcohol tolerance in *S. cerevisiae* is its capacity to accumulate by fermentation high alcohol levels in the absence of cell proliferation. This generally happens in an environment with a large excess of sugar compared to other essential nutrients. As a result, a large part of the alcohol in a typical, natural or industrial, yeast fermentation is produced with stationary phase cells in the absence of any cell proliferation. The alcohol tolerance of the yeast under such conditions determines its maximal alcohol accumulation capacity, a specific property of high ecological and industrial importance. In industrial fermentations, a higher maximal alcohol accumulation capacity allows a better attenuation of the residual sugar and, therefore, results in a higher yield. A higher final alcohol titer reduces the distillation costs and also lowers the liquid volumes in the factory, which has multiple beneficial effects on costs of heating, cooling, pumping and transport of liquid residue. It also lowers microbial contamination and the higher alcohol tolerance of the yeast generally also enhances the rate of fermentation especially in the later stages of the fermentation process. Maximal alcohol accumulation capacity can only be determined in individual yeast fermentations, which are much more laborious to perform than growth tests on plates. In static industrial fermentations, maintenance of the yeast in suspension is due to the strong $CO_2$ bubbling and this can only be mimicked in lab scale with a sufficient amount of cells in a sufficiently large volume.

The advent of high-throughput methods for genome sequencing has created a breakthrough also in the field of quantitative or complex trait analysis in yeast (Liti and Lewis, 2012; Swinnen et al., 2012b). The new methodology has allowed efficient QTL mapping of several complex traits (Swinnen et al., 2012a; Ehrenreich et al., 2010; Parts et al., 2011) and reciprocal hemizygosity analysis (Steinmetz et al., 2002) has facilitated identification of the causative genes. The efficiency of the new methodologies calls for new challenges to be addressed, such as comparison of the genetic basis of related complex properties. In addition, complex trait analysis in yeast has been applied up to now mainly to phenotypic properties that are easy to score in hundreds or even thousands of segregants (Swinnen et al., 2012a; Ehrenreich et al., 2010; Parts et al., 2011; Steinmetz et al., 2002; Winzeler et al., 1998; Deutschbauer and Davis, 2005; Brem et al., 2002; Marullo et al., 2007; Nogami et al., 2007; Perlstein et al., 2007). However, many phenotypic traits with high ecological or industrial relevance require more elaborate experimental protocols for assessment and it is not fully clear yet whether the low numbers of segregants that can be scored in these cases are adequate for genetic mapping with pooled-segregant whole-genome sequence analysis.

BRIEF SUMMARY

Surprisingly, we found that a KIN3 allele can modulate alcohol tolerance and/or accumulation: one specific allele allows a higher alcohol accumulation, while another specific allele of the same KIN3 gene results in lower alcohol accumulation. The forms can be combined with other specific alleles, from other genes, to obtain a maximal or minimal alcohol accumulation, depending upon the use of the strain.

One aspect of the disclosure is the use of a KIN3 allele to modulate alcohol accumulation and/or alcohol tolerance in yeast. Alcohol, as used herein, includes higher alcohols such as isobutanol. Preferably, the alcohol is ethanol. Preferably, the yeast is a *Saccharomyces* spp., such as, but not limited to, *Saccharomyces cerevisiae*. The KIN3 allele may be combined with other alleles that allow modulation of alcohol accumulation and/or alcohol tolerance. As a non-limiting example, the alleles are selected from the group of genes consisting of ADE1, VPS70, MKT1, APJ1 and SWS2. In one preferred embodiment, the modulation is an increase in alcohol tolerance and/or alcohol accumulation. As a non-limiting example, an increase in alcohol tolerance and/or accumulation may be favorable for bio-ethanol production. Preferably, in order to obtain an increase in alcohol tolerance and/or alcohol accumulation, the KIN3 allele consists of SEQ ID NO:1. Preferably, the KIN3 allele, consisting of SEQ ID NO:1 is combined with specific alleles selected from the group of genes consisting of ADE1, VPS70, MKT1, APJ1 and SWS2. In one preferred embodiment, the specific APJ1 allele is an inactive allele, such as a deletion of the gene. In another preferred embodiment, the SWS2 allele is overexpressing the SWS2 protein. Even more preferably, the KIN3 allele is combined with specific alleles selected from the group consisting of SEQ ID NO:2 (ADE1), SEQ ID NO:3 (VPS70), SEQ ID NO:5 (APJ1), SEQ ID NO:6 (SWS2) and a nucleic acid encoding SEQ ID NO:4 (MKT1). A preferred embodiment is the combination of SEQ ID NO:3 with SEQ ID NO:4, preferably in combination with the KIN3 allele.

In another preferred embodiment, the modulation is a decrease in alcohol tolerance and/or alcohol accumulation. As a non-limiting example, a decrease in ethanol accumulation is wanted in the production of wine, produced from grapes in a warm climate, as the high sugar content of the grapes may result in unwanted ethanol concentrations of 15% or more. Preferably, in order to obtain a decrease in alcohol tolerance and/or alcohol concentration, the KIN3 allele consists of SEQ ID NO:7. Even more preferably, the KIN3 allele, consisting of SEQ ID NO:7 is combined with specific alleles selected from the group of ADE1, VPS70, MKT1, APJ1 and SWS2. Even more preferably, the KIN3 allele is combine with specific alleles selected from the group consisting of SEQ ID NO:8 (ADE1), SEQ ID NO:9 (VPS70), SEQ ID NO:11 (APJ1), SEQ ID NO:12 (SWS2) and a nucleic acid encoding SEQ ID NO:10 (MKT1).

Another aspect of the disclosure is the use of a KIN3 allele for selecting a yeast strain with a higher or lower alcohol tolerance and/or alcohol accumulation. In one preferred embodiment, SEQ ID NO:1 is used for selecting a yeast strain with a higher alcohol tolerance and/or accumulation. In another preferred embodiment, SEQ ID NO:7 is used for selecting a yeast strain with a lower alcohol tolerance and/or accumulation. Preferably, the yeast is a *Saccharomyces* spp. The selection of the strain can be carried out with every method known to the person skilled in the art. As a non-limiting example, strains may be selected on the base of an identification of the allele by PCR or hybridization. The selection may be combined by a selection for other alleles, known to be involved in alcohol accumulation and/or alcohol tolerance, such as, but not limited to, specific alleles of ADE1, VPS70, MKT1, APJ1 or SWS2. The selection may be carried out simultaneously or consecutively. In case of a consecutive selection the sequence of the selection is not important, i.e., the selection using KIN3 may be carried out before or after the other selection rounds.

DEFINITIONS

The following definitions are set forth to illustrate and define the meaning and scope of various terms used to describe the disclosure herein.

An allele, as used herein, is a specific form of the gene, which is carrying SNP's or other mutations, either in the coding (reading frame) or the non-coding (promoter region, or 5' or 3' non-translated end) part of the gene, wherein the mutations distinguish the specific form from other forms of the gene.

An inactive APJ1 allele, as used herein, means that, in a haploid strain the APJ1 gene is replaced by the inactive or inactivated allele, and in a diploid or polyploidy or aneuploid yeast strain, at least one copy of the APJ1 gene is replaced by the inactive allele. Preferably, several copies are replaced; most preferably all copies are replaced by the inactivated allele. Preferably, the inactive allele is a disrupted or deleted apj1 mutant, including the complete deletion of the gene.

Overexpression of SWS2 protein, as used herein, means that the amount of SWS2 protein in the overexpressing strain is higher than in SK1 yeast strain, when grown under the same conditions. Preferably, the overexpressing allele is compared in the same genetic background, wherein only the SWS2 allele is changed.

Gene, as used herein, includes both the promoter and terminator region of the gene as well as the coding sequence. It refers both to the genomic sequence (including possible introns) as well as to the cDNA derived from the spliced messenger, operably linked to a promoter sequence.

Coding sequence is a nucleotide sequence, which is transcribed into mRNA and/or translated into a polypeptide when placed under the control of appropriate regulatory sequences. The boundaries of the coding sequence are determined by a translation start codon at the 5'-terminus and a translation stop codon at the 3'-terminus. A coding sequence can include, but is not limited to, mRNA, cDNA, recombinant nucleotide sequences or genomic DNA, while introns may be present as well under certain circumstances.

Promoter region of a gene, as used herein, refers to a functional DNA sequence unit that, when operably linked to a coding sequence and possibly a terminator sequence, as well as possibly placed in the appropriate inducing conditions, is sufficient to promote transcription of the coding sequence.

Nucleotide sequence," "DNA sequence" or "nucleic acid molecule(s)," as used herein, refers to a polymeric form of nucleotides of any length, either ribonucleotides or deoxyribonucleotides. This term refers only to the primary structure of the molecule. Thus, this term includes double- and single-stranded DNA, and RNA. It also includes known types of modifications, for example, methylation, "caps" substitution of one or more of the naturally occurring nucleotides with an analog.

Modulation of alcohol accumulation and/or tolerance, as used herein, means an increase or a decrease of the alcohol concentration, produced by the yeast carrying the specific allele, as compared with the alcohol concentration produced under identical conditions by a yeast that is genetically identical, apart from the specific allele(s).

Alcohol, as used herein, can be any kind of alcohol, including, but not limited to, methanol, ethanol, n- and isopropanol, n- and isobutanol. Indeed, several publications indicate that the tolerance to ethanol and other alkanols is determined by the same mechanisms (Carlsen et al., 1991; Casal et al., 1998).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

(A) Distribution of relative maximal ethanol production capacity of 68 different yeast strains compared to the wine strain V1116. The semi-static fermentations were performed in 250 mL of YP+33% glucose at 25° C. The V1116 strain produced 18.4% (±0.4%) (v/v) ethanol. (B) Ethanol tolerance of cell proliferation (X-axis) and maximal ethanol accumulation capacity (Y-axis) in the 68 yeast strains. The possible correlation between the two traits was tested with a Spearman test, because of the non-normality of the ethanol accumulation trait. The (one-tailed) Spearman test indicated a weak correlation (90% confidence interval, P-value=0.0984).

Figure 2:
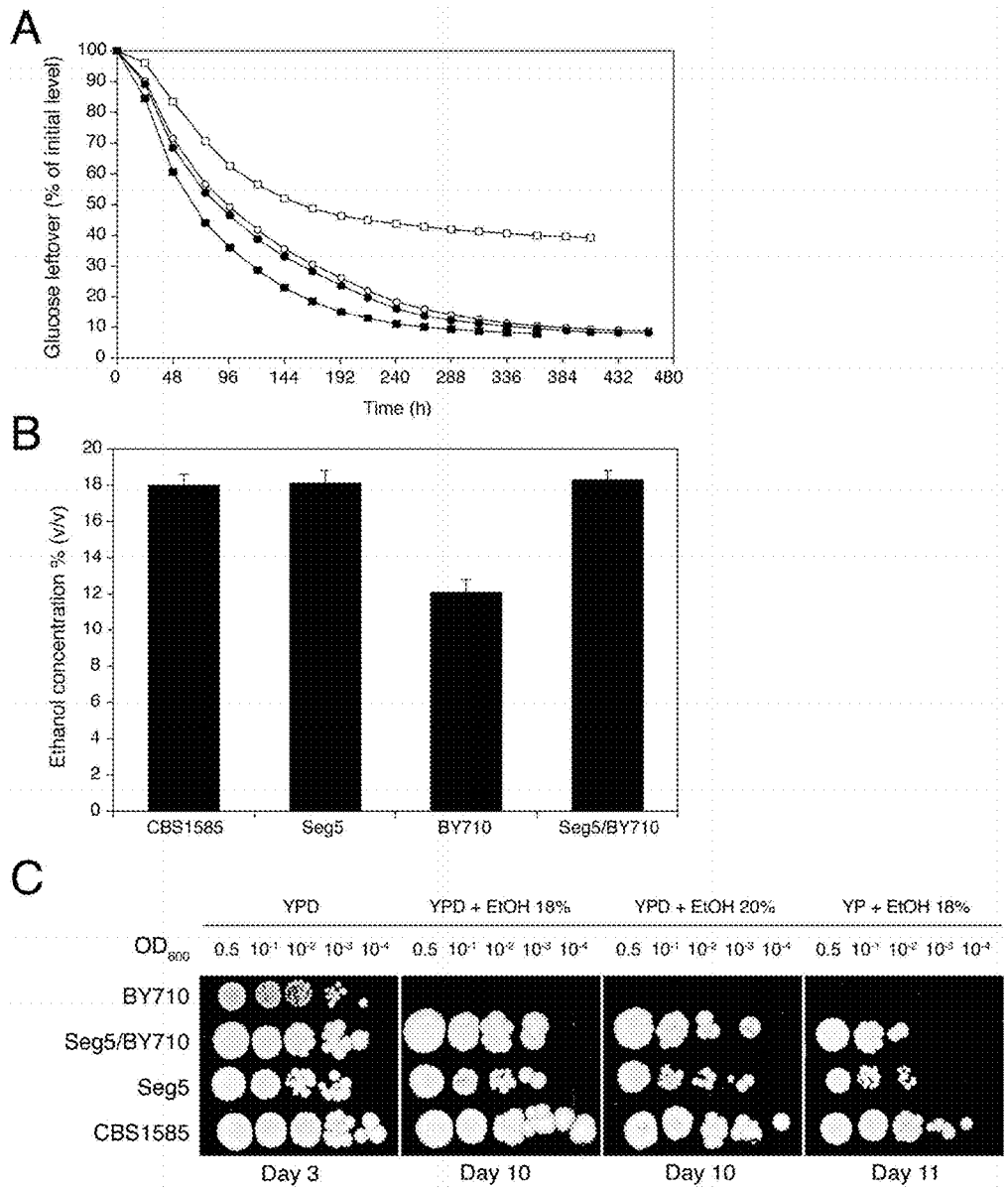

FIG. 2. Maximal ethanol accumulation capacity and ethanol tolerance of cell proliferation in the superior parent and its segregant.

(A) Identification of a segregant with the same high ethanol accumulation capacity of CBS1585. A segregant, Seg5 (n), derived from CBS1585 (2n) showed better attenuation of the fermentation medium compared to the laboratory strain BY710. The diploid (Seg5/BY710) showed similar final attenuation as the superior strains CBS1585 and Seg5. Strains: (●) Seg5, (○) CBS1585, (■) Seg5/BY710 and (□) BY710. (B) Maximal ethanol production capacity in 250 mL of YP+33% glucose at 25° C. The strains CBS1585 (2n), Seg5 (n), Seg5/BY710 (2n) showed much higher ethanol accumulation capacity compared to BY710 (n). (C) Growth assays on plates containing YP or YPD plus ethanol (18 and 20% v/v). The strains CBS1585 (2n), Seg5 (n), Seg5/BY710 (2n) showed much higher ethanol tolerance of cell proliferation compared to BY710 (n).

Figure 3:
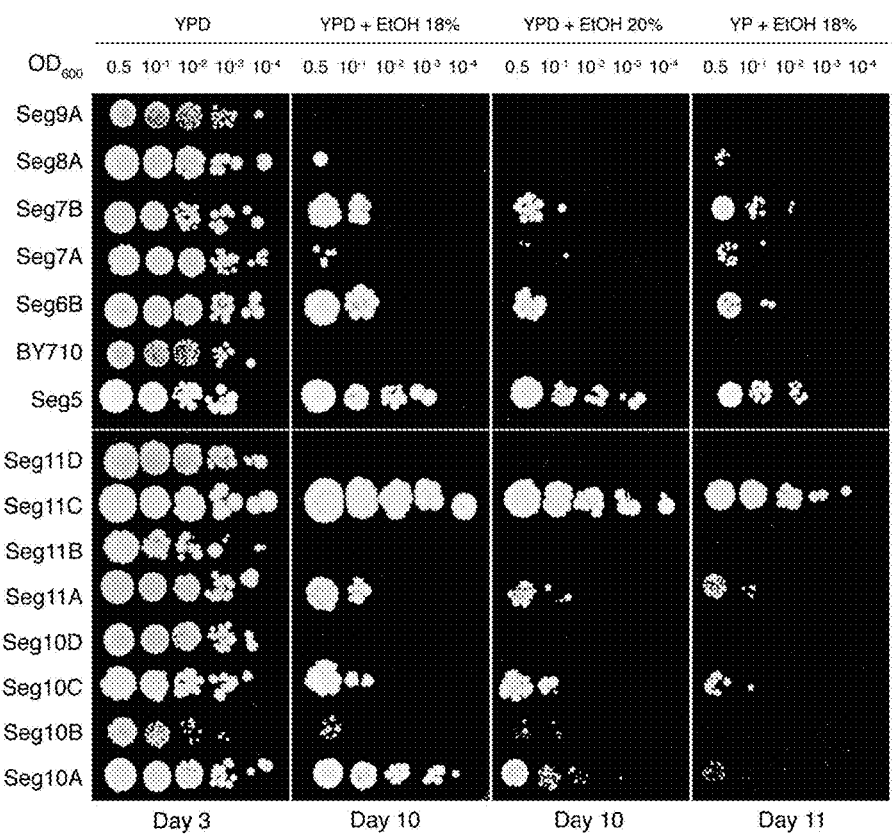
Figure 3:
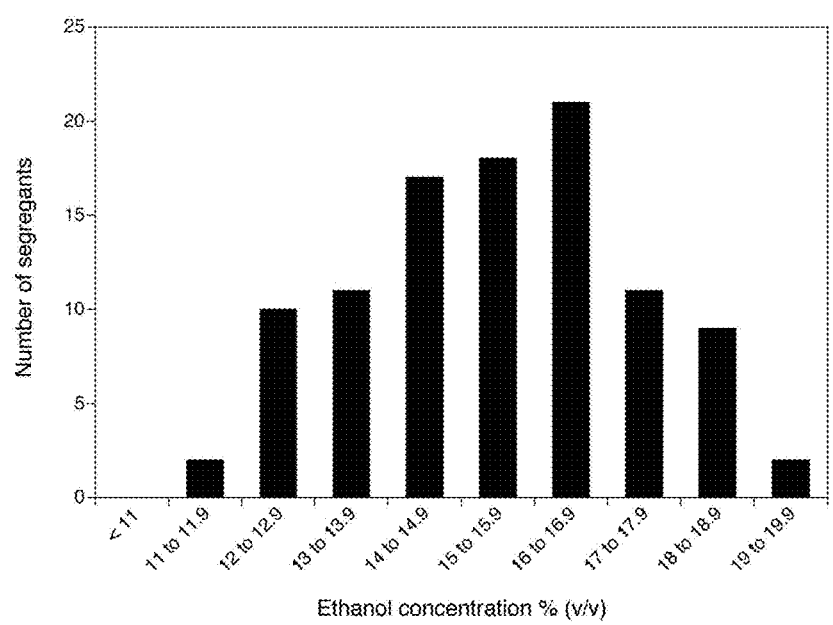

FIG. 3. Maximal ethanol accumulation capacity and ethanol tolerance of cell proliferation in meiotic segregants.

(A) Cell proliferation assays on solid media containing YP or YPD plus ethanol (18% and 20% v/v). Stationary phase cells were diluted ten-fold from OD600: 0.5 and 4 μL were spotted on the different media. Seg5 (n) showed much higher ethanol tolerance than BY710 (n) and the segregants derived from the diploid Seg5/BY710 presented different cell proliferation capacity (e.g., Seg11C showed high ethanol tolerance whereas Seg11D was ethanol sensitive). (B) Distribution of maximal ethanol production capacity within 101 meiotic segregants derived from Seg5/BY710. The semi-static fermentations were performed in 250 mL of YP+33% glucose at 25° C.

Figure 4:
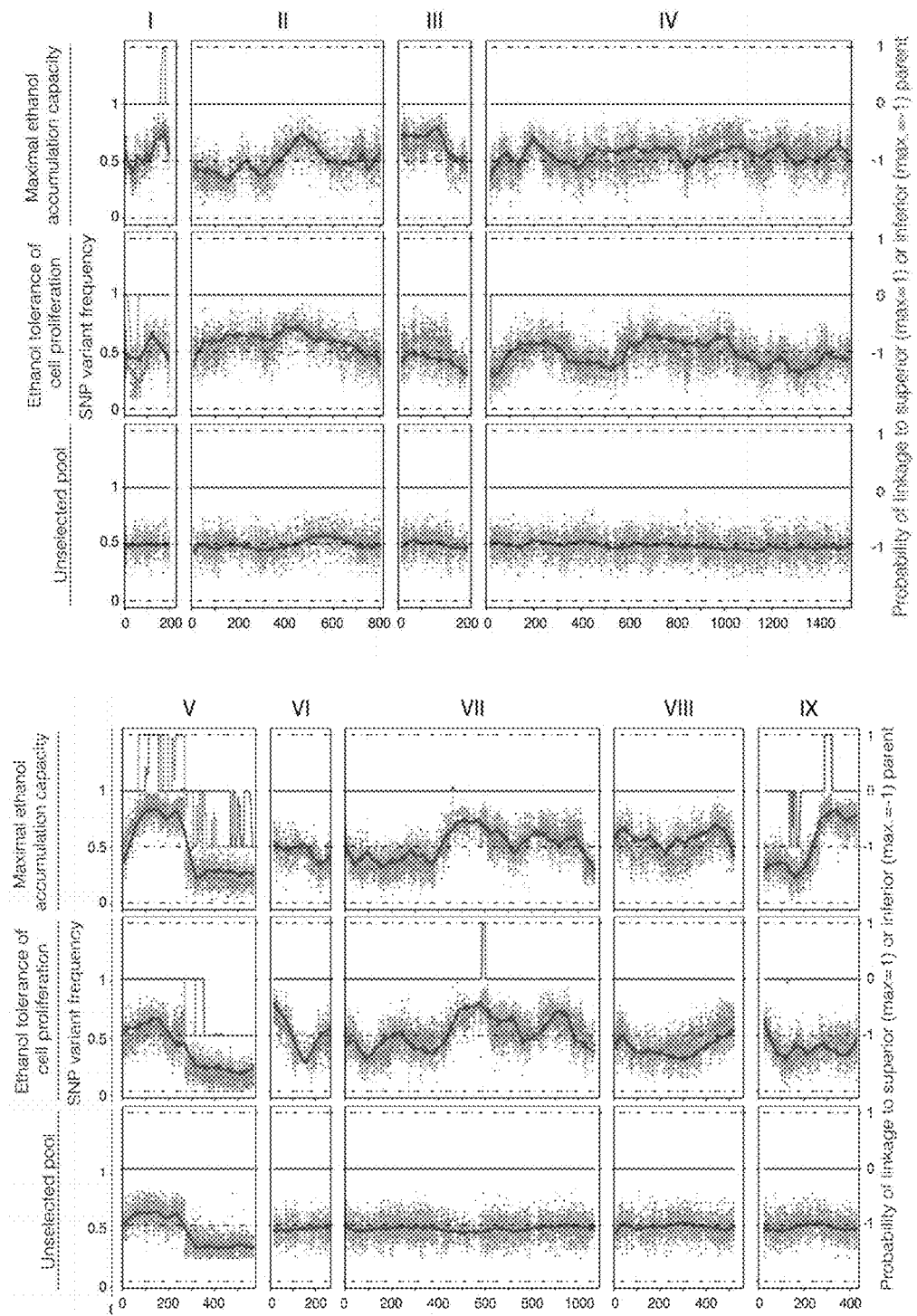
Figure 4:
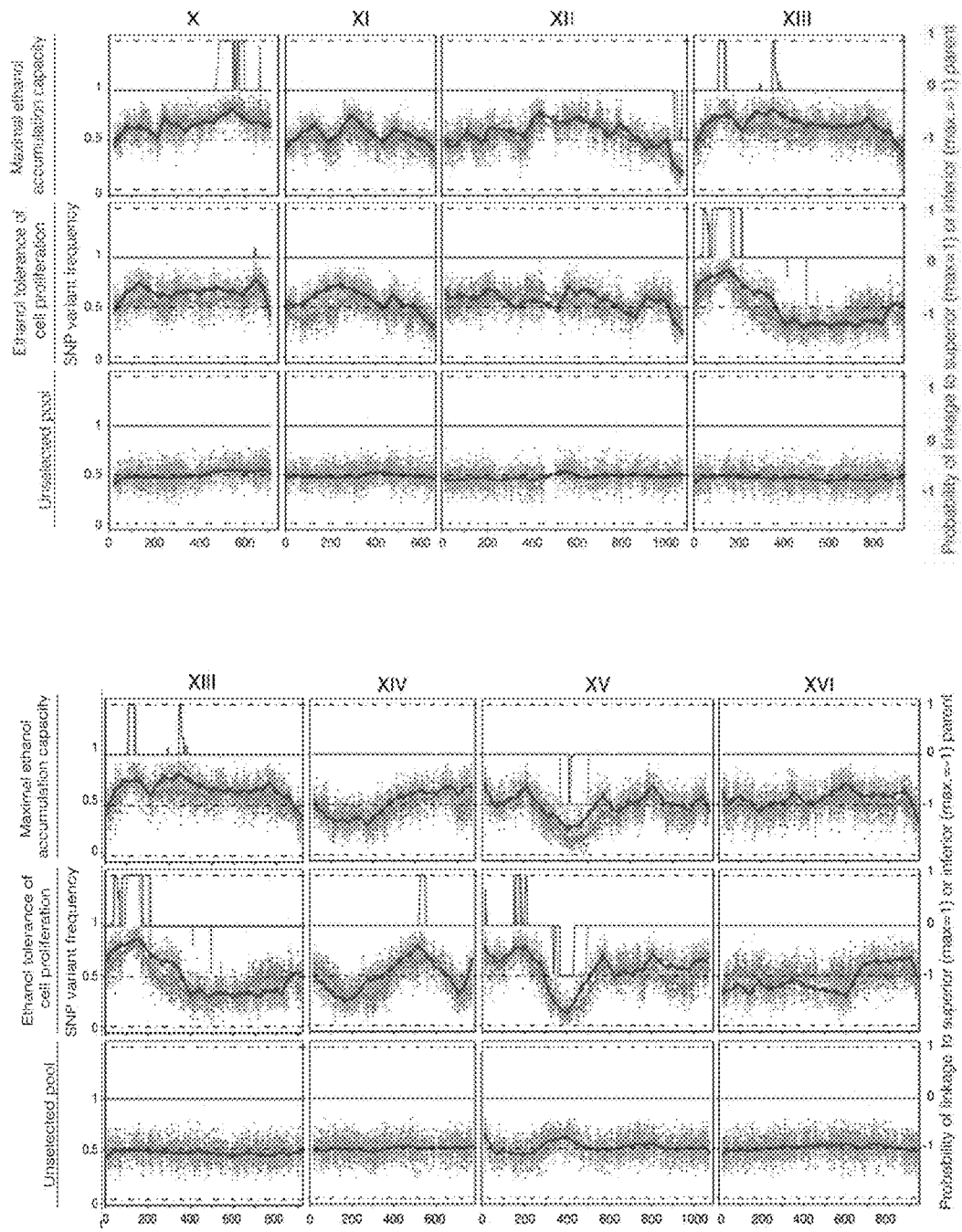

FIG. 4. QTL mapping of maximal ethanol accumulation capacity (pool 1) and high ethanol tolerance of cell proliferation (pool 2).

22 selected segregants (pool 1) with high ethanol accumulation capacity and 32 selected segregants (pool 2) with high ethanol tolerance of cell proliferation were pooled for whole genome sequencing analysis, which was performed by two independent companies utilizing the Illumina platform (BGI in green and GATC in red). An unselected pool composed of 237 segregants (pool 3) was also sequenced twice to assess proper segregation of all chromosomes and possible linkage to inadvertently selected traits. The probability of linkage to the superior or the inferior parent, as determined with the HMM, is indicated on the right.

Figure 5:
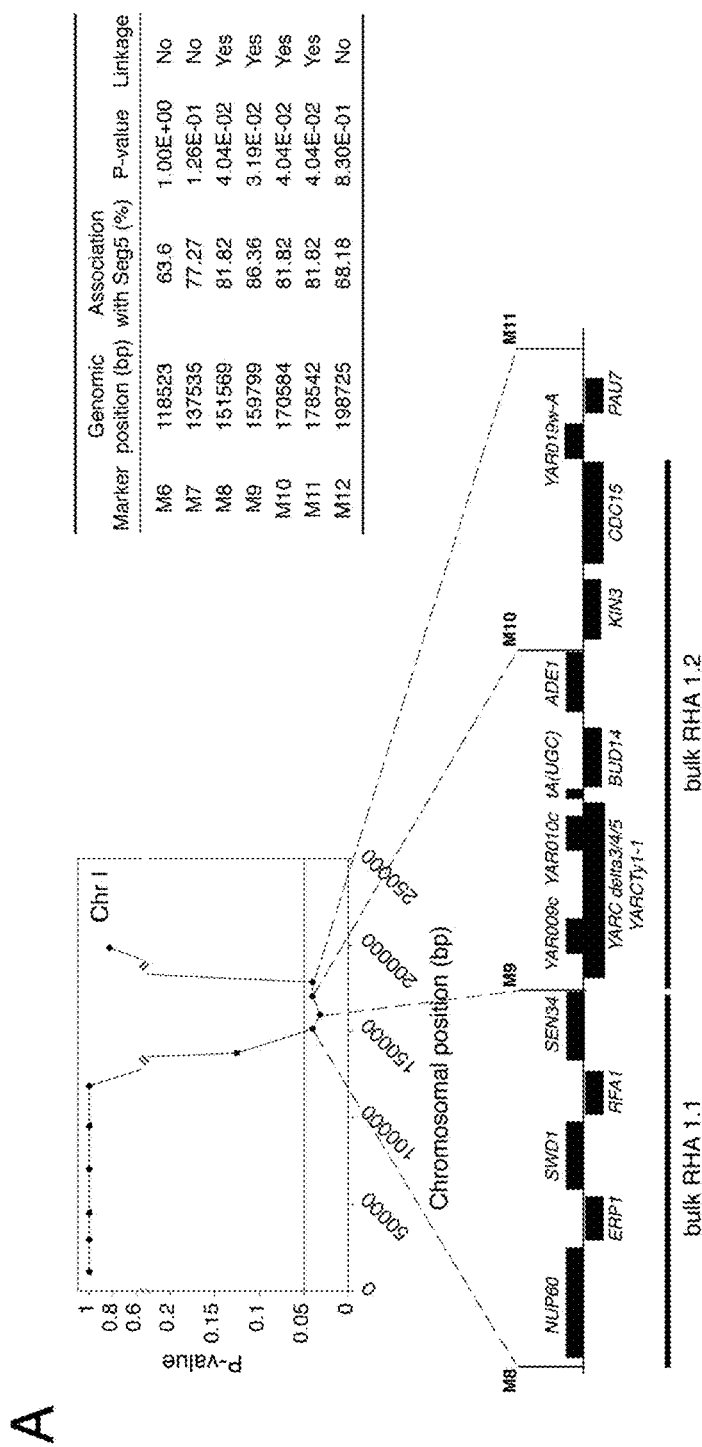
Figure 5:
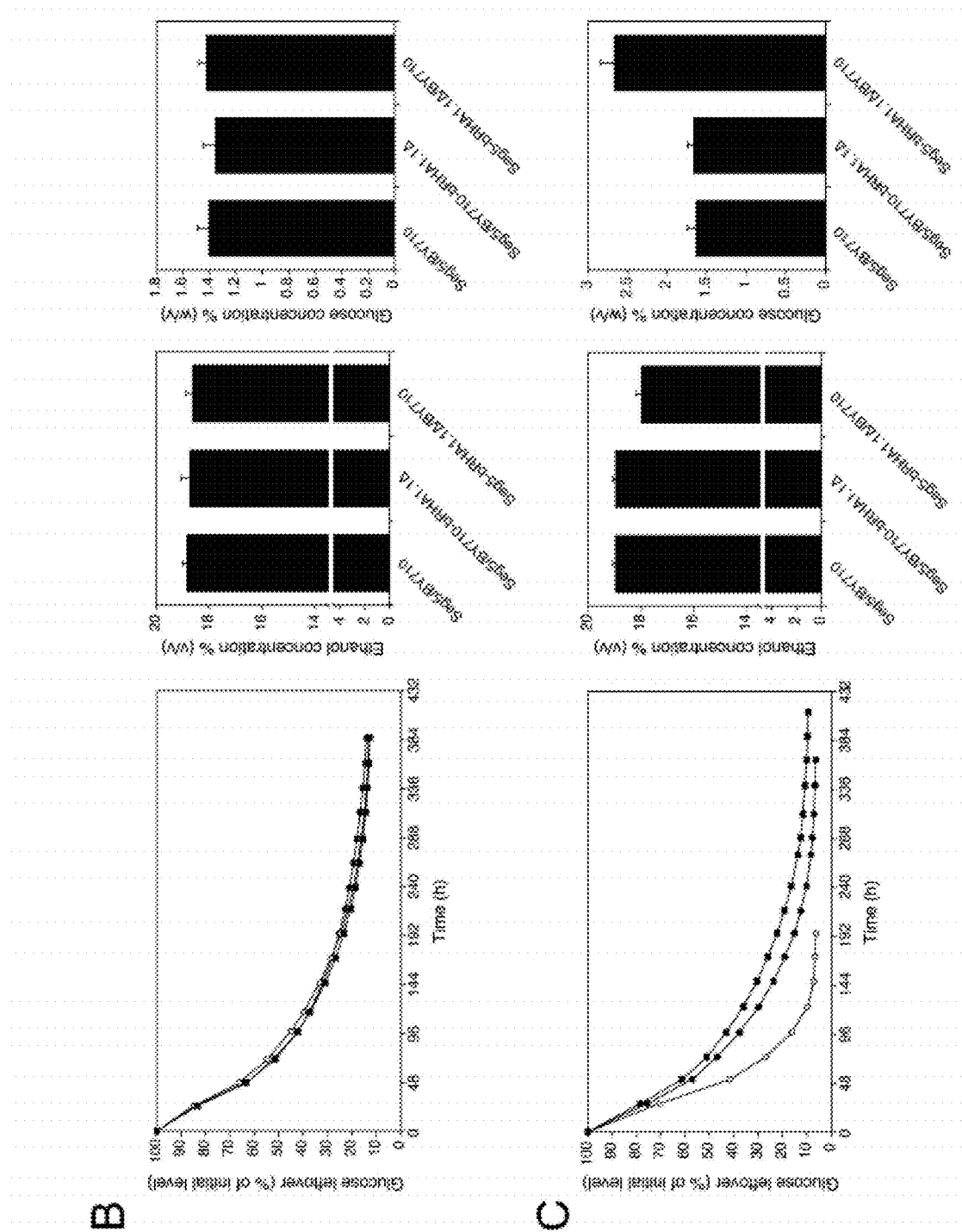

FIG. 5. Fine-mapping and bulk RHA of QTL2.

(A) Genes present in QTL2 (pool 1), located on chromosome I, as determined by markers scored in the 22 segregants individually. (B) Bulk RHA (bRHA 1.1) of genes NUP60, ERP1, SWD1, RFA1 and SEN34. Two heterozygous diploids for the five genes were constructed: Seg5/BY710-bRHA1.1Δ (○) and Seg5-bRHA1.1Δ/BY710 (■). These two diploids were compared with the original strain Seg5/BY710 (●) in semi-static fermentations performed in 250 mL of YP+33% glucose at 25° C. (C) Bulk RHA (bRHA 1.2) of genes YARCdelta3/4/5, YARCTy1-1, YAR009c, YAR010c, tA(UGC), BUD14, ADE1, KIN3, and CDC15. Two heterozygous diploids for the previous genes were constructed: Seg5/BY710-bRHA1.2Δ (○) and Seg5-bRHA1.2Δ/BY710 (■). These two diploids were compared with the original strain Seg5/BY710 (●) in semi-static fermentations performed in 250 mL of YP+33% glucose at 25° C.

Figure 6:
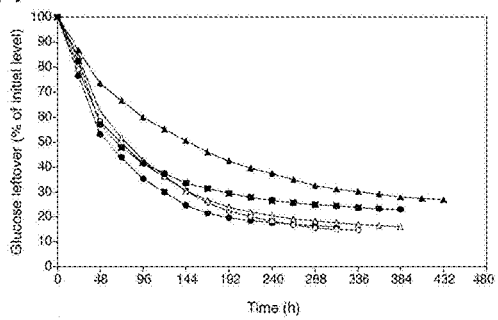
Figure 6:
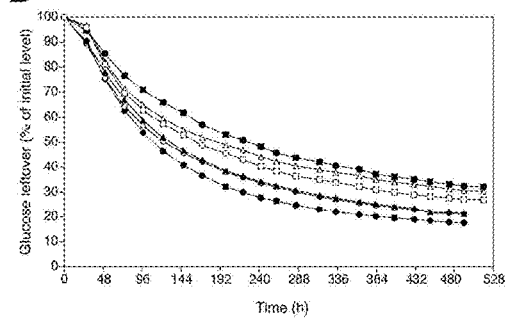
Figure 6:
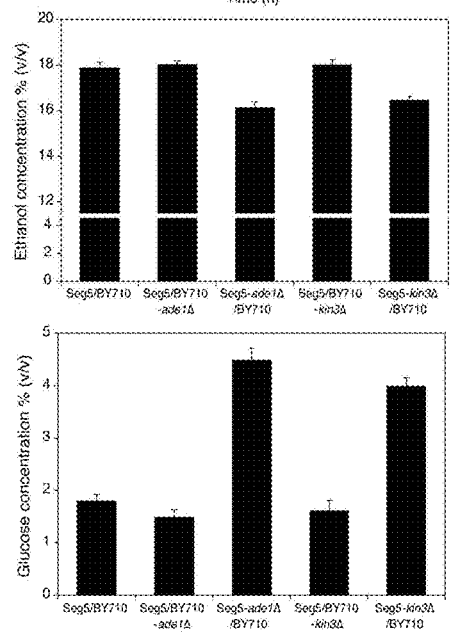
Figure 6:
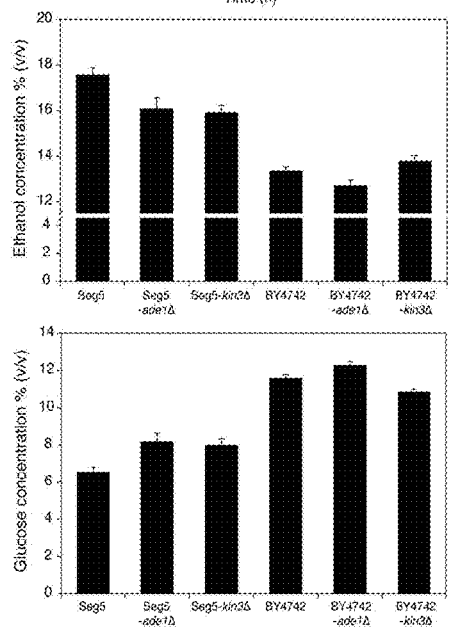
Figure 6:
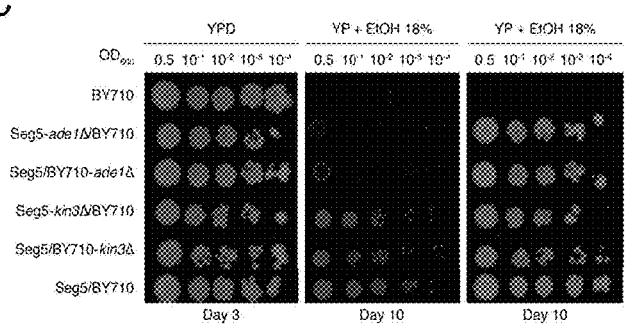

FIG. 6. Single gene RHA and loss of function assessment for the causative genes ADE1 and KIN3 in QTL2.

(A) RHA of genes ADE1 and KIN3. The diploid strain Seg5/BY710 (●) had ADE1 or KIN3 deleted in one of the alleles separately. The resulting strains Seg5/BY710-ade1Δ (○), Seg5-ade1Δ/BY710 (▲), Seg5/BY710-kin3Δ (Δ) and Seg5-kin3Δ/BY710 (■) were compared with the original diploid Seg5/BY710 (●) in semi-static small-scale fermentations in YP+33% glucose at 25° C. The deletion of the alleles present in Seg5 resulted in diploids with lower ethanol accumulation capacity in comparison to the original strain and the deletion of the alleles from BY710. (B) ADE1 and KIN3 loss-of-function assays. The genes ADE1 and KIN3 were deleted in the haploid strains Seg5 (●) and BY4742 (Δ) separately. The strains Seg5-ade1Δ (○), Seg5-kin3Δ (▲), BY4742-ade1Δ (■) and BY4742-kin3Δ (□) were evaluated by semi-static fermentations in 250 mL of YP+33% glucose at 25° C. (C) Determination of ethanol tolerance of cell proliferation with the hybrid diploid strains Seg5/BY710-ade1Δ, Seg5-ade1Δ/BY710, Seg5/BY710-kin3Δ and Seg5-kin3Δ/BY710.

Figure 7:
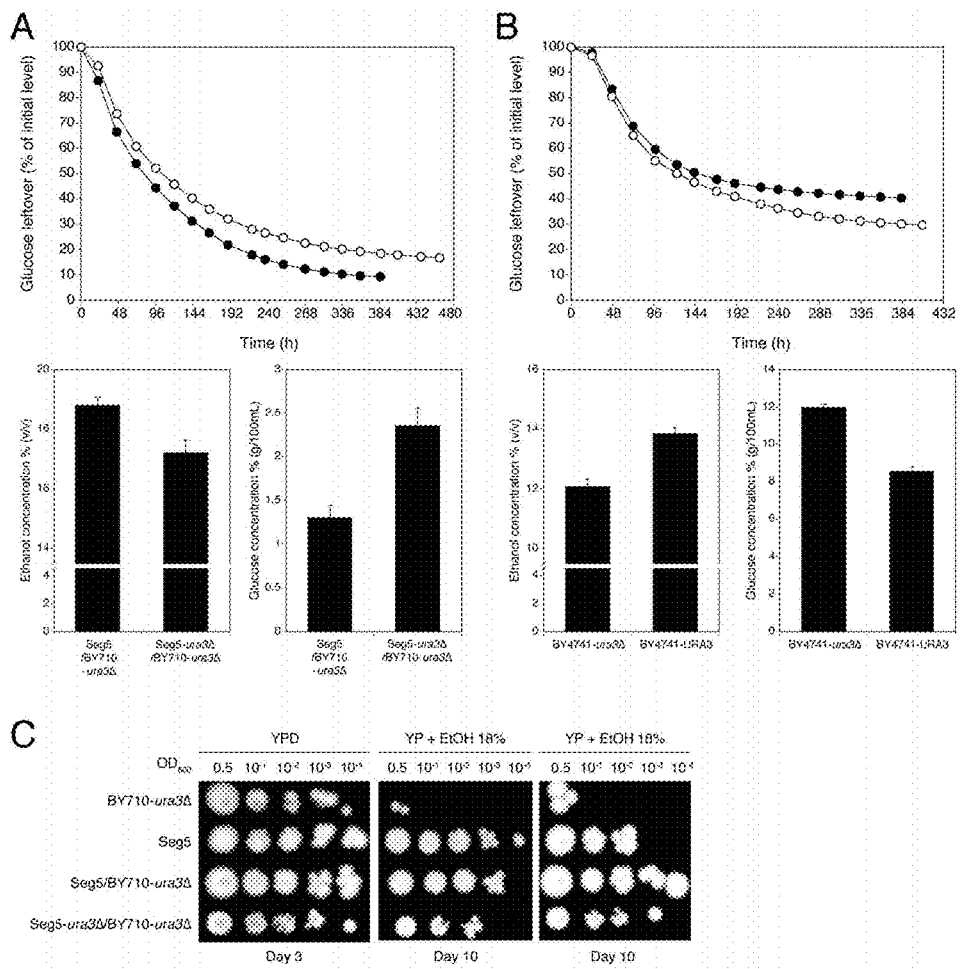

FIG. 7. Loss of function assessment and complementation assay with the causative gene URA3 in QTL3.

(A) URA3 loss-of-function assay. The strain Seg5/BY710 (●) had its URA3 copy deleted, Seg5-ura3Δ/BY710 (○). Both strains were tested in 250 mL of YP+33% glucose at 25° C. (B) URA3 complementation study. The URA3 auxotrophic strain BY4741-ura3Δ (●) had the URA3 gene inserted in its original position, BY4741-URA3 (○). The performance of both strains was assessed by semi-static fermentations in 250 mL of YP+33% glucose at 25° C. (C) Determination of ethanol tolerance of cell proliferation with the hybrid diploid strains Seg5/BY710-ura3Δ, Seg5-ura3Δ/BY710-ura3Δ.

Figure 8:
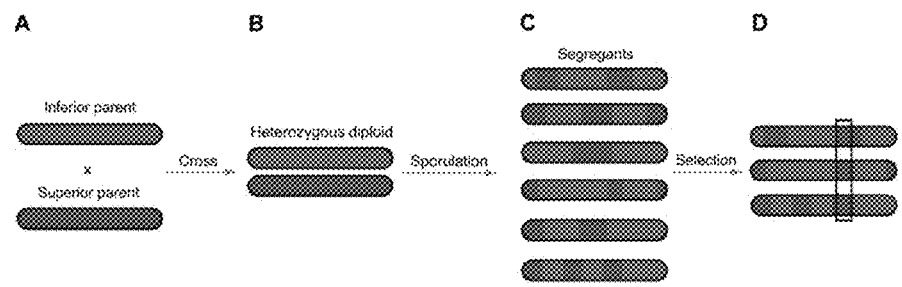

FIG. 8. Bulk segregant analysis for mapping genomic regions linked to a phenotype of interest in yeast.

A: A parent displaying the phenotypic trait of interest (superior parent) is crossed with a reference strain lacking the trait (inferior parent). B: The resulting heterozygous diploid strain is then sporulated to generate haploid segregants. C: Segregating offspring carry a mosaic of genetic material derived from both parents (red and blue segments)

due to the recombination events in meiosis. After phenotyping, the subset of segregants displaying the trait of the superior parent is selected. D: Genomic DNA extracted from the pooled selected segregants is submitted to whole-genome sequence analysis. Polymorphic genomic regions (marker sites) are identified that allow distinguishing between the parental variants. Counting for each marker site how many variants originate from the superior versus the inferior parent allows determining the variant frequency in the pool for each marker site. Regions linked to the phenotype of interest are expected to originate predominantly from the superior parent (black boxed region). The principle of BSA with diploid organisms is similar, but usually inbred (homozygous) lines are used as parents.

Figure 9:
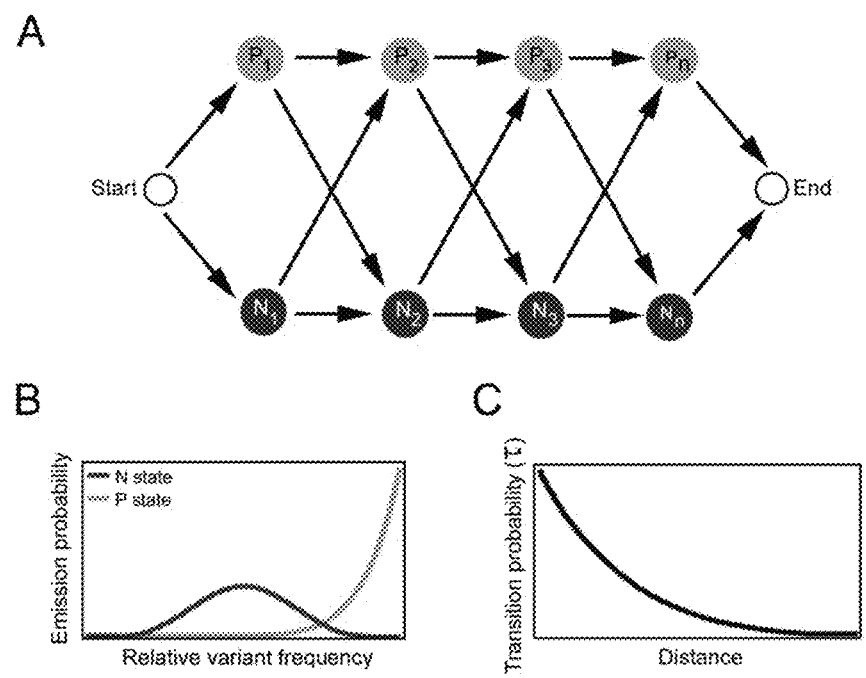

FIG. 9. Hidden Markov Model used to predict genomic regions linked to the phenotype of interest.

A: each marker site is modeled to be in a neutral state (N-state, blue circles) or in a state of being linked to the phenotype of interest (P-state, orange circles) based on its observed relative variant frequency in the pool of segregants. B: emission probabilities for, respectively, the neutral (blue curve) and the phenotype-linked states (orange line) as a function of the relative variant frequencies, modeled by a beta-binomial distribution with respective parameters α and β. C: transition probability as a function of Winzeler E A, et al., (1998) the physical distance between neighboring marker sites.

Figure 10:
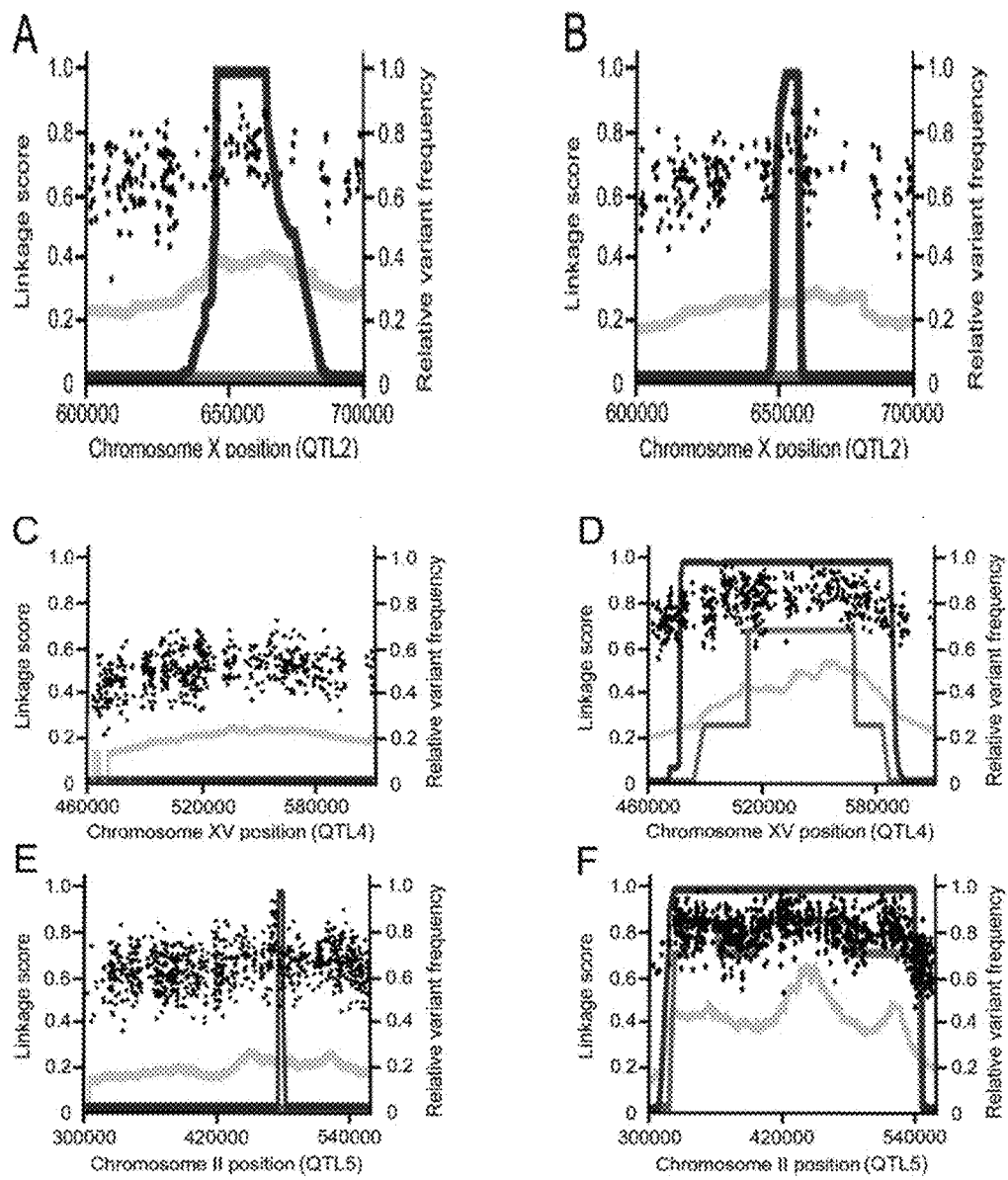

FIG. 10. Linkage scores obtained by EXPLoRA.

A: QTL2 on chromosome X in the pool tolerant to 16% ethanol; B: QTL2 on chromosome X in the pool tolerant to 17% ethanol; C: QTL4 on chromosome XV in the pool tolerant to 16% ethanol; D: QTL4 on chromosome XV in the pool tolerant to 17% ethanol; E: QTL5 on chromosome II in the pool tolerant to 16% ethanol; F: QTL5 on chromosome II in the pool tolerant to 17% ethanol. The original relative variant frequencies as determined by genome sequencing are also displayed for each plot (black dots).

Figure 11:
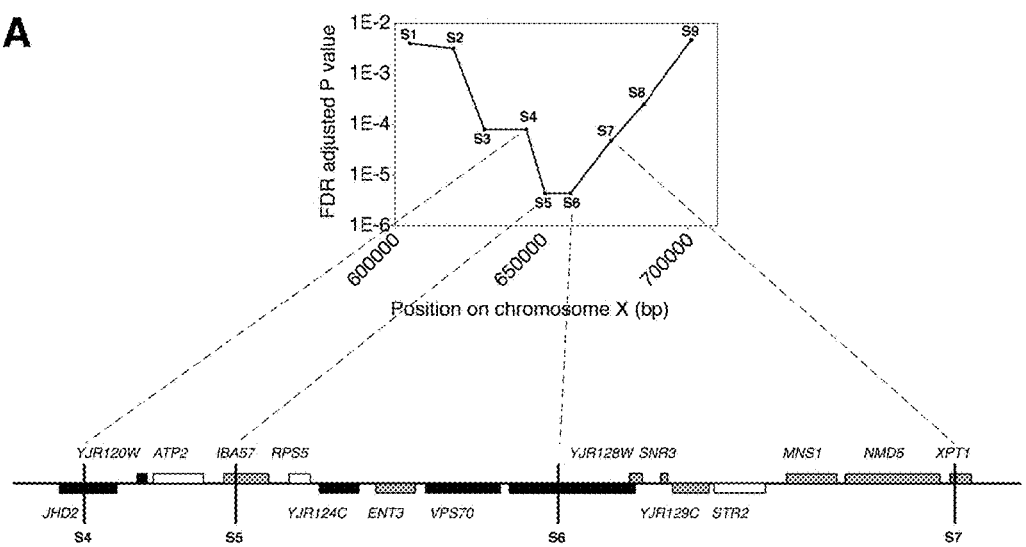
Figure 11:
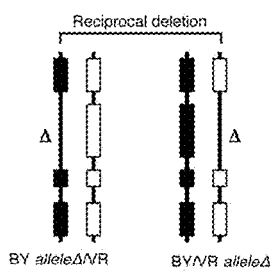
Figure 11:
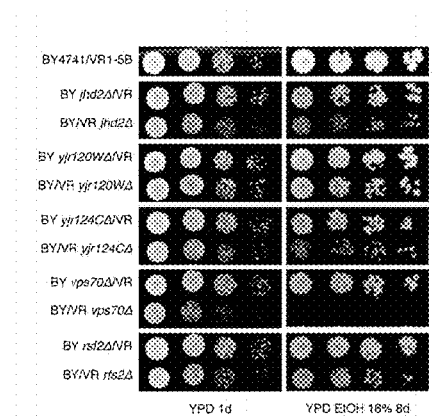

FIG. 11. Experimental validation of QTL2 on chromosome X.

A: upper plot shows the region corresponding to QTL2 of which linkage to the phenotype of interest was confirmed by scoring selected marker sites in individual segregants. Scored marker sites are indicated (S4-S7). For each marker site, the p-value indicates the probability to be linked to the phenotype by chance, according to a binomial distribution (see materials and methods). Lower plot: zoom in on the genes in the experimentally confirmed region corresponding to QTL2 (29 kb). Black bars: genes with non-synonymous mutations in the coding region; grey bars: genes with mutations in the promotor or terminator; white bars: genes without mutations. B: Reciprocal hemizygosity analysis for the genes with non-synonymous mutations in the coding regions located in the fine-mapped region. To that end, two different diploid strains were constructed by crossing the original superior parent VR1-5B with the inferior parent BY4741, carrying a deletion in its allele of the candidate causative gene or the other way around. Hence, this resulted in two different diploid strains, each with only one functional allele of the candidate causative gene, originating from either the "superior" or the "inferior" parent. The ethanol tolerance of the two diploid strains was compared with dilution spot growth assays on a YPD plate with 16% ethanol and a YPD plate without ethanol as control. C: Ethanol tolerance of BY4741 and VR1-5B and the corresponding VPS70 deletion strains was determined by scoring growth of tenfold dilutions of cultures of these strains on YPD plates in the absence and in the presence of different ethanol concentrations.

Figure 12:
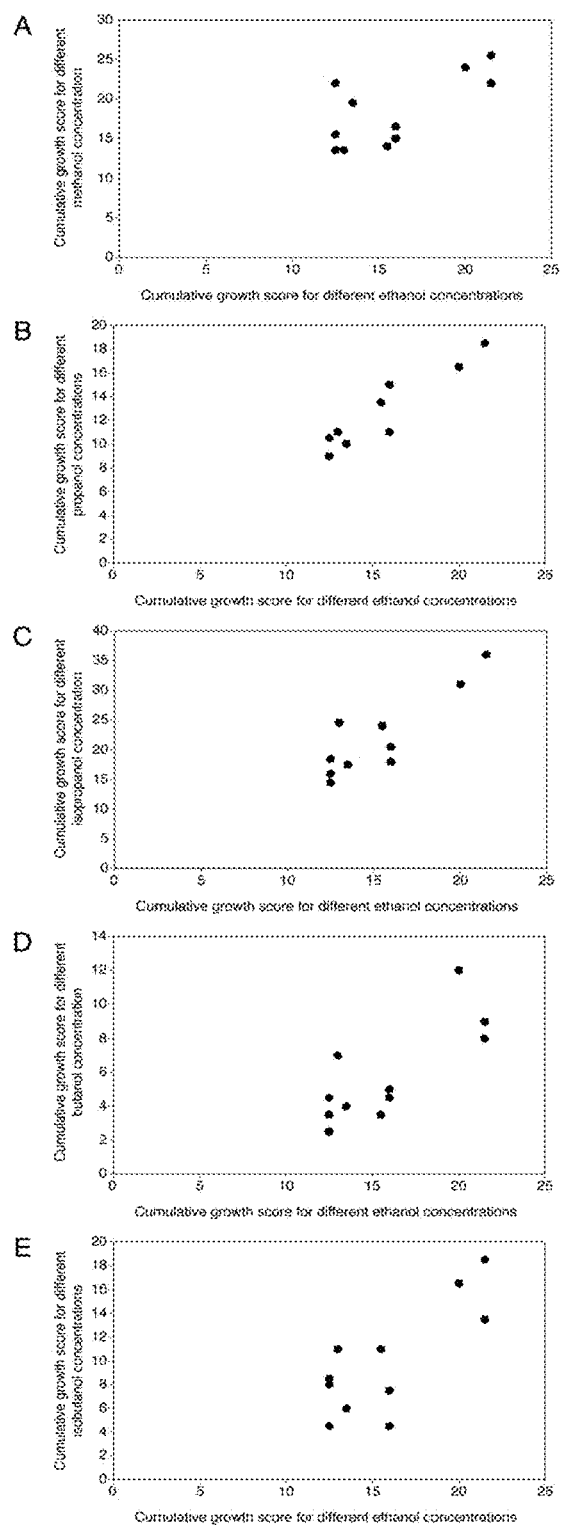

FIG. 12: Correlation between tolerance to ethanol and tolerance to methanol, propanol, isopropanol, butanol and isobutanol in two parent strains (VR1-5B and BY4741) and multiple segregants of the cross between the two parents.

Growth was tested in the presence of different alcohol concentrations on solid nutrient plates with YPD using serial dilution spot tests. Growth was scored at each alcohol concentration based on the number of dilution spots in which growth was visible. For each strain the scores obtained at the different alcohol concentrations were counted together to obtain the cumulative growth score for that strain in the presence of the specified alcohol.

Figure 13:
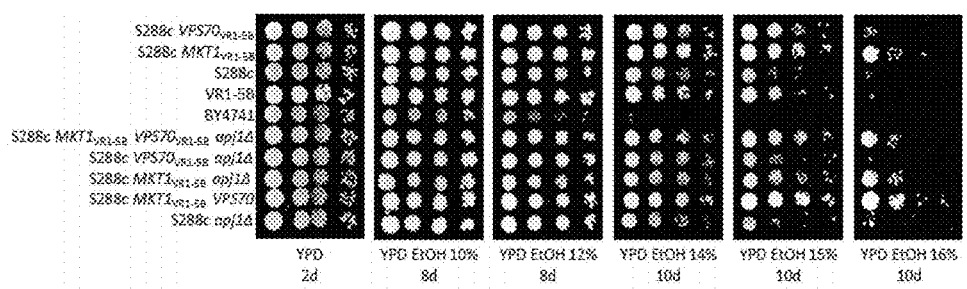

FIG. 13. S288c with different combinations of superior alleles for ethanol tolerance.

Ethanol tolerance of S288c with different combinations of the superior alleles for this trait identified by Swinnen et al., 2012 together with VR1-5B (superior) and BY4741 (inferior) was determined by scoring growth of tenfold dilutions of these cultures on YPD plates in the absence and in the presences of different ethanol concentrations. The combination of the genes MKT1 and VPS70 of the superior parent VR1-5B showed the best improvement for growth on YPD plates with high ethanol concentrations compared to the single gene replacements and other combinations. MKT1 displaces the highest contributions to ethanol tolerance followed by VPS70 and Δpj1Δ.

DETAILED DESCRIPTION

EXAMPLES

Materials and Methods

Strains and Growth Conditions

The *S. cerevisiae* strains utilized in this study are listed in Table 1. Yeast cells were grown with orbital agitation (200 rpm) at 30° C. in YPD medium containing 1% (w/v) yeast extract, 2% (w/v) Bacto peptone and 2% (w/v) glucose.

TABLE 1

*Saccharomyces cerevisiae* strains utilized in this study

| Strain | Description/use | Reference/origin |
|---|---|---|
| BY4741 | Mata his3Δ1 leu2Δ0 ura3Δ0 met15Δ0 | (Brachmann et al., 1998) |
| BY4742 | Matα his3Δ1 leu2Δ0 ura3Δ0 lys2Δ0 | (Brachmann et al., 1998) |
| BY4743 | Mata/α his/his leu/leu ura/ura met/MET LYS/lys | (Brachmann et al., 1998) |
| S288c | Mata prototroph | (Brachmann et al., 1998) |
| BY710 | BY4742 derivative; Matα his3Δ1 leu2Δ0 ura3Δ0 lys2Δ0 | Lab stock |

TABLE 1-continued

*Saccharomyces cerevisiae* strains utilized in this study

| Strain | Description/use | Reference/origin |
|---|---|---|
| CBS1585 | Heterothallic diploid sake strain with high ethanol production capacity | Centraalbureau voor Schimmelcultures, Utrecht, The Netherlands |
| Seg5 | Haploid derived from CBS1585 with the same phenotype, Mata | This study |
| Seg5xBY710 | Diploid obtained by crossing Seg5 with pAMS710 | This study |
| V1116 | Homothallic diploid wine strain | Lallemand, Canada |
| CAT1 | Brazilian bioethanol production | Fermentec, Brazil |
| VR1 | Brazilian bioethanol production | Fermentec, Brazil |
| PE2 | Brazilian bioethanol production | Fermentec, Brazil |
| CBS1198 | Sake | Centraalbureau voor Schimmelcultures, Utrecht, The Netherlands |
| CBS436 | Sake | Centraalbureau voor Schimmelcultures, Utrecht, The Netherlands |
| CBS6412 | Sake (Kyokai n°7) | Centraalbureau voor Schimmelcultures, Utrecht, The Netherlands |
| CBS6413 | Sake (Kyokai n°5) | Centraalbureau voor Schimmelcultures, Utrecht, The Netherlands |
| CBS6414 | Sake | Centraalbureau voor Schimmelcultures, Utrecht, The Netherlands |
| CBS7539 | Beer, Bulgaria | Centraalbureau voor Schimmelcultures, Utrecht, The Netherlands |
| CBS382 | Beer, Brazil | Centraalbureau voor Schimmelcultures, Utrecht, The Netherlands |
| CBS422 | Beer, Ukraine | Centraalbureau voor Schimmelcultures, Utrecht, The Netherlands |
| CMBS33 | Lager beer strain | Centre for malting and brewing collection, KULeuven |
| GT336 | CMBS33 variant | (Blieck et al., 2007) |
| GT339 | CMBS33 variant | (Blieck et al., 2007) |
| GT344 | CMBS33 variant | (Blieck et al., 2007) |
| Westmalle | Beer bottle yeast isolate | Isolated from Westmalle triple beer (9.5% v/v alcohol) |
| CBS1252 | *S. cerevisiae* or *S. paradoxus* | Centraalbureau voor Schimmelcultures, Utrecht, The Netherlands |
| CBS1390 | Wine, Hungary | Centraalbureau voor Schimmelcultures, Utrecht, The Netherlands |
| CBS7764 | *Salmo gairducrii* (rainbow trout), Sweden | Centraalbureau voor Schimmelcultures, Utrecht, The Netherlands |
| CBS7957 | Factory of cassava flour, Brazil | Centraalbureau voor Schimmelcultures, Utrecht, The Netherlands |
| CBS7958 | Factory of cassava flour, Brazil | Centraalbureau voor Schimmelcultures, Utrecht, The Netherlands |
| CBS1241 | *S. cerevisiae* or *S. paradoxus* | Centraalbureau voor Schimmelcultures, Utrecht, The Netherlands |
| Produtor 3 | Cachaça (spirit) production | Sugar cane fermentation, UFOP, Brazil |
| Produtor 4 | Cachaça (spirit) production | Sugar cane fermentation, UFOP, Brazil |
| Montanhesa Atividade | Cachaça (spirit) production | Sugar cane fermentation, UFOP, Brazil |
| Diva | Cachaça (spirit) production | Sugar cane fermentation, UFOP, Brazil |
| Benvinda | Cachaça (spirit) production | Sugar cane fermentation, UFOP, Brazil |
| Montanhesa Pe | Cachaça (spirit) production | Sugar cane fermentation, UFOP, Brazil |
| CBS7959 | Bioethanol from sugar cane | Brazil |
| CBS7960 | Bioethanol from sugar cane | Brazil |
| CBS7961 | Bioethanol from sugar cane | Brazil |
| 46EDV | Bioethanol | Lallemand, Canada |

TABLE 1-continued

Saccharomyces cerevisiae strains utilized in this study

| Strain | Description/use | Reference/origin |
| --- | --- | --- |
| Thermosacc Dry | Bioethanol | Lallemand, Canada |
| Superstart | Bioethanol | Lallemand, Canada |
| Ethanol Red | Bioethanol | Lesaffre, France |
| Fali S1 | Bioethanol | AB Mauri, Australia |
| Fali S2 | Bioethanol | AB Mauri, Australia |
| *S. boulardii* | Probiotic | Enterol 250 mg (Biodiphar) |
| Y55 | Prototroph diploid | Lesaffre Development, France |
| Sake4134 | Sake | Homebrewers warehouse |
| TMB3399 | Xylose utilization | (Wahlbom et al., 2003) |
| TMB3400 | Xylose utilization | (Wahlbom et al., 2003) |
| CBS1200 | *S. cerevisiae* or *S. paradoxus* | Centraalbureau voor Schimmelcultures, Utrecht, The Netherlands |
| Alcotec 24 h | Bioethanol | Alcotec, United Kingdom |
| Alcotec 48 h | Bioethanol | Alcotec, United Kingdom |
| Alcotec 23% | Bioethanol | Alcotec, United Kingdom |
| Turbo yeast | Bioethanol | Alcotec, United Kingdom |
| Vodka star | Spirit | Alcotec, United Kingdom |
| Turbo triple still | Spirit | Alcotec, United Kingdom |
| CBS2807 | Wine (Slovakia) | Centraalbureau voor Schimmelcultures, Utrecht, The Netherlands |
| CBS2808 | Wine (Slovakia) | Centraalbureau voor Schimmelcultures, Utrecht, The Netherlands |
| CBS7072 | Bioethanol | Centraalbureau voor Schimmelcultures, Utrecht, The Netherlands |
| Eau de vie | Spirit | WYEAST Laboratories |
| French Red | Wine | UCDavis, USA |
| Riesling Hefe | Homothallic diploid | Zimmermann F. (Darmstadt) |
| SIHA3 | Homothallic diploid | Zimmermann F. (Darmstadt) |
| Pasteur Champagne | Wine | UCDavis, USA |
| Intek796 | Wine | UCDavis, USA |
| Fermivin | Wine | Oenobrands, France |
| M2 | Wine | UCDavis, USA |
| Sauternes | Wine | UCDavis, USA |
| Champagne | Wine | UCDavis, USA |
| Port | Spirit | UCDavis, USA |
| Cognac | Spirit | UCDavis, USA |
| Sake K11 | Sake | National Research Institute of Brewing, Japan |

Small-Scale VHG Fermentations

VHG fermentations were performed in which the glucose concentration was raised to such an extent (33% w/v) that a maximal final ethanol level (17-18%) was obtained with only minimal residual sugar left (Puligundia et al., 2011). A further increase in glucose concentration above this level reduced the maximal ethanol level again. Cells were first pre-grown in 3 mL of YPD medium for 24 h (200 rpm, 30° C.), after which 0.5 mL was transferred to 5 mL of YP+5% (w/v) glucose and the culture incubated for 24 h (200 rpm, 30° C.). Cells of the last pre-culture were inoculated in 100 mL of YP+10% (w/v) glucose with initial OD600 of 1.0. The cells were grown for 2 days (200 rpm, 30° C.) until stationary phase. $12.5 \times 10^9$ cells, based on cell counting, were harvested. The cells were centrifuged (3000 rpm, 5 min, 4° C.), the pellet was resuspended in 3 mL of YP and inoculated into 250 mL of YP+33% (semi-static) or 35% (continuous stirring) (w/v) glucose. The fermentations were performed at 25° C. Agitation was performed with a magnetic rod (30×6 mm) at 120 rpm (semi-static, 4 h) or 200 rpm (continuous stirring). The fermentation was followed by weighing the tubes and from the weight loss the glucose leftover was calculated. Samples were taken at the end of the fermentation for HPLC analysis and cell viability determination. The metabolites quantified by HPLC were glucose, glycerol and acetic acid. The HPLC system utilized (Waters Breeze) consisted of an ion-exclusion column (WAT010290) at 75° C. and detection was performed by refractive index (model 2414). The eluent used was $H_2SO_4$ (5 mM) at a flow rate of 1.0 mL/min. Samples of 10 µL were automatically injected and processed for 20 min. Ethanol was quantified by near infrared spectroscopy (Alcolyzer, Anton Paar). Cell viability was assessed by oxonol staining followed by flow cytometry analysis (Boyd et al., 2003). The ethanol yield (g of ethanol produced per g of glucose consumed) was calculated by dividing the ethanol produced with the glucose consumed (initial glucose concentration minus glucose leftover).

Ethanol Tolerance Assays on Solid Media

The cells were pre-grown in YPD for 2 days (200 rpm, 30° C.). The OD600 was measured in triplicate and the cells were diluted to an initial OD600 of 0.5. Four serial dilutions were made ($10^{-1}$, $10^{-2}$, $10^{-3}$ and $10^{-4}$). A volume of 4 µL was spotted on plates: YPD (control), YPD+16% (v/v) ethanol, YP+16% (v/v) ethanol, YPD+18% (v/v) ethanol, YP+18% (v/v) ethanol and YPD+20% (v/v) ethanol. The plates were incubated at 30° C. for up to 11 days and growth was scored from the second day on. The ethanol levels indicated are initial ethanol levels. During the preparation and incubation of the plates some ethanol may evaporate. Therefore, sample and control strains were always put together on the same plates.

Sporulation and Tetrad Dissection

General procedures for sporulation and tetrad dissection were used (Sherman and Hicks, 1991).

Determination of Mating Type

A small amount of cells (1.5 mg) was incubated with 10 µL of NaOH (0.02 N) for 1 h (RT). The determination of the mating type was done by PCR with the primers for the MAT locus and MATα and MATα (alpha) DNA (Huxley et al., 1990). The 3 primers were used together.

Genomic DNA Extraction and Whole-Genome Sequence Analysis

Preparation of the DNA pools from the segregants was done either by (1) individual genomic DNA extraction and pooling of the DNA in equimolar concentrations; (2) mixing of the cells, based on dry weight, prior to DNA extraction, or (3) mixing of the cells based on OD600, prior to DNA extraction. For all preparations, the genomic DNA was extracted, according to Johnston (1994). At least 3 µg of DNA per pool was provided for whole-genome sequencing to both GATC Biotech GA (Konstanz, Germany) and Beijing Genomics Institute (BGI, Hong Kong, China). In both cases, the sequencing was performed with the Illumina platform and gave very similar results.

Bioinformatics Analysis and Confirmation of QTLs

Assembly and mapping were done with DNAstar Lasergene software. Smoothing of the sequencing data was performed with a Linearized Mixed Model (LMM) framework (Swinnen et al., 2012a; Claesen et al., 2013). We implemented a Hidden Markov Model (HMM) to identify regions related with the phenotypes similar to the one implemented in the FastPHASE package (Sheet and Stephens, 2006). For each variant, the HMM has three possible states: (i) relation with the superior parent, (ii) relation with the control parent and (iii) no relation (background). To capture the effect of recombination, the transition between two states of the same type is the probability of no recombination and the probability of the transition between two states of different type is the probability of recombination divided by two. We estimated the probability of recombination for each pair of neighbor variants using a negative exponential relation with the physical distance as in Sheet and Stephens (2006). The emission of each state is the number of calls of the alternative allele which is an integer between zero and $n_i$, where $n_i$ is the total number of allele calls for the variant i. We used beta-binomial distributions for all states to take into account the fact that given the finite number of segregants, the contribution of each parent to the pool is not exactly half. For the superior parent states we setup $\alpha=10$ and $\beta=1$. For the control parent states we set $\alpha=1$ and $\beta=10$. For the background states we estimated $\alpha$ and $\beta$ using the alternative allele frequencies in all sites. We checked that for the background distribution $\alpha \approx \beta > 1$, which makes the background distribution to be close to a binomial with probability 0.5 (as expected). We used the forward-backward algorithm to calculate the posterior probability of each state given the allele counts for each dataset. A manuscript with a complete explanation of the algorithm and comparisons with currently available methods is in preparation. The QTLs detected were further analyzed by scoring SNPs in the segregants individually using allele-specific primer sets, which were rigorously tested for reliability with the two variants of each SNP in the parent strains and all segregants. Statistically significant QTLs were confirmed by multiple testing using a false discovery rate (FDR) control (Benjamini and Yekutieli, 2005).

Development of Explora

Datasets

A segregant, VR1-5B from a Brazilian bioethanol production strain VR1 (superior parent) was crossed with the BY4741 lab strain. A total of 136 segregants tolerant to 16% ethanol and out of these, 31 segregants tolerant to 17% ethanol, were pooled. DNA of the pools and also of the VR1-5B parental strain was extracted and sequenced using Illumina technology (Swinnen et al., 2012a). A total of 131 unselected segregants from the same cross were also pooled and sequenced as control experiment (unselected pool).

Identifying Marker Sites

The yeast S288c reference genome (3 Feb. 2011 release) available in the Saccharomyces Genome Database (World Wide Web at yeastgenome.org) was used as a reference. All reads from the parental strain VR1-5B were mapped to the reference sequence using BFAST (Homer et al., 2009). To facilitate the discovery of repetitive regions in the genome of the parental strain VR1-5B, we retained for each read, its alignments with an edit distance difference from its best alignment smaller or equal to 5. About 90% of the reads from VR1-5B, about 80% of the reads from the pools of segregants under selection and about 96% of the reads from the pool of unselected segregants could be mapped to the latest reference genome. When verifying the mapping quality we observed that the error rate in the reads from VR1-5B, and the two pools of selected segregants increased above 2% in the last 20 bp. These last 20 bp of each read were, therefore, discarded when performing the mapping. We obtained an average coverage of 55× for the read alignments of VR1-5B and the read alignments of the two pools of selected segregants as well as for the read alignments from the pool of unselected segregants.

Repetitive regions (i.e., small tandem repeats) were subsequently identified by connecting for each read all retained alignments that are located within a neighboring genomic region. We also considered as repeats, regions already annotated in the reference genome as transposons, telomeres, centromeres, and paralog gene families. To identify copy number variants (CNVs) in the parental strain VR1-5B not yet annotated in the reference strain, we used the CNVnator algorithm (Abyzov et al., 2011). SNPs and small indels were identified with the SNVQ algorithm (Duitama et al., 2012), hereafter referred to as calls. Calls with posterior probability score less than 80, as well as calls falling inside repetitive or CNV regions were filtered out. Retained calls correspond to marker sites that allow distinguishing between both parental alleles (S288c and VR1-5B). Using our variant mapping and identification procedure, we identified 883 regions with multiple mappings and 2 804 novel CNVs that together with the 1 446 regions already annotated as repetitive regions comprised a total of 5 133 regions, covering 3.4 Mb (27.44%) of the genome. Only the 37 473 SNPs and 867 indels located outside these CNVs and repetitive regions were used for further analysis.

Inferring Relative Variant Frequencies

All reads from the two selected pools and from the unselected pool were mapped to the reference sequence using BFAST (Homer et al., 2009). For each pool, we inferred relative variant frequencies, by counting at each marker site the number of read alignments that support the variant originating from the superior parent (VR1-5B) (referred to as the superior variant) versus the total number of alignments. A mapped read was discarded during frequency calculation when it had a base quality score less than 10 at the marker site or if it did not match any of the parental variants at the marker site. Resulting relative variant frequencies were used as input for EXPLoRA.

Development of EXPLoRA, a HMM for the Analysis of BSA Data

Theoretically, for any marker site not linked to the phenotype of interest, the variants in the pool of segregants should be inherited in equal proportions from either parent (null hypothesis). In such hypothetical ideal case, a statistical test (e.g., binomial cumulative probability (Swinnen et al., 2012a)) could be applied to each genetic marker separately to assess the extent to which the variant frequency at the marker site deviates from the expected inheritance probability of 50%. In reality, spurious deviations of the observed variant frequencies from the theoretical 50% at marker sites will occur due to experimental error.

Additionally, linkage disequilibrium produces deviations of variant counts towards the superior variant, not only at the genetic marker sites causative to the phenotype of interest, but also in genetic marker sites closely located to these causative marker sites. This dependence between the variant frequency of neighboring sites violates the assumptions of independently linking variants to a phenotype of interest, according to a binomial distribution. However, when properly accounted for in the BSA analysis model, this dependency between neighboring sites can help increasing the power of the statistical linkage of the loci with the phenotype of interest and in filtering out spurious hits that are due to experimental errors.

Therefore, to use the information contained in the dependency between neighboring marker sites, we developed a Hidden Markov Model (HMM) called EXPLoRA (FIG. 9). For each marker site, we model two possible states: one state (P-state) expresses that the variants in the pool at that marker site originate predominantly (but not always in all segregants) from the superior parent and are thus linked to the phenotype of interest. A second state (N-state) models that the variants in the pool at a given marker site result to an equal extent from either parent, in which case the marker site is assumed to be located in a neutral region not linked to the phenotype of interest. The effect of linkage disequilibrium is modeled by the transition probabilities $\tau$ between two neighboring marker sites. The transition probability $\tau$ models the chance that a neighboring site remains in the same state as its preceding site state. Its distribution is described by a negative exponential model as a function of the recombination rate and thus the physical distance between neighboring marker sites (Sheet and Stephens, 2006) (FIG. 9C). The probability to change states upon transition from one marker site to a neighboring marker site (from a neutral N-state to a phenotype-linked P-state or vice versa) is then described by $1-\tau$. The model captures the fact that marker sites located in each other's physical neighborhood are likely to be in linkage disequilibrium and less likely to change their state (from P to N or from N to P). Given a random state $N_i$ or $P_i$ at a marker site "i," the transition probabilities to the states $N_i+1$ or $P_i+1$ for the neighboring marker site "i+1" are given by:

$$\tau_{N_i \to N_{i+1}} = 1 - e^{-rl_i}$$

or $$\tau_{P_i \to P_{i+1}} = 1 - e^{-rl_i}$$

where $I_i$ is the physical distance between the marker sites i and i+1 and r is a recombination rate, which is determined by the average number of crossing-overs occurring during meiosis over a given distance in a chromosome. r was fixed at $3.5 \times 10^{-6}$, based on the estimations derived by Ruderfer et al., 2006.

Each state in the model emits a random variable $n_A$, corresponding to the number of variant counts at a given marker site originating from the superior parent. $n_A$ ranges from 0 to n, with n being equal to the (known) total variant count for the marker site, and is described by a beta binomial distribution which allows capturing different emission probabilities in phenotype-linked versus neutral states by choosing different $\alpha$ and $\beta$ parameters for their corresponding distributions (FIG. 9B). We modeled all neutral states with the same parameters $\alpha_N$ and $\beta_N$, and all phenotype-linked states with the same parameters $\alpha_P$ and $\beta_P$. While for the neutral states $\alpha_N$ should almost equal $\beta_N$ to make values of $n_A$ closer to n/2 more likely to be sampled, for the phenotype-linked states $\alpha_P$ should be much larger than $\beta_P$ to make values of $n_A$ close to n more likely to be sampled.

Given the observed total variant count and the variant counts that originate from the superior parent at each marker site (D) and fixed values for the parameters $\alpha_N$, $\beta_N$, $\alpha_P$, $\beta_P$, and $\tau$, we can calculate the posterior probability of each state in the HMM with a standard forward-backward algorithm (Sheet and Stephens, 2006). For each marker site, we then estimate its probability to be linked to the phenotype of interest as the normalized probability $P(P_i|D)/ (P(P_i|D)+P(N_i|D))$.

Since most of the genomic regions are supposed to be neutral with respect to the phenotype of interest, the parameters $\alpha_N$ and $\beta_N$ of the emission probabilities in the neutral state can be estimated directly from the observed variant frequencies. To this end, we implemented a two-step process in which we first assume that most of the genomic regions are phenotype-neutral. We estimate with the method of moments the most likely values of $\alpha_N$ and $\beta_N$ given the variant frequencies at each marker site. Then in a second step we identify the marker sites linked to the phenotype of interest using the model, and we estimate again $\alpha_N$ and $\beta_N$ leaving out the marker sites identified to be linked to the phenotype. $\alpha_P$ and $\beta_P$ are adjustable parameters. In our experiments, we fixed $\beta_P$ equal to 1 and tested different values of $\alpha_P$ (5, 10, 20, and 50). A cut-off on the obtained posterior probability of each marker site to be linked to the phenotype was used to prioritize the most likely causative marker sites for the phenotype of interest.

Comparison with Other Methods

For comparison purposes, we analyzed the same data sets using the SHORE software package (Ossowski et al., 2008) considering gapped alignments of up to four mismatches to identify marker sites. The SHORE output for marker sites between the parental strain VR1-5B and the S288c reference genome agreed in 98% of the cases with the data obtained by BFAST and our filtering rules (see above). This made it possible to directly compare our EXPLoRA methodology with SHOREmap (Schneeberger et al., 2009) for further prioritization of variants originating from the superior parent linked to the phenotype of interest. To this end, relative variant frequencies derived from read alignments of the pools by SHORE were used as input for SHOREmap. A cut-off on the linkage scores at each marker site provided by SHOREmap was used to prioritize markers as being linked to the phenotype of interest. To obtain the optimal parameter setting for SHOREmap in this analysis, we ran the application with different window sizes. Eventually, a window size of 250 kb and step of 10 kb were chosen as this maximized the number of genetic marker sites with a normalized score ≥0.9 in the positive benchmark set.

The statistical model applied in the original publication by Swinnen et al., 2012a was also included in the comparison. An implementation of this model was obtained from the authors and ran on the same input as EXPLoRA using the default window size of 40 kb (we considered these parameters to be optimal for the dataset at hand as they were originally optimized on this dataset). A cut-off on the probability of each marker site to be linked to the phenotype derived from a binomial test on the smoothed data (p-value), provided by the method of Swinnen et al., 2012a was used to prioritize phenotype-linked marker sites.

Estimating the False Positive Rate

The number of false positive predictions at the level of the marker sites is estimated as the number of marker sites predicted to be linked to the phenotype in an unselected pool (those that pass the chosen cut-off on the linkage score in the random pool). The false positive rate is then calculated as the number of false positive predictions divided by the number of predictions obtained on the selected pool. The unselected pool should be of similar size in number of segregants as the selected pool, which is true for the case of the pool selected for tolerance to 16% ethanol (136 segregants in the selected pool versus 131 in the unselected one). To generate a corresponding unselected pool for the pool of segregants selected for tolerance to 17% ethanol, we sampled from the original unselected pool the same number of segregants as was present in this selected pool, that is 31.

To define the false positive rate at the level of the linked regions (QTLs), we first grouped "predicted marker sites" into "predicted linked regions" (i.e., consecutive neighboring marker sites that had a linkage score above the selected cut-off were grouped in regions) and determined the size of each predicted linked region in bp. Marker sites predicted to be linked to the phenotype based on a spurious deviation in relative variant frequency are not expected to be located in large regions. As a result, we expect that the average size of a predicted linked region in the unselected pools will be considerably smaller than in the selected pool. We, therefore, estimated as "falsely linked regions" in the selected pool, these predicted linked regions for which the size in bp was smaller than the 90 percentile largest predicted linked region observed in the unselected pool. This allowed us to calculate a false positive rate at the level of linked regions as the number of "falsely linked regions" divided by the total number of predicted linked regions in the unselected pool at the same chosen cut-off.

Experimental Validation

Experimental verification of QTL2 on chromosome X was based on scoring for selected marker sites in the identified region, the extent to which individual segregants selected for high ethanol tolerance display the variant originating from the superior parent (relative variant frequency in individual segregants) (Swinnen et al., 2012a). Relative variant frequencies in individual segregants were used to calculate the p-value of each marker site to be linked to the phenotype of interest using an exact binomial test with a confidence level of 95% and correction for multiple testing by a false discovery rate (FDR) control, according to Benjamini and Yekutieli (2005). Ethanol tolerance assays and reciprocal hemizygosity analysis were carried out as described previously (2012).

Molecular Biology Methods

Yeast cells were transformed with the LiAc/SS-DNA/PEG method (Gietz et al., 1995). Genomic DNA was extracted with PCI [phenol/chlroform/isoamyl-alcohol (25:24:1)
(Hoffman and Winston, 1987). Polymerase chain reaction (PCR) was performed with Accuprime polymerase (Invitrogen) for sequencing purposes and ExTaq (Takara) for diagnostic purposes. Sanger sequencing was performed by the Genetic Service Facility of the VIB. The detection of SNPs by PCR was performed as previously described (Swinnen et al., 2012a).

Reciprocal Hemizygosity Analysis (RHA)

RHA was performed as described previously (Swinnen et al., 2012a; Steinmetz et al., 2002) in the diploid Seg5/BY710 genetic background. In addition to single gene deletions we also performed large deletions (bulk RHA) of regions up to 27 kb long. The selection marker utilized was the amidase gene (AMD1), which was amplified from the vector pF6a-AMD1-MX6. The gene AMD1 was cloned from Z. rouxii (Shepherd and Piper, 2010). The primers utilized in the AMD1 amplification had at least 80 extra bases that corresponded to the flanking regions of the area to be deleted. The transformants were selected on solid YCB+ acetamide 10 mM (yeast carbon base 11.7 g/L; sodium phosphate buffer 0.03 M; agar 20 g/L). The correct integration of the constructs was checked by PCR, using one primer that annealed within AMD1 and two other primers that annealed either downstream or upstream of the deleted region. The PCR products were sequenced and the polymorphisms (SNPs and indels) present in the regions flanking the selection marker were identified when the Seg5 allele was replaced by AMD1. On the other hand, when the laboratory allele was deleted, no polymorphism was detected by Sanger sequencing. Double allele deletion was not observed during the bulk RHA because the deleted regions contained at least one essential gene.

Reproducibility and Statistical Analysis

The fermentations with different yeast strains were done with the reference strain V1116 as a control in duplicate. The most interesting strains were repeated at least once. The fermentations with different meiotic segregants were done with the reference strains Seg5, BY710 and Seg5/BY710. The segregants showing more than 16.5% (v/v) ethanol production were evaluated by fermentation at least once more. The fermentations for RHA were done in triplicate. The results were analyzed with a paired t-test (p<0.01, except for the comparison of V1116 and CBS1585 for which p<0.05 was used).

Data Access

All sequence data have been deposited in the Sequence Read Archive (SRA) at the National Center for Biotechnology Information (NCBI) and can be accessed with account number SRA056812.

Example 1: Strain Selection for Maximal Ethanol Accumulation Capacity

Figure 1:
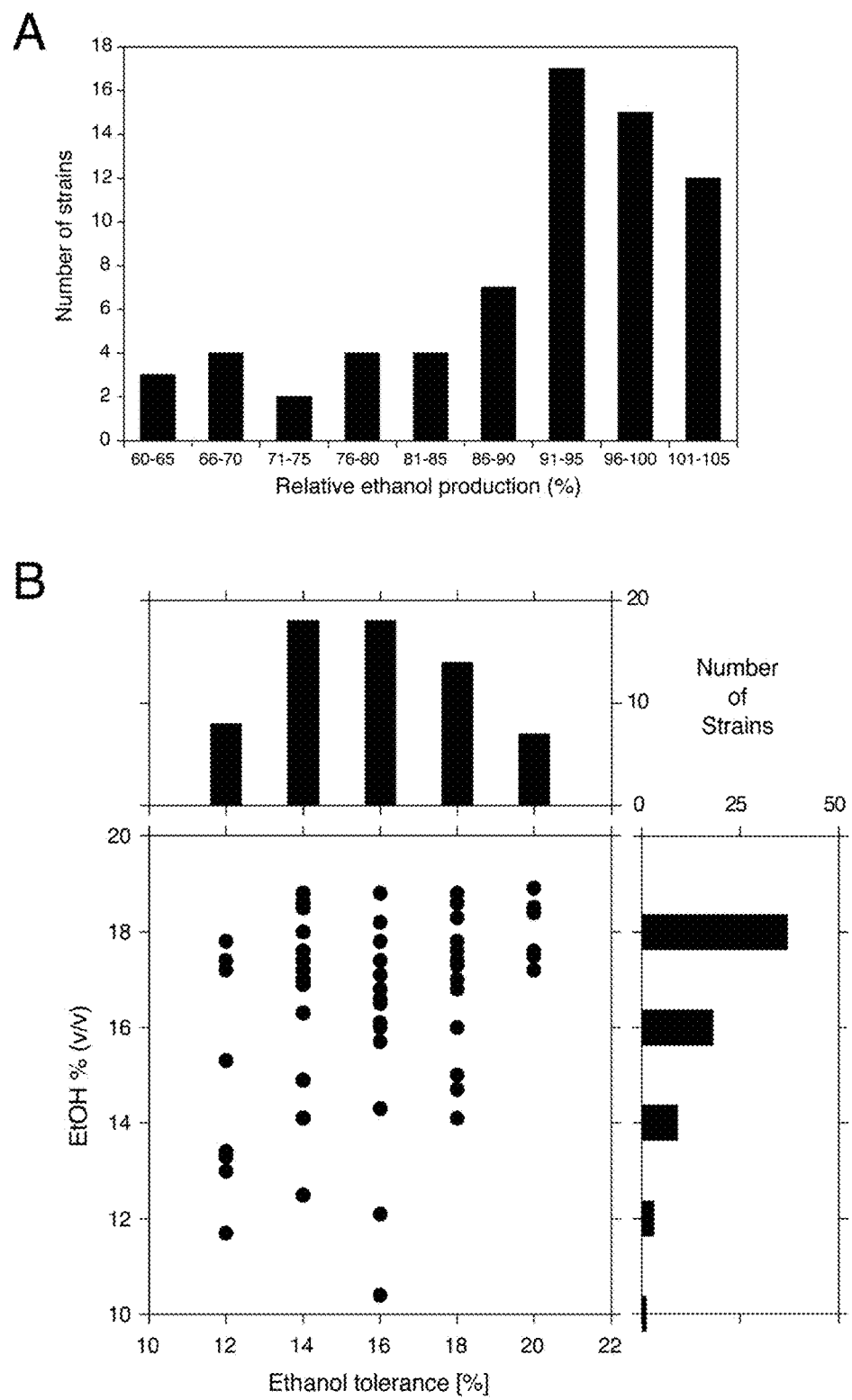
FIG. 1. Maximal ethanol accumulation capacity and ethanol tolerance of cell proliferation in 68 different yeast strains.

We have evaluated 68 different yeast strains in small-scale fermentations for maximal ethanol accumulation capacity under very high gravity (VHG) conditions (Puligundia et al., 2011), using 33% (w/v) glucose. The robust wine strain V1116 was used as reference in each series of fermentation experiments. FIG. 1A shows the number of strains able to accumulate a certain maximal ethanol level expressed as percentage of the ethanol level accumulated by V1116 in the same experiment, which was 18.4±0.4% (v/v). There was no correlation between the final glycerol and ethanol levels produced but there was an inverse correlation between the final glycerol level and the ethanol yield. Table 2 shows the fermentation results for a number of representative strains ranked, according to the maximal ethanol level produced in comparison with the reference V1116.

TABLE 2

Fermentation results for representative strains from the screen of 68 yeast strains. High-gravity, semi-anaerobic, semi-static fermentations were carried out with 250 mL of YP + 33% (w/v) glucose at 25° C.

| Strains | Relative maximal ethanol accumulation (% compared to V1116) | Final ethanol titer (% v/v) | Glycerol titer (g/L) | Ethanol yield* (%) |
|---|---|---|---|---|
| CBS1585 | 103.4 | 18.8 | 10.9 | 88.4 |
| CAT1 | 97.8 | 17.5 | 11.3 | 88.1 |
| CBS6412 | 92.9 | 16.9 | 7.2 | 89.8 |
| CBS2807 | 88.9 | 15.3 | 11.2 | 88.1 |
| S288c | 80.2 | 14.9 | 10.8 | 88.6 |
| CBS1200 | 76.5 | 14.3 | 8.7 | 89.2 |
| CBS382 | 74.7 | 14.1 | 10.8 | 88.4 |
| CMBS33 | 66 | 12.5 | 10 | 88.7 |
| BY4741 | 64.3 | 12.1 | 9.7 | 89.1 |

*Ethanol yield is expressed as percentage of the maximum theoretical ethanol yield (0.51 g ethanol/g glucose consumed).

The fermentation of the reference strain, V1116, took 9.4±1.1 days to complete. The ethanol productivity was 0.65 g.L$^{-1}$.h$^{-1}$ (or 0.83 g.L$^{-1}$.h$^{-1}$ when we omit the last two days where the fermentation had slowed down very much). The productivity was highest during the first three days (1.17 g.L$^{-1}$.h$^{-1}$). The yield was 0.446 g ethanol /g glucose (87.4%). There was 2.20±0.57% (w/v) glucose leftover. Glycerol production was 10.34±0.47 g/L. The final pH was 4.5±0.2 for all strains evaluated. The best ethanol producer was the sake strain, CBS1585, that accumulated 103.4% of the amount of ethanol accumulated by V1116. The relative ethanol production (% compared to V1116), the final ethanol % (v/v), the glycerol yield (g/L) and ethanol yield (% of maximum theoretical yield) for all 68 strains are listed in Table 3.

TABLE 3

Screening of 68 yeast strains in small-scale fermentations for maximal ethanol accumulation (250 mL YP + 33% glucose). Ethanol production is shown in comparison to the robust wine strain V1116 and the strains are listed in descending order of performance. The final ethanol titer (%, v/v), glycerol level (g/L) and ethanol yield (%) are also indicated for each strain. The strains were either evaluated once, twice (*), three times () or six times (*). *Ethanol yield is expressed as percentage of the maximum theoretical ethanol yield (0.51 g ethanol/g glucose consumed).

| Strains | Relative ethanol production (% compared to V1116) | EtOH % (v/v) | Glycerol (g/L) | Ethanol yield (%)* |
|---|---|---|---|---|
| CBS1585 (***) | 103.4 | 18.8 | 10.9 | 88.4 |
| Benvinda (*) | 102 | 18.6 | 11.6 | 88.1 |
| Ethanol Red (**) | 101.9 | 18.5 | 13.1 | 87.7 |
| Eau de Vie (**) | 101.7 | 18.4 | 10.4 | 88.3 |
| Fermivin (**) | 101.7 | 18.8 | 11.2 | 88 |
| Produtor 4 | 101.6 | 17.8 | 11.7 | 88.1 |
| Alcotec 24 (*) | 101.5 | 18.8 | 11.9 | 88 |
| Alcotec 48 (*) | 101.5 | 18.8 | 12 | 87.8 |
| Alcotec 23% (*) | 101.5 | 18.8 | 12.2 | 87.6 |
| Alcotec vodka star (*) | 101.5 | 18.8 | 12.2 | 87.7 |
| Turbo yeast (*) | 101.5 | 18.8 | 12.5 | 87.7 |
| Intek796 (*) | 101.2 | 18.8 | 12.6 | 87.4 |
| Thermosacc Dry (*) | 99.9 | 17.2 | 9.8 | 88.5 |
| CBS7961 | 99.2 | 17 | 10.8 | 88.4 |
| Alcotec triple (*) | 98.9 | 18.2 | 12.6 | 87.5 |
| Zimmerman 814 | 98.9 | 18.5 | 11.5 | 87.9 |
| Monatnhesa Atividade | 98.9 | 17.4 | 11.9 | 87.8 |
| TMB3399 | 98.6 | 18.9 | 10.5 | 88.4 |
| CAT1 (*) | 97.8 | 17.5 | 11.3 | 88.1 |
| Fali S1 | 97.8 | 18 | 12.7 | 87.4 |
| CBS6414 | 97.3 | 16.7 | 10.7 | 88.3 |
| CBS7957 | 97.2 | 18.3 | 13.5 | 87.1 |
| Sake 4134 | 96.3 | 18.6 | 14.5 | 86.8 |
| VR1 (*) | 96.1 | 17.2 | 10.7 | 88.3 |
| PE2 (*) | 96.1 | 17.2 | 11.6 | 88 |
| CBS7960 | 96 | 16.8 | 10.5 | 88.2 |
| Diva | 96 | 16.9 | 9.9 | 88.5 |
| Montanhesa Pe | 94.9 | 17.8 | 13.1 | 87.2 |
| M2 | 94.7 | 17.8 | 11.1 | 87.9 |
| French Red | 93.9 | 17.6 | 7.5 | 89.3 |
| Superstart (*) | 93.7 | 17 | 11.6 | 88 |
| CBS2808 | 93.5 | 16.1 | 10.5 | 88.2 |
| Produtor 3 | 93.4 | 16.5 | 10.9 | 88.2 |
| Sake K11 | 93.3 | 17.1 | 12.8 | 87.6 |
| Sauternes | 93.3 | 17.6 | 11.5 | 88 |
| CBS6413 | 93.1 | 16 | 11.1 | 88 |
| CBS6412 (*) | 92.9 | 16.9 | 7.2 | 89.8 |
| Champagne | 92.5 | 17.4 | 11.8 | 87.8 |
| Zimermman 815 | 92.4 | 17.8 | 11 | 87.9 |
| S. boulardii | 92.4 | 16.3 | 10.64 | 88.2 |
| CBS1198 | 92.2 | 17.4 | 9.8 | 88.7 |
| CBS7764 | 91.9 | 17.3 | 10.5 | 88.6 |
| Fali S2 | 91.3 | 17.2 | 12.1 | 87.9 |
| TMB3400 | 91.3 | 17.6 | 10.63 | 88.4 |
| Cognac | 90.1 | 17.4 | 12 | 87.8 |
| 46EDV (*) | 89.3 | 16.8 | 9.2 | 89.1 |
| CBS2807 | 88.9 | 15.3 | 11.2 | 88.1 |
| CBS1252 | 87.9 | 16.6 | 12.7 | 87.5 |
| CBS7072 | 87.5 | 16.5 | 11.1 | 88.3 |
| CBS7958 | 86.1 | 16.1 | 11.5 | 88.1 |
| CBS1390 | 86 | 16.1 | 9.3 | 89.3 |
| Pasteur Champagne | 85.3 | 16 | 8.7 | 89.4 |
| Port | 83.4 | 15.7 | 10.3 | 88.5 |
| Y55 | 82.6 | 15 | 9.5 | 88.9 |
| S288c (*) | 81.2 | 14.9 | 10.8 | 88.6 |
| Assmanhausen | 79.7 | 15 | 9.5 | 89 |
| CBS7539 | 78.2 | 14.7 | 11.2 | 88.1 |
| CBS1200 | 76.5 | 14.3 | 8.7 | 89.2 |
| Westmalle | 76 | 14.1 | 8.8 | 89.3 |
| CBS1241 | 74.8 | 14.1 | 9.7 | 89 |
| CBS382 | 74.7 | 14.1 | 10.8 | 88.4 |
| GT344 (*) | 69 | 13.4 | 8.8 | 89.4 |
| GT339 (*) | 68.7 | 13.3 | 9.2 | 89.2 |
| GT336 (*) | 67.1 | 13 | 9.1 | 89.2 |
| CMBS33 (*) | 66 | 12.5 | 10 | 88.7 |
| BY4741 (*) | 64.3 | 12.1 | 9.7 | 89.1 |
| CBS422 | 62 | 11.7 | 13.9 | 87.2 |
| CBS436 | 60.8 | 10.4 | 11.6 | 88.2 |

The laboratory strains BY4741 (Matα his3Δ1 leu2Δ0 ura3Δ0 met15Δ0) and S288c (prototrophic) produced only 64% and 80%, respectively, of the ethanol level accumulated by V1116. This is in accordance with previous studies that showed the prototrophic laboratory strain (S288c) to be generally more stress tolerant than its auxotrophic counterpart (BY4741) (Albers and Larson, 2009), although this has not yet been documented for ethanol tolerance. The eight beer strains tested all produced less than 80% of the ethanol produced by V1116, in agreement with the relatively low ethanol levels generally present in beers. On the other hand, strains used for the production of bioethanol and sake were among the best for maximal ethanol accumulation, which fits with the high level of ethanol produced in these industrial fermentations (Basso et al., 2010; Watanabe et al., 2009).

Cell viability at the end of the fermentation was lower than 10%, and usually only 1-5%, for all strains tested, except for Ethanol Red and CBS1585. The bioethanol production strain Ethanol Red retained 22.1%±4.1% viable cells and the sake strain, CBS1585, even 31.5%±5.1%. The latter strain also showed the highest ethanol accumulation among all strains evaluated. High ethanol production is a well-known trait of sake strains (Kodama, 1993). The high residual viability is remarkable in view of the 18-19% of ethanol accumulated. The ethanol level could be enhanced further by applying continuous stirring (200 rpm) and raising the glucose concentration to 35%. In this case, ethanol levels between 20 and 20.5% (v/v) were routinely obtained, with an absolute maximum of 20.9% (v/v). In six consecutive fermentations with the same cells under these conditions, 20.5% ethanol was accumulated in the first fermentation and 16.5-19.5% ethanol (v/v) in the subsequent fermentations, demonstrating the persistent viability of strain CBS1585 under high ethanol conditions.

We have compared the maximal ethanol accumulation capacity with the ethanol tolerance of cell proliferation in the 68 strains. The results are summarized in FIG. 1B. They show that most strains with a low ethanol tolerance of cell proliferation also displayed poor maximal ethanol accumulation and that none of these strains reached a final ethanol titer of more than 18% (v/v). Strains with a higher ethanol tolerance of cell proliferation tended to produce higher maximal ethanol levels. This was most pronounced in the strains able to grow in the presence of 20% ethanol on plates. All of these strains showed high maximal ethanol accumulation and 50% produced a final ethanol level higher than 18% (v/v). On the other hand, the general correlation between the two traits showed only weak significance (Spearman one-tailed test: 90% confidence interval, P-value=0.0984). This suggested that the genetic basis of the two traits was at least partially different.

Example 2: Isolation of a Superior Segregant of CBS1585

The diploid sake strain CBS1585 was sporulated and stable mating type a and α segregants were obtained indicating heterothallism of the parent strain. Ten segregants were phenotyped in small-scale VHG semi-static fermentations. A segregant, Seg5 (MATa), was identified, which showed the same fermentation profile (FIG. 2A) and maximal ethanol accumulation capacity as its parent strain, CBS1585 (FIG. 2B). The laboratory strain BY710 (derived from BY4742; same genotype: Matα his3Δ1 leu2Δ0 ura3Δ0 lys2Δ0) showed a lower fermentation rate and also a much lower maximal ethanol accumulation capacity, which was only around 12% (v/v) (FIGS. 2A and 2B). The a mating type of the Seg5 strain was stable and FACS analysis confirmed that its DNA content was half that of its diploid parent CBS1585 (data not shown). We have crossed Seg5 with BY710 to obtain the diploid Seg5/BY710, which showed a similar high fermentation rate (FIG. 2A) and high ethanol accumulation capacity (FIG. 2B) as the original CBS1585 diploid strain. Growth assays on solid media, with or without glucose, and containing different levels of ethanol, showed that CBS1585, Seg5 and Seg5/BY710 had a similar ethanol tolerance of cell proliferation whereas the laboratory strain (BY710) was much more sensitive (FIG. 2C). These results indicate that the two ethanol tolerance traits are dominant characteristics in the strain backgrounds used.

Example 3: Comparison Between Ethanol Tolerance of Cell Proliferation on Solid Nutrient Plates and Maximal Ethanol Accumulation Capacity in Fermentation We have investigated whether ethanol tolerance as determined by the classical assays of cell proliferation on solid nutrient plates containing different levels of ethanol, correlates with maximal ethanol accumulation capacity in fermenting cells in the absence of cell proliferation. For that purpose, Seg5 was crossed with BY710, the Seg5/BY710 diploid sporulated and the segregants were first plated on solid media containing glucose and/or ethanol (18% to 20% v/v). FIG. 3A shows a representative result. The haploid parent Seg5 showed high tolerance of cell proliferation to ethanol whereas the laboratory strain BY710 was much more ethanol sensitive. Among the segregants we could observe some with very high ethanol tolerance (e.g., Seg 11C), some with intermediate tolerance (e.g., Seg 10A) and others that were as ethanol sensitive as the laboratory strain (e.g., Seg11D). Out of 301 segregants evaluated in this way, 101 segregants showed moderate to high ethanol tolerance, whereas about half of the segregants (48.8%) could not grow at all on plates containing 18 or 20% ethanol (v/v). In the first category, 32 segregants showed an ethanol tolerance level as high as Seg5. Hence, about 1 in 9 segregants showed the same high ethanol tolerance as the superior parent. If we suppose random segregation of the loci and no epistasis, this ratio predicts three independent loci as being involved in determining the high ethanol tolerance of Seg5 compared to the laboratory strain BY710.

Subsequently, we tested 15 ethanol sensitive segregants (similar to Seg11D of FIG. 3A) by fermentation in 250 mL of YP+33% (w/v) glucose. All 15 segregants clearly showed poor fermentation performance, with a low ethanol accumulation capacity (<14% v/v) (not shown). This suggests that there is a correlation between ethanol tolerance as measured by the cell proliferation assays on solid nutrient plates and maximal ethanol accumulation capacity in VHG fermentation, at least for the ethanol sensitive strains. Hence, to reduce the high workload required for phenotyping all segregants in fermentations, we tested in the small-scale fermentations only the 101 segregants that showed moderate to high ethanol tolerance in the growth assays on solid nutrient plates. We are aware that the strains with poor ethanol tolerance of cell proliferation may contain mutant genes that compromise maximal ethanol accumulation capacity or that when these strains show relatively high maximal ethanol accumulation capacity, they may contain (in part) different mutant alleles than the strains with high ethanol tolerance of cell proliferation. The main purpose of this work, however, was to identify the first set of major causative genes determining maximal ethanol accumulation capacity and this is the main reason why we continued first with the strains preselected for medium to high ethanol tolerance of growth.

The distribution of maximal ethanol accumulation capacity among the 101 segregants, as tested in semi-static small-scale fermentations in 250 mL of YP+33% (w/v)

glucose, is shown in FIG. 3B. Only 22 segregants produced ethanol titres higher than 17% (v/v), similar to the ethanol production of Seg5 and Seg5/BY710. If we assume that all ethanol sensitive segregants, as determined by growth assays on solid nutrient plates, also display poor maximal ethanol accumulation, we have a ratio of one superior strain in ±14 segregants (301/22=13.7). Assuming random segregation of the QTLs and no epistasis, this ratio is consistent with four independent loci being responsible for the superior ethanol accumulation capacity of Seg5 compared to the BY710 control strain. We constructed several diploids by crossing the four best performing segregants but none of those showed higher ethanol accumulation capacity than the original CBS1585 diploid strain (data not shown).

Example 4: QTL Mapping by Pooled-Segregant Whole-Genome Sequence Analysis.

We have performed genetic mapping of the two polygenic traits: on the one hand, high ethanol accumulation capacity in fermenting cells in the absence of cell proliferation, using the 22 best-performing segregants (pool 1) as determined in semi-static VHG fermentations, and on the other hand, tolerance of cell proliferation to high ethanol levels, using the 32 segregants (pool 2) that showed the best growth on solid nutrient media containing 18 to 20% (v/v) ethanol. Identification of the QTLs was performed by pooled-segregant whole genome sequence analysis (Swinnen et al., 2012a; Liti and Louis, 2012; Ehrenreich et al., 2010; Parts et al., 2011). Genomic DNA was sent for custom whole-genome sequence analysis by the Illumina platform, to two independent companies (GATC Biotech, Konstanz, and BGI, Hong Kong). The sequencing parameters are summarized in the Methods section. Sequence analysis of the genome of the superior parent Seg5 and comparison to S288c, allowed us to select 48,512 high-quality SNPs after filtering for sufficient coverage (≥20 times) and ratio (≥80%) (Swinnen et al., 2012a; Claesen et al., 2013). The coverage of at least 20 times was based on previous findings that a 20-fold sequencing coverage is sufficient to compensate for errors by the number of correct reads (Dohm et al., 2008). The ratio of at least 80% was chosen based on the plots of the SNPs between the two parent strains, as described previously (Swinnen et al., 2012a). We also mapped the reads to the assembled sequence for the Kyokai n°7 strain available in the *Saccharomyces* genome database (Akao et al., 2011). We were able to map about 20,000 additional reads to this sequence and 93% of the total read pairs aligned with proper distance and orientation to the Kyokai n°7 assembly, while only 87% of the read pairs mapped in the same way to S288c. We also identified the sake strain specific genes AWA1 and BIO6 (Akao et al., 2011), which further confirmed that CBS1585 belongs to the sake cluster of *S. cerevisiae* strains.

Genomic DNA was extracted from the two selected pools, containing 22 and 32 segregants, respectively, and also from an unselected pool, composed of 237 segregants (pool 3) in order to assess proper segregation of all chromosomes and possible links to inadvertently selected traits, such as sporulation capacity or spore viability. After sequence analysis, the SNP variant frequency was plotted against the chromosomal position (FIG. 4). Upward deviations from the mean of 0.5 identify QTLs linked to the superior parent Seg5 while downward deviations identify QTLs linked to the inferior parent BY710. The independent sequence analysis by the two different companies produced very similar results, which confirms the robustness of the pooled-segregant whole-genome sequencing technology. The raw sequencing data were smoothed using a Linear Mixed Model (LMM) framework (Swinnen et al., 2012a) and the putative QTLs were identified by applying a Hidden Markov Model (HMM) similar to the one implemented in the FastPHASE package (Sheet and Stephens, 2006). For each polymorphism, the HMM had three possible states: (i) a link with the superior parent (Seg5), (ii) a link with the inferior parent (BY710) and (iii) no link (background level). The SNP frequencies for each pool of segregants, analyzed with the HMM, were assigned probability scores, that indicated to which state (Seg5, BY710 or background) they belonged and hence identified the QTLs, linked to either the superior parent (Seg5) or to the inferior parent (BY710).

The smoothed data of the SNP variant frequency and the probability of linkage values obtained by HMM analysis with the selected pools 1 and 2 and the unselected pool 3, are shown in FIG. 4. The QTLs identified with the HMM approach are listed in Tables 4 and 5 for pools 1 and 2, respectively. SNPs were considered significantly linked to the superior or inferior parent strain when the probability of linkage was higher than 0.95 or lower than −0.95, respectively. The QTLs were numbered, according to their position in the genome, starting from chromosome I, independently of the trait (Tables 4 and 5).

TABLE 4

QTLs identified for maximal ethanol accumulation capacity (pool 1, 22 segregants) by pooled-segregant whole-genome sequencing. Eight QTLs were associated with the genome of the superior parent Seg5 and three QTLs linked to the genome of the inferior parent BY710. The chromosomal position of each QTL, the number of SNPs with significant linkage and the average probability of linkage of all significant SNPs in the QTL are indicated. All QTLs indicated had a significant probability of linkage >0.95 when linked to the Seg5 parent or <−0.95 when linked to the BY parent. QTLs 1, 6, 11, 14, 15 and 16 were found only in pool 2 (see Table 5) whereas QTLs 12 and 17 were common for both pools and designated 12.1 and 12.2 or 17.1 and 17.2 depending on the pool.

| QTL | Chr. | Genomic position (bp) | Nr. SNPs with significant linkage | Average Probability of linkage | Association with parent | Presence in pool 2 |
|---|---|---|---|---|---|---|
| 2 | I | 168455-179051 | 30 | 0.996868 | Seg5 | No |
| 3 | V | 69939-166080 | 348 | 0.999346 | Seg5 | No |
| 4 | V | 178671-198538 | 84 | 0.999191 | Seg5 | No |
| 5 | V | 230340-269314 | 187 | 0.997819 | Seg5 | No |
| 7 | X | 136210-175751 | 148 | −0.986817 | BY | No |
| 8 | X | 288210-321763 | 107 | 0.999024 | Seg5 | No |
| 9 | X | 486491-594119 | 230 | 0.99672 | Seg5 | No |
| 10 | XII | 1022570-1053429 | 94 | −0.999094 | BY | Weak |
| 12.1 | XIII | 109860-137864 | 47 | 0.994056 | Seg5 | Yes |
| 13 | XIII | 346583-352695 | 27 | 0.991967 | Seg5 | Weak |
| 17.1 | XV | 372007-494421 | 247 | −0.999883 | BY | Yes |

TABLE 5

QTLs identified for tolerance of cell proliferation to high ethanol (pool 2, 32 segregants) by pooled-segregant whole-genome sequencing. There are six QTLs linked to the genome of the superior parent Seg5 and two QTLs linked to the genome of the inferior parent BY710. The chromosomal position of each QTL, the number of SNPs with significant linkage and the average probability of linkage of all significant SNPs in the QTL are indicated. All QTLs indicated had a significant probability of linkage >0.95 when linked to the Seg5 parent or <−0.95 when linked to the BY parent. QTLs 2, 3, 4, 5, 7, 8, 9, 10 and 13 were found only in pool 1 (see Table 4) whereas QTLs 12 and 17 were common for both pools and designated 12.1 and 12.2 or 17.1 and 17.2 depending on the pool.

| QTL | Chr. | Genomic position (bp) | Nr. SNPs with significant linkage | Average probability of linkage | Association with parent | Presence in pool 1 |
|---|---|---|---|---|---|---|
| 1 | I | 29970-55793 | 83 | −0.998124 | BY | Weak |
| 6 | VII | 585062-600706 | 50 | 0.99851 | Seg5 | Weak |
| 11 | XIII | 43152-51596 | 37 | 0.97562 | Seg5 | Weak |
| 12.2 | XIII | 79761-173678 | 183 | 0.998144 | Seg5 | Yes |
| 14 | XIV | 525370-549448 | 70 | 0.997764 | Seg5 | No |
| 15 | XV | 161704-184072 | 59 | 0.997942 | Seg5 | Weak |
| 16 | XV | 205844-210327 | 26 | 0.970977 | Seg5 | Weak |
| 17.2 | XV | 356119-487809 | 285 | −0.99949 | BY | Yes |

The unselected pool 3 (237 segregants) showed ±50% SNP variant frequency in most of the genome and thus no evidence of any QTLs (FIG. 4). The only exception was the right arm of chromosome V which was preferentially inherited from the BY parent strain. Comparison with the data of the selected pools, suggested some weak linkage with the genome of the BY parent strain in this part of chromosome V. Because of the weak linkage this was not retained for further analysis. Crosses of Seg5 with other BY strains did not show aberrant segregation of the right arm of chromosome V (results not shown). The results obtained with the unselected pool show that the QTLs identified for the two ethanol tolerance traits were not due to linkage with inadvertently selected traits, such as sporulation capacity or spore viability.

The QTLs identified with the selected pools 1 and 2 showed two common QTLs (on chr XIII and chr XV). They were called 12.1 and 17.1 for pool 1 and 12.2 and 17.2 for pool 2. It has to be emphasized that the "common" character of these QTLs is only based on their common location in the genome. In principle, they could be located in the same place on a chromosome but caused by a different causative gene. Moreover, the QTLs 15 and 16 (pool 2) were also present in pool 1 as minor putative QTL of which the significance could not be demonstrated with the current number of segregants (probability of linkage<0.95). Other minor putative QTLs of which the significance could not be demonstrated with the current number of segregants (probability of linkage<0.95) were present in pool 1 and pool 2. They were also evident from the smoothed data and the HMM analysis (FIG. 4) (e.g., on chromosome VII). These loci might contain genes that contribute to some extent to ethanol tolerance but are not essential for maximal ethanol tolerance of cell proliferation or for maximal ethanol accumulation in fermentation under the conditions and the stringency that we applied. Alternatively, they can contain alleles with an important contribution to high ethanol tolerance but which are redundant with one or more other alleles. If the different alleles have no additive effect, the presence of one allele suffices and its QTL will always remain a minor QTL, whatever the stringency applied in phenotyping.

Example 5: Identification of Causative Genes in QTLs of Pool 1

We have analyzed in detail two QTLs (2 and 3) involved in high ethanol accumulation capacity (pool 1) because this trait is more relevant in industrial fermentations and because these two QTLs were among those with the strongest linkage. QTL2 is located on chromosome I and was fine-mapped by scoring selected markers in the 22 individual segregants. This reduced the length of the QTL to the area between chromosomal positions 151 kb and 178 kb (P-value<0.05) (FIG. 5A). The association percentage of the markers, their genomic positions, the respective P-values and the genes located in the putative QTL 1 are shown in FIG. 5A.

Nearly all genes present in the center of the QTL had at least on polymorphism either in the ORF, promotor or terminator. Hence, it was not possible to exclude on this basis a significant number of genes as candidate causative genes. Because of the large number of candidate genes and the high workload of the phenotyping for maximal ethanol accumulation capacity, we have introduced a modification of the Reciprocal Hemizygosity Analysis (RHA) methodology, which has been used previously for identification of causative genes (Steinmetz et al., 2002). Instead of testing one candidate gene at a time, we first evaluated a series of adjacent genes by "bulk RHA." For that purpose a set of adjacent genes was deleted directly in the heterozygous diploid background (Seg5/BY710) so as to obtain the two reciprocally deleted hemizygous diploids of which the phenotype was subsequently compared. The first block of genes (bRHA 1.1) deleted, consisted of NUP60, ERP1, SWD1, RFA1 and SEN34. The two reciprocally deleted diploid strains were tested by fermentation in YP+33% (w/v) glucose, to address the effect of the Seg5 and BY710 alleles on ethanol accumulation capacity. The results showed no difference in the fermentation profile and maximal ethanol accumulation (FIG. 5B), suggesting that none of these five genes were causative genes. There was also no difference in fermentation profile and maximal ethanol accumulation with the hybrid parent strain Seg5/BY710, further supporting that these genes did not influence these phenotypes.

The second block of genes tested consisted of YARCdelta3/4/5, YARCTy1-1, YAR009c, YAR010c, tA(UGC)A, BUD14, ADE1, KIN3 and CDC15 (bRHA 1.2) (FIG. 5A). In this case there was a clear reduction of the fermentation rate and maximal ethanol accumulation when the alleles of the Seg5 strain were absent compared to absence of the BY710 alleles (FIG. 5C). Glucose leftover correlated inversely with final ethanol titer. This suggested the presence of one or more causative genes in this region. Moreover, the fermentation rate was higher in the hemizygous strain where the BY710 alleles were absent compared to the hybrid parent strain Seg5/BY710, indicating that one or more of the BY710 alleles had a negative effect on this phenotype.

YARCdelta3/4/5, YARCTy1-1, YAR009c and YAR010c are transposable elements, while tA(UGC)A encodes one of the sixteen tRNAs for the amino acid alanine. BUD14 is involved in bud-site selection (Cullen and Sprague, 2002), ADE1 is involved in de novo purine biosynthesis (Myasnikov et al., 1991), KIN3 encodes a non-essential serine/threonine protein kinase involved in a.o. DNA damage repair (Moura et al., 2010) and CDC15 encodes a protein kinase involved in control of the cell division cycle ((Bardin et al., 2003). In order to identify the genes(s) involved in ethanol accumulation capacity, we investigated the most likely candidate genes individually with the classical one-gene RHA (Steinmetz et al., 2002). Involvement of the transposable elements appeared unlikely and was not evaluated by RHA. The other genes, BUD14, ADE1, KIN3 and CDC15, have polymorphisms (SNPs and/or indels) within their ORFs and/or promoter regions. RHA with the genes ADE1 and KIN3 showed that deletion of the Seg5 alleles resulted in strains with clearly lower ethanol accumulation capacity and higher glucose leftover compared to the strain with deletion of the respective BY allele, indicating that ADE1 and KIN3 are causative genes for high ethanol accumulation capacity in Seg5 (FIG. 6A). For both genes, the hybrid parent strain Seg5/BY710 behaved in a similar way as the strain with the deleted BY710 allele. For CDC15 and BUD14 there was no difference in the performance of the two reciprocally deleted diploid strains (not shown). Deletion of ADE1 and KIN3 in the Seg5 and BY backgrounds caused a more pronounced effect in the Seg5 sake genetic background (FIG. 6B).

The causative genes ADE1 and KIN3 were located in QTL2, which was not linked with ethanol tolerance of cell proliferation. When we tested the hybrid diploid strains previously used in RHA for maximal ethanol accumulation for determination of ethanol tolerance of cell proliferation, we could indeed not observe any significant difference between the two strains (FIG. 6C). This confirms that these causative genes are specific for maximal ethanol accumulation capacity and that the genetic basis of the two ethanol tolerance traits is indeed partially different.

We also analyzed in more detail QTL3, located on chromosome V. In the same chromosomal region, Swinnen et al., 2012a, previously identified URA3 as a causative gene in tolerance of cell proliferation to high ethanol levels of VR1, a Brazilian bioethanol production strain, in comparison with BY4741 as inferior parent strain. Since we crossed Seg5 with an ura3 auxotrophic laboratory strain (BY710), we first tested whether deletion of URA3 in Seg5 affected maximal ethanol accumulation in this genetic background. The fermentation profile and maximal ethanol accumulation of the strain Seg5-ura3Δ/BY710-ura3Δ (which is thus homozygous for ura3Δ) compared with the Seg5/BY710-ura3Δ diploid (which is heterozygous for ura3Δ) are shown in FIG. 7A. Double deletion of URA3 resulted in a strain with a reduced ethanol fermentation rate, lower maximal ethanol accumulation and higher glucose leftover. We have also tested the effect of introducing URA3 in the ura3 auxotrophic strain BY4741, which accumulates only low amounts of ethanol under VHG conditions (±12% v/v). Introduction of URA3 enhanced the fermentation rate in the later stages of the fermentation and resulted in a clearly higher maximal ethanol titer and lower glucose leftover (FIG. 7B). These results show that URA3 positively affects maximal ethanol accumulation capacity. The URA3 gene was located in QTL3, which was not significantly linked with ethanol tolerance of cell proliferation. When we tested the hybrid diploid strains previously used in RHA for maximal ethanol accumulation for determination of ethanol tolerance of cell proliferation, we observed slightly better growth for the strain with the URA3 allele from Seg5 (FIG. 7C). This confirms that URA3 has only a minor contribution to this phenotype in this genetic background and suggests that the very weak upward deviation in the SNP variant frequency plot observed in this position for ethanol tolerance of cell proliferation might have been due to the URA3 gene.

Example 6: Occurrence of the SNPs in the Causative Genes ADE1 and KIN3 in Other Yeast Strains Comparison of the sequence of ADE1 and KIN3 in Seg5 and BY710 (S288c background) revealed a C to T transition in the promoter of ADE1 and a C to T transition in the promoter of KIN3 as well as three synonymous transition mutations in the ORF of KIN3. We have checked the presence of these SNPs in the ADE1 and KIN3 genes of 36 yeast strains of which the whole genome sequence has been published. The results are shown in Table 6. (Among the 36 strains there were additional SNPs compared to S288c, which were not present in Seg5. These SNPs are not shown). The C to T change at position 169227 in ADE1 is present only in two other strains, Kyokai nr. 7 and UC5. Both strains are sake strains and these strains are known to have superior maximal ethanol accumulation capacity. Sake fermentation produces the highest ethanol level of all yeast fermentations for production of alcoholic beverages (Kodama, 1993). The SNPs in KIN3 of Seg5 at positions 170564 and 170945 are present in many other strains. Interestingly, however, the two other SNPs in KIN3 of Seg5, at positions 170852 (in the ORF) and 171947 (in the promoter) are not present in KIN3 of any one of the 36 sequenced strains and, therefore, may be rather unique.

TABLE 6

Occurrence of the SNPs in the causative genes ADE1 and KIN3 in other yeast strains. The SNPs present in Seg5 compared to S288c were checked in 36 strains of which the whole genome sequence has been published. (SNPs present in the other strains compared to S288c, but not in Seg5, are not indicated).

| | | SNP | | | | |
|---|---|---|---|---|---|---|
| | | ADE1 | KIN3 | | | |
| | | Prom. | | ORF | | Prom. |
| | | 169227 | 170564 | 170852 | 170945 | 171947 |
| BY710 (~BY4742) | This study | C | G | C | A | C |
| Seg5 (sake) | This study | T | A | T | G | T |
| Kyokai no. 7 (sake) | BABQ01000003 | T | G | C | A | C |
| EC9-8 | AGSJ01000959 | C | G | C | A | C |
| Lalvin_QA23 | ADVV01000003 | C | A | C | A | C |
| VIN13 | ADXC01000003 | C | A | C | A | C |
| JAY291 | ACFL01000304 | C | A | C | A | C |

TABLE 6-continued

Occurrence of the SNPs in the causative genes ADE1 and KIN3 in other yeast strains. The SNPs present in Seg5 compared to S288c were checked in 36 strains of which the whole genome sequence has been published. (SNPs present in the other strains compared to S288c, but not in Seg5, are not indicated).

| | | SNP | | | | |
|---|---|---|---|---|---|---|
| | | ADE1 | KIN3 | | | |
| | | Prom. | ORF | | | Prom. |
| | | 169227 | 170564 | 170852 | 170945 | 171947 |
| L1528 | Liti et al., 2009 | C | A | C | A | C |
| ForstersB* | AEHH01000001 | C | G  A | C | A | C |
| Forsters0 | AEEZ01000002 | C | G | C | A | C |
| AWRI 1631 | ABSV01000027 | C | A | C | A | C |
| AWRI 796 | ADVS01000002 | C | A | C | A | C |
| UC5 (sake) | AFDD01000983 | T | G | C | A | C |
| YPS128 | Liti et al., 2009 | C | A | C | A | C |
| T7 | AFDE01000131 | C | A | C | G | C |
| YJSH1 | AGAW01000003 | C | G | C | G | C |
| ZTW1 | AMDD01000002 | C | G | C | A | C |
| Y12 | Liti et al., 2009 | C | G | C | G | C |
| VL3 | AEJS01000003 | C | A | C | A | C |
| CBS 7960 | AEWL01000708 | C | A | C | A | C |
| T73 | AFDF01002558 | C | A | C | A | C |
| DBVPF1106 | Liti et al., 2009 | C | A | C | A | C |
| PW5 | AFDC01000005 | C | G | C | G | C |
| Sigma1278b | ACVY01000029 | C | G | C | G | C |
| RM11-1a | AAEG01000015 | C | A | C | A | C |
| CEN.PK113-7D | AEHG01000254 | C | G | C | A | C |
| Y55 | Liti et al., 2009 | C | G | C | G | C |
| W303 | ALAV01000008 | C | G | C | A | C |
| SK1 | Liti et al., 2009 | C | G | C | G | C |
| UWOPS83-787_3 | Liti et al., 2009 | C | A | C | G | C |
| UWOPS03-461.4 | Liti et al., 2009 | C | A | C | A | C |
| UWOPS87-2421 | Liti et al., 2009 | C | G | C | G | C |
| DBVPG1373 | Liti et al., 2009 | C | A | C | A | C |
| DBVPG6044 | Liti et al., 2009 | C | G | C | G | C |
| DBVPG6765 | Liti et al, 2009 | C | A | C | A | C |
| YJM789 | AAFW02000160 | C | A | C | A | C |
| YJM975 | Liti et al., 2009 | C | A | C | A | C |
| YJM269 | AEWN01000622 | C | A | C | A | C |
| BY710 variant | | 34 | 15 | 36 | 26 | 36 |
| Seg5 variant | | 2 | 20 | 0 | 10 | 0 |

*The strain ForstersB is heterozygous and has both variants.

Example 7: Application of EXPLoRA

We applied our model to the data described in Swinnen et al., 2012a, who identified two regions linked to high ethanol tolerance in yeast (tolerant to 16% ethanol), that were further validated through identification of the causative genes by reciprocal hemizygosity analysis. The first region (QTL3) encompasses a gene cluster on chromosome XIV between coordinates 466 000 and 486 000, containing the experimentally validated causative genes MKT1 and APJ1. The second region QTL1, containing URA3 as causative gene, is located on chromosome V between coordinates 116 000 and 117 000.

In the original paper of Swinnen et al., 2012a, QTL1 and QTL3 were fine-mapped through a more accurately assessment of the extent to which selected marker sites in the identified QTLs are linked to the phenotype by testing their relative variant frequency in a larger number of segregants than what is sampled during the high throughput sequencing. This allows better approximating the size (number of nucleotides) of the linked region to the minimum that is supported by the resolution of the BSA.

We used this positive set of linked QTLs and the refined delineation of the linked region in these QTLs to test the effect of altering parameter settings on modeling the dependencies between neighboring marker sites with EXPLoRA: more specifically we varied aP (5, 10, 20, and 50) given a fixed value of βP, as the ratio between αP and βP determines the extent to which the effect of the dependency between neighboring marker sites (linkage disequilibrium) is taken into account.

EXPLoRA predicts the posterior probability of marker sites linked to the phenotype on chromosome XIV (QTL3) for different values of αP. For this strongly linked QTL, causative marker sites located in regions that are truly linked to the phenotype of interest always get prioritized, irrespective of the choice of αP (as can be seen by the high posterior probabilities at their respective marker sites: >0.95). However, gradually increasing αP values gives rise to more peaked and less well defined linked regions, because at high values of αP only marker sites with relative variant frequencies close to 1 get high posterior probabilities and the effect of "neighboring markers" on increasing the probability of a neighboring marker site to also belong to a phenotype-linked region becomes marginal. We choose in our analysis αP=10, as with this value we best approximated the experimentally fine-mapped phenotype linked region of QTL3 (Swinnen et al., 2012a).

For benchmarking we compared the performance of our method with that of, respectively, SHOREmap (Schneeberger et al., 2009), a method that has been customarily used for BSA, as well as the novel statistical model for BSA described in the paper of Swinnen et al., 2012a, because both methods were developed for a very similar set up as the one used in this study. Like our HMM model, both methods cope with spurious deviations in variant frequencies by averaging out the observed variant frequencies of neighboring sites. The SHOREmap model does so by defining the concept of windows: each chromosome is divided in overlapping sliding windows of a user-defined length. A score is assigned to each window using the variant counts of all marker sites contained in the window. To obtain normalized scores for the different windows between −1 and 1, the raw score of each window is divided by the score of the window that displays the highest bias towards the variant from the superior parent. Normalized scores approximate 1 when the variant counts in the window display a bias towards the variant of the superior parent, −1 if the bias is towards the variant of the inferior parent and 0 if no bias towards either parent is observed. Spurious variant biases at marker sites located in windows not linked to a phenotype of interest are expected to get canceled out.

The statistical model applied by Swinnen et al., 2012a, on the other hand, deals with spurious biases in variant frequencies by fitting smoothing splines (a sufficiently smooth piecewise-polynomial function (Bartels et al., 1987)) to the input data. After smoothing, a binomial test is applied at each marker site with a correction for multiple testing.

To quantitatively assess the performance of the different methods, we defined as a true positive prediction any marker site that was predicted to be linked to the phenotype of interest by our method that was also located in or close to one of the two regions experimentally shown to be linked to high ethanol tolerance (QTL1, QTL3). We defined as close all regions located either 80 kb upstream or downstream of the causative gene, since scoring of selected, single marker sites in the individual segregants by PCR amplification (fine-mapping) revealed variant counts biasing towards the superior parent in the positively linked QTLs for this physical range (Swinnen et al., 2012a).

The number of true negatives is more difficult to estimate because only the two regions with most pronounced signals in the data were subjected to experimental validation. Since some other regions might also contain causative mutations and thus qualify as true positive QTLs, we cannot assume that all of the non-verified regions are false positives. To estimate the false positive rate we used a method described by Tusher et al., 2001. For a given set of parameter settings (see materials and methods) we ran each method on both the selected (tolerant to 16% ethanol) and the unselected pool. In the unselected pool, which can be considered as a randomized version of the selected pool, all predictions are by definition false positives. Hence, we can estimate the false positive rate as the number of predictions from the unselected pool (number of predictions that pass the chosen cut-off on the linkage score in the unselected pool) divided by the number of predictions in the selected pool (where both the predictions on the selected and unselected pools were obtained with the same parameter settings and cut-off settings). We assumed that we can estimate the number of falsely linked marker sites amongst the total number of predicted marker sites in the selected pool from the predictions made in the unselected pool, because both pools are similar in size. Results of this analysis were obtained with a range of different cut-off settings for each method (0.9 to 0.0, decrement step of 0.1). To allow for a fair comparison, we used for each method the parameters that resulted in the best performance on the positive set (see materials and methods, i.e., αP=10 for EXPLoRA; window size=250 kb and window step =10 kb for SHOREmap, a window size of 40 kb for the method of Swinnen et al., 2012a). The results show that the statistical model of Swinnen et al., 2012a, behaves quite conservative: it achieves a low false positive rate of predicting linked marker sites for the whole range of assayed cut-offs, but at the expense of a low sensitivity. On the other hand, SHOREmap reaches high sensitivities, but at the cost of a high false positive rate. Of all three tested methods, EXPLoRA yields the best compromise between sensitivity and false positive rate.

The observed differences amongst the three algorithms can also be deduced from the linkage score distributions along the genome that each method produces on the positive dataset (i.e., in the neighborhood of QTL1 and QTL3). EXPLoRA and the statistical model used in Swinnen et al., 2012a, both produce block-like signals that correspond well to the notion of linked "recombination blocks." However, the statistical model of Swinnen et al., 2012a, produces a sharper signal than EXPLoRA with an almost binary behavior, explaining its lower sensitivity. The behavior of SHOREmap signals is less "block-like," but more peaked with a rather high base line explaining its higher false positive prediction rate. All three methods were able to prioritize the experimentally validated region on chromosome XIV (QTL3) at a relatively stringent setting. Prioritizing the region on chromosome V containing the gene URA3 (QTL1) seemed less trivial. In the case of SHOREmap, this required reducing the stringency on the cut-off of the linkage score to such extent (below 0.7) that the false positive rate at the level of the marker sites becomes larger than 0.4. With the cut-off on the linkage score used in the original paper (≥0.9), the method used by Swinnen et al., 2012a, failed to detect QTL1. With EXPLoRA, we could reliably identify the region on QTL1 with the same stringent cut-off as we used for identifying QTL3 and thus with the same low false positive rate.

The beneficial effect of explicitly modeling the dependency between neighboring sites on the performance of the model is also illustrated by the results obtained with EXPLoRA when the values of the recombination parameter r are gradually increased. Indeed that when treating neighboring marker sites more independently by increasing r, the accuracy of the predictions drops (lower sensitivity with higher false positive rate, here evaluated again at the level of marker sites).

Example 8: Effect of Modeling the Dependency Between Neighboring Sites on the Analysis of Small Pools The beneficial effect of using the dependency between neighboring sites when analyzing the results of a BSA is expected to be more pronounced when the number of segregants is low. The reasons are that, on the one hand, the effect of linkage disequilibrium is more pronounced (less recombinations have occurred) and the "block-like behavior" is truly present in the data. On the other hand, the higher power obtained through modeling the effects of linkage disequilibrium partly offsets the disadvantages of having fewer segregants (e.g., lower signal to noise ratio and loss of statistical power if linkage scores depend on the number of segregants). To simulate this situation of having less segregants, we sampled random subsets of 20, 40, 60 and 80% of the alignments coming from the segregant pool that was selected for high ethanol tolerance (16%). Since the total average sequencing coverage obtained in the original experiment was 55, much lower than the number of segregants in the pool (136), the sequence data reflects the sampling of maximally 55 different segregants, so that our experiments simulates the use of sequence data derived from maximally 11, 22, 33, and 44 segregants, respectively. We recalculated the allele counts for each marker and analyzed the data using EXPLoRA. Only when the sequencing coverage was drastically reduced to 20% of the original average coverage, the accuracy drops considerably (higher false positive rate for the same sensitivity).

Example 9: Additional Candidate Loci Identified by Re-analysis of a BSA Dataset for Ethanol Tolerance in Budding Yeast Since EXPLoRA combines increased sensitivity with a low false positive rate, we tested whether using EXPLoRA allows the identification of additional sites linked to high ethanol tolerance that could not be identified with statistical certainty in the original analysis (Swinnen et al., 2012a). We selected 0.7 as cut-off on the posterior probability (linkage score) since at this cut-off our method approaches the same low false positive rate that was also used in the original analysis, but reaches a higher sensitivity. We ran EXPLoRA on the pools selected for 16 and 17% ethanol separately, assuming that signals that are only weakly supported in the 16% ethanol pool should be confirmed by the signals obtained from the (smaller) sub-pool of segregants that were tolerant to 17% ethanol. Using $\alpha P=10$ and the cut-off on the linkage score of 0.7 allowed us to predict in the 16% pool 1 361 marker sites to be linked to higher ethanol tolerance, being located in 4 QTLs with an average size of 92 130 bp compared to predicting the linkage of 19 marker sites in an unselected pool being located in 4 small sized regions (on average 1 175 bp) (see Table 7). Analogously, analysis of the 17% pool allowed predicting linkage to the phenotype of 1 830 marker sites being located in 5 QTLs (regions with an average size of 148 310 bp) compared to predicting linkage of 25 marker sites in the unselected pool corresponding to 4 QTLs with an average size of only 1 250 bp. These numbers indicate that the QTLs predicted from the analysis of the selected pool almost surely are truly linked regions as no regions of similar size could be predicted to be linked in the unselected pool (estimated number of falsely predicted regions equals 0).

In addition to the previously identified loci (QTLs 1 and 3), we could distinguish in the pool selected for 16% ethanol, an additional significant QTL on chromosome X (referred to as QTL2). These three QTLs (QTL1-3) identified in the 16% pool were also detected in the analysis of the 17% ethanol pool using EXPLoRA, further increasing the confidence that these QTLs were truly linked to ethanol tolerance.

In addition to the QTLs detected in both the 16 and 17% ethanol tolerant pools, we identified with EXPLoRA two QTLs in the 17% ethanol pool, i.e., QTL4 located on chromosome XV and QTL5 located on chromosome II, none of which was described before (FIG. 10, panels D and F). Both QTLs appeared to be largely absent from the 16% ethanol tolerant pool (with the exception of a very small sized linked region identified in the 16% ethanol tolerant pool for QTL5, FIG. 10, panel E) and, therefore, seem to be specifically enriched during selection for very high ethanol tolerance.

For comparison, the original relative variant frequencies together with the linkage scores of, respectively, SHOREmap, the statistical model of Swinnen et al., 2012a, and EXPLoRA for these three additional loci (QTL2, QTL4 and QTL5) are shown in FIG. 10 for, respectively, the pool of 16% and 17% ethanol. Table 7 gives an estimation of the number of falsely linked marker sites and regions that were predicted at the maximal threshold needed to identify the indicated QTLs with each of the respective methods (see materials and methods). As described above, EXPLoRA detects these QTLs with a very low expected false positive rate at the level of the marker sites and a zero false positive rate at the level of the regions. On the other hand, for SHOREmap the expected number of falsely predicted marker sites/regions becomes prohibitive when using a cut-off on its linkage score that would allow prioritizing the same QTLs in the 16% and 17% pool that were reliably detected by EXPLoRA (see Table 7). For example, with a very low cut-off of 0.5, SHOREmap would detect in the 17% pool, 7 putative QTLs amongst which are QTL 3, 4 and 5 but with an expected false positive rate of 6 out of the 7 predicted regions. So, even after lowering the threshold on the linkage score drastically, SHOREmap can only reliably detect QTL3 in the pool selected for 17% ethanol tolerance. The figures also confirm that the method of Swinnen et al., 2012a, is conservative: after lowering the threshold considerably, it also succeeds in prioritizing QTL 4 and 5 with a low false positive detection rate (zero at the region level). However, because of its conservative character no single threshold exists that would allow detecting either QTL2 and QTL1 in the 17% pool as both regions have a zero linkage score with the statistical method of Swinnen et al., 2012a.

Example 10: Experimental Validation of the Newly Predicted QTL2 on Chromosome X

To assess the validity of our predictions, we selected QTL2 (on chromosome X) for experimental validation as this QTL not only seemed to be of major importance for ethanol tolerance, but was also detected only by EXPLoRA (even after lowering the threshold on the linkage score for the other methods). Performing fine-mapping of the region by PCR-based scoring of the markers in the individual segregants (materials and methods), allowed us to confirm the area with the strongest link (approximated by a 53 kb region, according to our predictions on the pool tolerant to 16% ethanol and by a 8.3 kb region, according to our predictions on the pool tolerant to 17% ethanol (FIG. 10, panels A and B) (FIG. 11A), Mutations in this confirmed region (about 29 kb, encompassing 16 genes) were verified with Sanger sequencing. All genes carrying non-synonymous mutations in their coding region were selected as candidate causative genes (FIG. 11A). True causative genes in QTL2 were identified using reciprocal hemizygosity analysis (Steinmetz et al., 2002). For each candidate causative gene a set of two diploid strains was constructed by crossing the parental strains, either containing or lacking the candidate gene. As a result, each diploid has a different allele of the candidate gene while the other copy of the gene is deleted (FIG. 11B). Phenotypic analysis on YPD plates with 16% ethanol showed a clear difference in ethanol tolerance between the two diploid strains carrying a different allele of VPS70: the strain with the allele derived from the VR1-5B superior parent grew very well in the presence of 16% ethanol, whereas the strain with the allele from the BY4741 inferior parent did not grow at all (FIG. 11C), indicating that VPS70 carries a causative mutation responsible for the link of QTL2 with high ethanol tolerance. Except for a putative role in sorting of vacuolar carboxypeptidase Y to the vacuole (Bonangelino et al., 2002), no link with ethanol tolerance for VPS70 has been reported (e.g., in van Voorst et al., 2006).

Example 11: Correlation Between Tolerance for Different Alkanols

The tolerance to alkanol of the two parent strains (VR1-5B and BY4741) and multiple segregants of the cross between the two parents was tested on YPD plates, with different alcohol concentrations. Ethanol tolerance was compared with tolerance to methanol, propanol, isopropanol, butanol and isobutanol. Growth was scored at each alcohol concentration based on the number of dilution spots in which growth was visible. For each strain the scores obtained at the different alcohol concentrations were counted together to obtain the cumulative growth score for that strain in the presence of the specified alcohol. The results are shown in FIG. 12. A linear correlation can be noticed between ethanol tolerance and tolerance for all the other alcohols tested.

Benjamin, Y. and Yekutieli, D. (2005) Quantitative trait Loci analysis using the false discovery rate. Genetics, 171, 783-790.

Blieck, L., Toye, G., Dumortier, F., Verstrepen, K. J., Delvaux, F. R., Thevelein, J. M. and Van Dijck, P. 2007. Isolation and characterization of brewer's yeast variants with improved fermentation performance under high-gravity conditions. Appl Environ Microbiol 73: 815-824.

Bonangelino, C. J., Chavez, E. M. and Bonifacino, J. S. (2002) Genomic screen for vacuolar protein sorting genes in Saccharomyces cerevisiae. Mol Biol Cell, 13, 2486-2501.

Boyd, A. R., Gunasekera, T. S., Attfield, P. V., Simic, K., Vincent, S. F., et al., 2003, A flow-cytometric method for determination of yeast viability and cell number in a brewery. FEMS Yeast Res 3: 11-16.

Brachmann, C. B., Davies, A., Cost, G. J., Caputo, E., Li, J., Hieter, P. and Boeke, J. D. 1998. Designer deletion strains derived from Saccharomyces cerevisiae S288C: a useful set of strains and plasmids for PCR-mediated gene disruption and other applications. Yeast 14: 115-132.

TABLE 7

Performance statistics of the different methods in the pool of segregants tolerant to 17% ethanol.

| | | Results for the unselected pool | | | Results for the selected pool | | | False positive rate | | |
|---|---|---|---|---|---|---|---|---|---|---|
| Method | Cut-off | Linked marker sites | Linked regions | Average length (bp) | Linked marker sites | Linked regions | Average length (bp) | Level of marker sites | Level of regions | Predicted QTLs |
| SHOREmap | 0.5 | 590 | 7 | 1 698 | 978 | 7 | 21 488 | 0.6 | 0.85 | QTL3 |
| | 0.6 | 331 | 8 | 1 357 | 740 | 8 | 14 333 | 0.44 | 0.88 | QTL3 |
| Swinnen et al., 2012a | 0.65 | 7 | 2 | 975 | 1 208 | 3 | 69 322 | 0.006 | 0 | QTLs 3, 4 & 5 |
| | 0.8 | 7 | 2 | 975 | 1 158 | 3 | 45 176 | 0.006 | 0 | QTLs 3 & 5 |
| EXPLoRa | 0.7 | 25 | 4 | 1 250 | 1 830 | 5 | 148 310 | 0.014 | 0 | QTLs 1, 2, 3, 4 & 5 |

Cut-off: maximal cut-off value on the linkage score needed to predict QTL4 and/or QTL5 by each method (see FIG. 10, panels D and F).
Linked marker sites: number of marker sites showing a linkage score that passes the chosen cut-off.
Linked regions: number of linked regions that result from grouping neighboring marker sites that were predicted to be linked at a chosen cut-off.
Average length: average length of linked regions at a chosen cut-off.
False positive rate (at the level of the marker sites): calculated as the number of linked marker sites from the unselected pool/total number of linked marker sites in the selected pool.
False positive rate (at the level of the regions): calculated as the number of linked regions predicted from the selected pool smaller in length than the 90 percentile largest region predicted in the unselected pool ("falsely linked regions")/total number of linked regions predicted in the unselected pool at the same chosen cut-off.
Predicted QTLs: "truly linked regions" larger in length than the 90 percentile largest called region in the unselected pool at the same chosen cut-off. The identity of the called regions is indicated by their respective QTL numbers.

REFERENCES

Abyzov, A., Urban, A. E., Snyder, M. and Gerstein, M. (2011) CNVnator: an approach to discover, genotype, and characterize typical and atypical CNVs from family and population genome sequencing. Genome Res, 21, 974-984.

Akao, T., Yashiro, I., Hosoyama, A., Kitagaki, H., Horikawa, H., et al., 2011, Whole-genome sequencing of sake yeast Saccharomyces cerevisiae Kyokai no. 7. DNA Res 18: 423-434.

Albers, E. and Larsson, C. (2009) A comparison of stress tolerance in YPD and industrial lignocellulose-based medium among industrial and laboratory yeast strains. J Ind Microbiol Biotechnol 36: 1085-1091.

Bardin, A. J., Boselli, M. G. and Amon, A. (2003) Mitotic exit regulation through distinct domains within the protein kinase Cdc15. Mol Cell Biol 23: 5018-5030.

Bartels, R. H., Beatty, J. C. and Barsky, B. A. (1987) And introduction to splines for use in computer graphics and geometric modeling. Mrogan Kaufmann Publishers.

Basso, T. O., Dario, M. G., Tonso, A., Stambuk, B. U. and Gombert, A. K. (2010) Insufficient uracil supply in fully aerobic chemostat cultures of Saccharomyces cerevisiae leads to respiro-fermentative metabolism and double nutrient-limitation. Biotechnol Lett 32: 973-977.

Brem, R. B., Yvert, G., Clinton, R. and Kruglyak L (2002) Genetic dissection of transcriptional regulation in budding yeast. Science 296: 752-755.

Carlsen, H. N., Degn, H. and Lloyd, D. (1991) Effects of alcohols on the respiration and fermentation of aerated suspensions of baker's yeast. J Gen Microbiol 137, 2879-2883.

Casal, M., Cardoso, H. and Ledo, C. (1998) Effects of ethanol and other alkanols on transport of acetic acid in Saccahromyces cerevisiae. Appl Environ Microbiol 64, 665-668.

Casey, G. P. and Ingledew, W. M. (1986) Ethanol tolerance in yeasts. Crit Rev Microbiol 13: 219-280.

Claesen, J., Clement, L., Shkedy, Z., Foulquié-Moreno, M. R. and Burzykowski, T. (2013) Simultaneous mapping of multiple gene loci with pooled segregants. PLoS One In press.

Cullen, P. J. and Sprague, G. F., Jr. (2002) The Glc7p-interacting protein Bud14p attenuates polarized growth, pheromone response, and filamentous growth in Saccharomyces cerevisiae. Eukaryot Cell 1: 884-894.

D'Amore, T. and Stewart, G. G. (1987) Ethanol tolerance of yeast. Enzyme and Microbial Technology 9: 322-330.

Deutschbauer, A. M. and Davis, R. W. (2005) Quantitative trait loci mapped to single-nucleotide resolution in yeast. Nat Genet 37: 1333-1340.

Ding, J., Huang, X., Zhang, L., Zhao, N., Yang, D., et al., 2009, Tolerance and stress response to ethanol in the yeast *Saccharomyces cerevisiae.* Appl Microbiol Biotechnol 85: 253-263.

Dohm, J. C., Lottaz, C., Borodina, T. and Himmelbauer, H. (2008) Substantial biases in ultra-short read data sets from high-throughput DNA sequencing. Nucleic Acids Res 36:e105.

Duitama, J., Srivastava, P. K. and Mandoiu, I. (2012) Towards accurate detection and genotyping of expressed variants from whole transcriptome sequencing data. BMC Genomics, 13, S6.

Ehrenreich, I. M., Torabi, N., Jia, Y., Kent, J., Martis, S., Shapiro, J. A., Gresham, D., Caudy, A. A. and Kruglyak, L. (2010) Dissection of genetically complex traits with extremely large pools of yeast segregants. Nature, 464, 1039-1042.

Gietz, R. D., Schiestl, R. H., Willems, A. R. and Woods, R. A. (1995) Studies on the transformation of intact yeast cells by the LiAc/SS-DNA/PEG procedure. Yeast 11: 355-360.

Hoffman, C. S. and Winston, F. (1987) A ten-minute DNA preparation from yeast efficiently releases autonomous plasmids for transformation of *Escherichia coli.* Gene 57: 267-272.

Homer, N., Merriman, B. and Nelson, S. F. (2009) BFAST: an alignment tool for large scale genome resequencing. PLoS One, 4, e7767.

Huxley, C., Green, E. D., Dunham, I. (1990) Rapid assessment of *S. cerevisiae* mating type by PCR. Trends Genet 6: 236.

Johnston, J. R. (1994) Molecular genetics of yeast: a practical approach; Press I, editor. New York.

Kodama, K. (1993) Sake-brewing yeast. In: Rose A H, Harrison J S, editors. The yeasts. London, United Kingdom: Academic Press. pp. 129-168.

Liti, G., Louis, E. J. (2012) Advances in quantitative trait analysis in yeast. PLoS Genet 8: e1002912.

Liti, G., Carter, D. M., Moses, A. M., Warringer, J., Parts, L., James, S. A., Davey, R. P., Roberts, I. N., et al., 2009, Population genomics of domestic and wild yeasts. Nature 458: 337-341.

Magwene, P. M., Willis, J. H. and Kelly, J. K. (2011) The statistics of bulk segregant analysis using next generation sequencing. PLoS Comput Biol, 7, e1002255.

Marullo, P., Aigle, M., Bely, M., Masneuf-Pomarede, I., Durrens, P., et al., 2007, Single QTL mapping and nucleotide-level resolution of a physiologic trait in wine *Saccharomyces cerevisiae* strains. FEMS Yeast Res 7: 941-952.

Moura, D. J., Castilhos, B., Immich, B. F., Canedo, A. D., Henriques, J. A., et al., 2010, Kin3 protein, a NIMA-related kinase of *Saccharomyces cerevisiae,* is involved in DNA adduct damage response. Cell Cycle 9: 2220-2229.

Myasnikov, A. N., Sasnauskas, K. V., Janulaitis, A. A. and Smirnov, M. N. (1991) The *Saccharomyces cerevisiae* ADE1 gene: structure, overexpression and possible regulation by general amino acid control. Gene 109: 143-147.

Nogami, S., Ohya, Y. and Yvert, G. (2007) Genetic complexity and quantitative trait loci mapping of yeast morphological traits. PLoS Genet 3: e31.

Ossowski, S., Schneeberger, K., Clark, R. M., Lanz, C., Warthmann, N. and Wiegel, D. (2008) Sequencing of natural strains of Arabidopsis thaliana with short reads. Genome Res 18: 2024-2033.

Parts, L., Cubillos, F. A., Warringer, J., Jain, K., Salinas, F., Bumpstead, S. J., Molin, M., Zia, A., Simpson, J. T., Quail, M. A. et al., 2011, Revealing the genetic structure of a trait by sequencing a population under selection. Genome Res, 21, 1131-1138.

Perlstein, E. O., Ruderfer, D. M., Roberts, D. C., Schreiber, S. L. and Kruglyak, L. (2007) Genetic basis of individual differences in the response to small-molecule drugs in yeast. Nat Genet 39: 496-502.

Puligundia, P., Smogrovicova, D., Obulam, V. S. R. and Ko, S. (2011) Very high gravity (VHG) ethanolic brewing and fermentation: a research update. J Ind Microbiol Biotechnol 38: 1133-1144.

Rozpedowska, E., Hellborg, L., Ishchuk, O. P., Orhan, F., Galafassi, S., et al., 2011, Parallel evolution of the make-accumulate-consume strategy in *Saccharomyces* and *Dekkera* yeasts. Nat Commun 2: 302.

Ruderfer, D. M., Pratt, S. C., Seidel, H. S. and Kruglyak, L. (2006) Population genomic analysis of outcrossing and recombination in yeast. Nat Genet, 38, 1077-1081.

Sheet, P. and Stephens, M. (2006) A fast and flexible statistical model for large-scale population genotype data: applications to inferring missing genotypes and haplotypic phase. Am J Hum Genet, 78, 629-644.

Shepherd, A. and Piper, P. W. (2010) The Fps1p aquaglyceroporin facilitates the use of small aliphatic amides as a nitrogen source by amidase-expressing yeasts. FEMS Yeast Res 10: 527-534.

Schneeberger, K., Ossowski, S., Lanz, C., Juul, T., Petersen, A. H., Nielsen, K. L., Jorgensen, J. E., Weigel, D. and Andersen, S. U. (2009) SHOREmap: simultaneous mapping and mutation identification by deep sequencing. Nat Methods, 6, 550-551.

Sherman, F. and Hicks, J. (1991) Micromanipulation and dissection of asci. Methods Enzymol 194: 21-37.

Steinmetz, L. M., Sinha, H., Richards, D. R., Spiegelman, J. I., Oefner, P. J., McCusker, J. H. and Davis, R. W. (2002) Dissecting the architecture of a quantitative trait locus in yeast. Nature, 416, 326-330.

Swinnen, S., Schaerlaekens, K., Pais, T., Claesen, J., Hubmann, G., Yang, Y., Demeke, M., Foulquie-Moreno, M. R., Goovaerts, A., Souvereyns, K. et al., 2012a, Identification of novel causative genes determining the complex trait of high ethanol tolerance in yeast using pooled-segregant whole-genome sequence analysis. Genome Res. 22, 975-984.

Swinnen, S., Thevelein, J. M. and Nevoigt, E. (2012b) Genetic mapping of quantitative phenotypic traits in *Saccharomyces cerevisiae.* FEMS Yeast Res, 12, 215-227.

Tusher, V. G., Tibshirrani, R. and Chu, G. (2001) Sigtnificance analysis of microarrays applied to ionizing radiation response. Proc Natl Acad Sci USA 98: 5116-5121.

van Voorst, F., Houghton-Larsen, J., Jonson, L., Kielland-Brandt, M. C. and Brandt, A. (2006) Genome-wide identification of genes required for growth of *Saccharomyces cerevisiae* under ethanol stress. Yeast, 23, 351-359.

Wahlbom, C. F., van Zyl, W. H., Jonsson, L. J., Hahn-Hagerdal, B. and Otero, R. R. 2003. Generation of the improved recombinant xylose-utilizing *Saccharomyces cerevisiae* TMB 3400 by random mutagenesis and physiological comparison with *Pichia stipitis* CBS 6054. *FEMS Yeast Res* 3 : 319-326.

Watanabe, M., Watanabe, D., Akao, T. and Shimoi, H. (2009) Overexpression of *MSN2* in a sake yeast strain promotes ethanol tolerance and increases ethanol production in sake brewing. J Biosci Bioeng 107: 516-518.

Wenger, J. W., Schwartz, K. and Sherlock, G. (2010) Bulk segregant analysis by high-throughput sequencing reveals a novel xylose utilization gene from *Saccharomyces cerevisiae*. PLoS Genet, 6, e1000942.

Winzeler, E. A., Richards, D. R., Conway, A. R., Goldstein, A. L., Kalman, S., et al., 1998, Direct allelic variation scanning of the yeast genome. Science 281: 1194-1197.

The invention claimed is:

1. A *Saccharomyces cerevisiae* yeast strain with higher alcohol accumulation produced by a method comprising:
   selecting the strain for a protein kinase 3 (KIN3) allele that allows for a higher alcohol accumulation and that comprises at least a thymidine at position 553 and a thymidine at position 1648, wherein the positions refer to SEQ ID NO: 7;
   selecting the strain for an adenine requiring 1 (ADE1) allele that comprises at least a thymidine at position 254, wherein the position refers to SEQ ID NO: 8;
   and introducing into the strain nucleic acid molecule encoding the amino acid sequence of SEQ 10 NO: 4; wherein the yeast strain produces increased alcohol concentration compared with alcohol concentration produced under identical conditions by a yeast that is genetically identical, apart from the selected KIN3 and ADE1 alleles and the introduced nucleic acid molecule.

2. The yeast strain of claim 1, wherein the KIN3 allele consists of SEQ ID NO.1.

3. The yeast strain of claim 1, further comprising at least one other alcohol tolerance modulating allele selected from the group consisting of vascuolar protein sorting 70 (VPS70), anti-prion dnaJ (APJ1) and sick without securin 2 (SWS2).

4. The yeast strain of claim 2, further comprising at least one other alcohol tolerance modulating allele selected from the group consisting of vacuolar protein sorting 70 (VPS70), anti-prion dnaJ (APJ1) and sick without securin 2 (SWS2).

5. The yeast strain of claim 4, further comprising an inactive APJ1 allelee.

6. The yeast strain of claim 4, further comprising an SWS2 allele that overexpresses SWS2 protein.

7. The yeast strain of claim 3, further comprising at least one allele selected from the group consisting of SEQ ID NO:3, SEQ ID NO:5, and SEQ ID NO:6.

8. The yeast strain of claim 7, further comprising the combination of SEQ ID NO:3 with a nucleic acid molecule encoding SEQ ID NO:4.

9. A process for producing ethanol, the process comprising: culturing the *saccharomyces cerevisiae* yeast strain of claim 1 to ferment sugars to ethanol.

10. The yeast strain of claim 1, wherein the ADE1 allele consists of SEQ ID NO:2.

11. A *Saccharomyces cerevisiae* yeast strain comprising:
   a protein kinase 3 (KIN3) allele having a thymidine at position 553 and a thymidine at position 1648, wherein the positions refer to SEQ ID NO: 7;
   an adenine requiring 1 (ADE1) allele that comprises a thymidine at position 254; wherein the position refers to in SEQ ID NO: 8;
   and a nucleic acid molecule encoding the amino acid sequence of SEQ ID NO: 4.

* * * * *

UNITED STATES PATENT AND TRADEMARK OFFICE
CERTIFICATE OF CORRECTION

PATENT NO. : 10,000,759 B2
APPLICATION NO. : 14/784893
DATED : June 19, 2018
INVENTOR(S) : Johan Thevelein et al.

It is certified that error appears in the above-identified patent and that said Letters Patent is hereby corrected as shown below:

In the Specification

| | | | |
|---|---|---|---|
| | Column 30, | Line 44, | change "we varied aP" to --we varied αP-- |
| | Column 36, | Line 1, | change "Benjamin, Y. and" to --Benjamini, Y. and-- |
| | Column 36, | Line 50, | change "and Ledo, C." to --and Leão, C.-- |

In the Claims

| | | | |
|---|---|---|---|
| Claim 1, | Column 65, | Line 65, | change "of SEQ 10 NO:" to --of SEQ ID NO:-- |
| Claim 2, | Column 66, | Line 57, | change "SEQ ID NO.1." to --SEQ ID NO: 1.-- |
| Claim 5, | Column 67, | Line 2, | change "inactive APJ1 allelee." to --inactive APJ1 allele.-- |

Signed and Sealed this
Twenty-eighth Day of August, 2018

Andrei Iancu
*Director of the United States Patent and Trademark Office*